(12) United States Patent
Leng

(10) Patent No.: US 12,371,725 B2
(45) Date of Patent: Jul. 29, 2025

(54) SYNTHESIS OF DNA MOLECULES IN IN VITRO ENZYMATIC SYSTEMS

(71) Applicant: Fenfei Leng, Palmetto Bay, FL (US)

(72) Inventor: Fenfei Leng, Palmetto Bay, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 55 days.

(21) Appl. No.: 18/494,425

(22) Filed: Oct. 25, 2023

(65) Prior Publication Data

US 2024/0141400 A1 May 2, 2024

Related U.S. Application Data

(60) Provisional application No. 63/419,037, filed on Oct. 25, 2022.

(51) Int. Cl.
*C12Q 1/6844* (2018.01)
*C12P 19/34* (2006.01)

(52) U.S. Cl.
CPC ............ *C12P 19/34* (2013.01); *C12Q 1/6846* (2013.01)

(58) Field of Classification Search
None
See application file for complete search history.

(56) References Cited

U.S. PATENT DOCUMENTS

2020/0248231 A1* 8/2020 Ito .......................... C12N 15/09

OTHER PUBLICATIONS

Peng, Generation of Long Insert Pairs Using a Cre-LoxP Inverse PCR Approach, PLoS One, 7(1): e29437, 1-8, 2012. (Year: 2012).*
Nakata, Quick validation of genetic quality for conditional alleles in mice, Genes Cells, 26: 240-245, 2021. (Year: 2021).*
Sayers, Identification and Eradication of a Denatured DNA Isolated during Alkaline Lysis-Based Plasmid Purification Procedures, Analytical Biochemistry, 241(2): 186-189, 1996. (Year: 1996).*
Duprey, DNA supercoiling differences in bacteria result from disparate DNA gyrase activation by polyamines, PLoS Genet, 16(1): e1009085, 1-20, 2020. (Year: 2020).*
Ali, Monsur M. et al. "Rolling circle amplification: a versatile tool for chemical biology, materials science and medicine." Chem Soc Rev 43(10):3324-3341, (Year: 2014).
An, Ran et al. "Highly efficient preparation of single-stranded DNA rings by T4 ligase at abnormally low Mg(II) concentration." Nucleic Acids Research 45(15):1-7, (Year: 2017).
Baker, Ysobel R. et al. "Expanding the chemical functionality of DNA nanomaterials generated by rolling circle amplification." Nucleic Acids Research 49(16):9042-9052, (Year: 2017).
Cantor, Eric J. & Chong, Shaorong "Intein-Mediated Rapid Purification of Cre Recombinase." Protein Expression and Purification 22(1):135-140, (Year: 2001).
Dean, Frank et al. "Rapid Amplification of Plasmid and Phage DNA Using Phi29 DNA Polymerase and Multiply-Primed Rolling Circle Amplification." Genome Research 11(6):1095-1099, (Year: 2001).
Deng, Zifang & Leng, Fenfei "A T5 Exonuclease-Based Assay for DNA Topoisomerases and DNA Intercalators." ACS Omega 6(18):12205-12212, (Year: 2021).
Ghosh, Kaushik & Van Duyne, Gregory D. "Cre-LoxP biochemistry." Methods 28(3):374-383, (Year: 2002).
Goryunova, M. S. et al. "Rolling circle amplification with fluorescently labeled dUTP-balancing the yield and degree of labeling." Analytical and Bioanalytical Chemistry 413, pp. 3737-3748, (Year: 2021).
Jiang, Ying et al. "Supramolecularly Engineered Circular Bivalent Aptamer for Enhanced Functional Protein Delivery." J Am Chem Soc. 140(22):6780-6784, Jun. 6, 2018.
Kick, Benjamin et al. "Efficient Production of Single-Stranded Phage NDA as Scaffolds for DNA Origami." Nano Letters 15(7): 4672-4676, (Year: 2015).
Kim, Kyoung-Ran et al. "Shaping Rolling Circle Amplification Products into DNA Nanoparticles by Incorporation of Modified Nucleotides and Their Application to In Vitro and In Vivo Delivery of a Photosensitizer." Molecules 23(7):1-14, (Year: 2018).
Kuhn, Heiko & Frank-Kamenetskii, Maxim D. "Template-independent ligation of single-stranded DNA by T4 DNA ligase." The FEBS Journal 272(23):5991-6000, (Year: 2005).
Meyer-Leon et al. "Purification of the FLP site-specific recombinase by affinity chromatography and re-examination of basic properties of the system." Nucleic Acids Research 15(16):6469-6488, (Year: 1987).
Parmley, Stephen F. & Smith, George P. "Antibody-selectable filamentious fd phage vectors: affinity purification of target genes." Gene 73(2):305-318, (Year: 1988).
Quadros, Rolen M. et al. "Easi-CRISPR: a robust method for one-step generation of mice carrying conditional and insertion alleles using long ssDNA donors and CRISPR ribonucleoproteins." Genome Biology 18(92):1-15, (Year: 2017).
Schaub Jeffrey M. "Assessing Protein Dynamics on Low-Complexity Single-Stranded DNA Curtains." Langmuir, 34(49):14882-14890, (Year: 2018).
Scott, Jamie K. & Smith, George P. "Searching for Peptide Ligands with an Epitope Library." Science 249(4967):386-390, Jul. 27, 1990.
Shen, Tingting et al. "Single-stranded circular DNA theranostics." Theranostics 12(1):35-47, (Year: 2022).

(Continued)

*Primary Examiner* — Gary Benzion
*Assistant Examiner* — Carolyn L Greene
(74) *Attorney, Agent, or Firm* — SALIWANCHIK, LLOYD & EISENSCHENK

(57) ABSTRACT

A method, which synthesizes closed circular single-stranded and double-stranded DNA molecules using in vitro enzymatic systems, is described. Circular single-stranded DNA molecules and double-stranded DNA molecules (e.g., relaxed, or supercoiled) with various sizes can be synthesized. Unwanted DNA molecules, e.g., unligated oligomers, can be removed by exonucleases, such as T5 exonuclease, T7 exonuclease, lambda exonuclease, *E. coli* exonuclease I and/or III. A method of converting the single-stranded circular DNA molecules into double-stranded circular DNA molecules is also described. The single-stranded and double-stranded circular DNA molecules can be used in a variety of applications.

7 Claims, 43 Drawing Sheets

Specification includes a Sequence Listing.

(56) References Cited

OTHER PUBLICATIONS

Shepherd, Tyson R. et al. "Bioproduction of pure, kilobase-scale single-stranded DNA." Scientific Reports 9(1):1-9, (Year: 2019).
Sui, Zhe et al. "Stepwise strategy for one-pot synthesis of single-stranded DNA rings from multiple short fragments." ChemBioChem 22(6):1005-1011, (Year: 2021).
Sui, Zhe et al. "Efficient preparation of large-sized rings of single-stranded DNA through one-pot ligation of multiple fragments." Chemistry—An Asian Journal 14(17):3251-3254, (Year: 2019).
Meira, Jeffrey & Messing, Joachim "Production of Single-Stranded Plasmid Dna." Methods in Enzymology 153, pp. 3-11, (Year: 1987).
Wang, Yunke et al. "Kinetic Study of DNA Topoisomerases by Supercoiling-Dependent Fluorescence Quenching." ACS Omega 4(19):18413-18422, (Year: 2019).
Yang, Litao et al. "Real-Time Rolling Circle Amplification for Protein Detection." Anal. Chem. 79(9):3320-3329, (Year: 2007).
Yanisch-Perron, Celeste et al. "Improved M13 phage cloning vectors and host strains: nucleotide sequences of the M13mp18 and pUC19 vectors." Gene 33(1):103-119, (Year: 1985).
Yoshimi, Kazuto et al. "SsODN-mediated knock-in with CRISPR-Cas for large genomic regions in zygotes." Nature Communications 7(1): 1-11, Jan. 20, 2016.
Zhou, Fang et al. "Molecular Engineering-based Aptamer-Drug Conjugates with Accurate Tunability of Drug Ratios for Drug Combination Targeted Cancer Therapy." Angewandte Chemie International Edition 58(34):11661-11665, (Year: 2019).

\* cited by examiner

SYNTHESIS OF DNA MOLECULES IN IN VITRO ENZYMATIC SYSTEMS

CROSS-REFERENCE TO RELATED APPLICATION

This application claims the benefit of U.S. Provisional Application Ser. No. 63/419,037 filed Oct. 25, 2022, which is hereby incorporated by reference herein in its entirety.

SEQUENCE LISTING

The Sequence Listing for this application is labeled "SeqList-25oct23.xml," which was created on Oct. 25, 2023, and is 2,631 bytes. The entire content is incorporated herein by reference in its entirety.

BACKGROUND

Closed circular DNA molecules including circular double-stranded DNA (dsDNA) and single-stranded DNA (ssDNA) molecules have been explored for therapeutic use. For instance, 482 gene therapy clinical trials (14.7% of the total trials) used plasmid DNA, small circular dsDNA molecules found in bacteria and some other microscopic organisms (a873679.fmphost.com/fmi/webd/GTCT). ZyCoV-D, a plasmid-based COVID-19 vaccine has been approved for clinic use in India. Several other plasmid DNA-based COVID-19 vaccines are in development at different phases and hopefully will enter the fight against COVID-19 soon. Additionally, several plasmid DNA-based vaccines are approved for veterinary use in animals (www.ema.europa.eu/en/medicines/veterinary/EPAR/clynav).

Circular ssDNA molecules also possess unique features and are valuable and important for DNA nanotechnology, molecular biology, medicine and biotechnology. These circular ssDNA molecules are more resistant against exonucleases and form unique structures such as duplexes and triplexes, compared to linear DNAs. Circular ssDNA molecules have been heavily used in rolling circle amplification and rolling circle transcription technologies.

In rolling circle DNA amplification, the circular ssDNAs, in combination with short strands of single-stranded complementary primer DNAs, are employed as templates for replication by DNA polymerase, which provides concatemers containing tens to hundreds of tandem repeats and has been widely adopted for various purposes. Recent results showed that circular ssDNA molecules are much more efficient DNA donors for CRISPR/Cas9 mediated genome editing with minimal off-target integration.

Plasmid DNA molecules are usually constructed, maintained, and produced in E. coli cells. They are heat stable and easy to store and transport. Additionally, plasmids have a very low integration rate into a host genome and can be administered repeatedly. However, several drawbacks limit their clinical use. Plasmids contain bacterial DNA sequences required for propagation and selection in E. coli host strains, including origin of replication and antibiotic resistance encoding genes. Not only do these DNA sequences increase the plasmid size, but they may lead to an immune response and gene silencing as well. The antibiotic resistance-encoding gene can also be transferred LU bacteria in the human microbiome. Furthermore, residual endotoxin and/or antibiotic is difficult to be "completely" removed from the final product and may trigger immune reactions in patients.

Due to these limitations, DNA minicircles generated in vivo using site-directed recombination, consisting almost entirely of the target gene cassette without bacterial DNA sequences, have been explored for potential clinical applications. Nevertheless, parent plasmid contamination is still high, which is a great concern for therapeutic applications. The high cost of producing minicircles also prevent them from clinical use.

Because (−) supercoiled DNA is the physiologically preferred form of DNA for the transfection of mammalian cells, linear dsDNA molecules, which cannot be supercoiled, may limit their potential for clinical use. Negative supercoiling makes DNA more compact, which promotes nuclear localization and provides additional protection from the shear forces of aerosolization. A better method to synthesize supercoiled (Sc) circular dsDNA molecules is urgently needed for therapeutic applications.

Currently, two types of methods are used to produce ss circular DNA molecules, in vitro ligation of linear DNA molecules and bacterial phage M13-based methods. Linear DNA molecules (synthetic oligomers or generated by PCR or RCA) can be ligated to circular ss DNA with the help of a splint by a DNA ligase in vitro. A weakness of this method is the low yield of producing large size ss circular DNA. Another method is the use of phage M13 or phagemids to produce ss circular DNA molecules. A drawback of this method is that certain bacterial DNA sequences, such as phage M13 replication origin, are still required and may cause issues for the following applications. Due to these weaknesses, an innovative method to produce large quantities of ss circular DNA molecules with a defined sequence is needed for different applications.

Although various reported methodologies are available to synthesize circular dsDNA and ssDNA molecules, the complicated protocols and the associated cost limit the utility of these methodologies. The existing methods also require multiple steps and are time consuming. Thus, there is a need for developing simple, rapid, robust and efficient methods for synthesizing circular dsDNA and ssDNA molecules to be utilized in various applications.

BRIEF SUMMARY

The subject invention provides methods, compositions and kits for efficiently synthesizing closed circular single-stranded nucleic acids and double-stranded nucleic acids of various sizes and sequences. The principle of the method for efficiently synthesizing closed circular single-stranded nucleic acids and double-stranded nucleic acids is to ligate two stem-loop or hairpin DNA molecules into a circular single-stranded DNA molecule.

The subject invention also provides compositions comprising the synthesized closed circular single-stranded nucleic acids and double-stranded nucleic acids according to the subject invention. Further provided are methods of utilizing the synthesized single-stranded nucleic acids and double-stranded nucleic acids for various purposes.

Applications of this method include providing circular single-stranded DNA templates for CRISPR/Cas9-mediated DNA recombination, and for cloning and expressing proteins in different organisms.

In one embodiment, the subject invention provides synthetic oligomers having a stem-loop or hairpin structure, and methods of use thereof to produce single-stranded circular DNA molecules containing target sequences or genes of interest.

In one embodiment, the method for synthesizing a circular single-stranded DNA molecule comprises annealing a first synthetic oligomer and a second synthetic oligomer, wherein the first synthetic oligomer and the second synthetic oligomer each has a stem-loop or hairpin structure; adding a ligase; and adding an exonuclease.

In one embodiment, each of the first and second synthetic oligomers comprises an overhang, wherein the overhang of the first synthetic oligomer has a sequence complementary to the sequence of the overhang of the second synthetic oligomer such that annealing the first and second synthetic oligomers leads to the hybridization of the complementary overhangs.

In one embodiment, the ligase is a DNA ligase, for example, *E. coli* DNA ligase, Taq DNA ligase, or T4 DNA ligase. The exonuclease is T7 exonuclease and lambda exonuclease.

In one embodiment, the method for synthesizing a circular single-stranded DNA molecule further comprises adding isopropanol, washing with 70% ethanol, and dialyzing against a buffer, e.g., 10 mM Tris-HCl.

In one embodiment, the first synthetic oligomer comprises a DNA replication origin (e.g., a ColE1 replication origin) and a selection marker (e.g., an ampicillin resistance gene, a gene producing β-lactamase, a kanamycin resistance gene, or a tetA). The second synthetic oligomer comprises a gene, a promoter (e.g., T7 promoter) and a transcription terminator (e.g., T7 terminator).

In one embodiment, one or more of the first and second synthetic oligomer comprise a detectable label, e.g., a fluorescent dye.

The subject invention further provides methods to synthesize large quantities of supercoiled double-stranded (ds) circular DNA molecules in an in vitro enzymatic system. The subject invention also provides methods to produce circular ssDNA molecules in vitro enzymatically.

Synthesizing circular DNA molecules in an in vitro enzymatic system provides the following advantages: 1) the final circular DNA products/molecules do not contain genomic DNA, RNA, endotoxin, or antibiotic contaminations; 2) the in vitro synthesized circular DNA molecules do not carry unwanted sequences, such as a bacterial plasmid replication origin or an antibiotic resistance gene, except a 34 bp loxP sequence; 3) because T5, T7, and/or lambda exonuclease is used to degrade unwanted DNA molecules, the purification of circular DNA molecules is simplified and inexpensive; 4) the cost to produce circular DNA molecules in the in vitro enzymatic system is low; 5) the in vitro enzymatic systems are scalable and can produce circular DNA molecules from µg to grams; and 6) because phi29 DNA polymerase can use modified nucleotides for the RCA reactions, circular DNA molecules with modified nucleotides can be produced for a variety of applications.

In one embodiment, the subject invention provides a method for synthesizing a circular double-stranded DNA molecule, the method comprising:
  annealing one or more oligomers to double-stranded DNA molecules, wherein the one or more oligomers can be synthetic oligomers or products of PCR or RCA;
  performing ligation reactions to ligate the double-stranded DNA molecules to form a long linear double-stranded DNA molecule, and ligate two double-stranded oligomers carrying loxP sites to the long linear double-stranded DNA molecule, in the presence of a DNA ligase, wherein the DNA ligase is, for example, *E. coli* DNA ligase, Taq DNA ligase, or T4 DNA ligase;
  adding a recombinase to convert the long linear double-stranded DNA molecule carrying loxP sites to a relaxed circular double-stranded DNA molecule, wherein the recombinase is selected from serine family recombinases and tyrosine family recombinases, preferably, the recombinase is Cre recombinase and/or yeast FLP recombinase;
  adding an exonuclease (e.g., T5, T7 or lambda exonuclease); and
  optionally, adding DNA gyrase to convert the relaxed double-stranded DNA molecule to a supercoiled double-stranded DNA molecule.

In one embodiment, the subject invention provides a method for synthesizing a circular double-stranded DNA molecule using an in vitro enzymatic system, the method comprising:
  providing a nicked circular DNA template comprising two sequence-specific recombination sites;
  performing rolling circle amplification (RCA) to produce a double-stranded DNA product comprising the two sequence-specific recombination sites;
  adding an endonuclease to the double-stranded DNA product to produce a linear double-stranded DNA fragment comprising the two sequence-specific recombination sites;
  converting the linear double-stranded DNA fragment to a relaxed circular double-stranded DNA molecule; and
  optionally, converting the relaxed circular double-stranded DNA molecule to a supercoiled double-stranded DNA molecule.

In one embodiment, the subject invention provides a method for synthesizing a circular double-stranded DNA molecule, the method comprising:
  providing a DNA template comprising two sequence-specific recombination sites;
  performing PCR to produce a linear double-stranded DNA fragment comprising the two sequence-specific recombination sites;
  converting the linear double-stranded DNA fragment to a relaxed circular double-stranded DNA molecule; and
  optionally, converting the relaxed circular double-stranded DNA molecule to a supercoiled double-stranded DNA molecule.

In one embodiment, the subject invention further provides a kit for use to synthesize a circular single-stranded DNA molecule, the kit comprising a first synthetic oligomer, a second synthetic oligomer, a ligase and an exonuclease, wherein the first synthetic oligomer and the second synthetic oligomer each has a stem-loop or hairpin structure.

In one embodiment, the subject invention further provides a kit for use to synthesize a circular single-stranded DNA molecule, the kit comprising one or more synthetic oligomers, a ligase and an exonuclease, wherein each synthetic oligomer can be linear or has a stem-loop or hairpin structure.

The single-stranded circular products of the present invention are suited for use as a substrate in, e.g., rolling circle amplification and rolling circle transcription technologies. The product prepared by the method according to the present invention can ultimately yield single-strand concatenated DNA having numerous different sequential segments that can act as, for example, probes, detection sites or restriction sites for further processing.

In one embodiment, the subject invention provides a kit for synthesizing circular DNA molecules, the kit comprising a DNA template comprising two sequence-specific recombination sites, DNA primers, a DNA polymerase, dNTPs, a recombinase, DNA Topoisomerase, buffers, T5 exonuclease, and an endonuclease.

In one embodiment, the subject invention uses PCR as a method to synthesize supercoiled (Sc) or relaxed (Rx) DNA molecules in vitro. This method can be versatile and be used at either small or large scale. By using such method, two new plasmids pLoxFL1 and pLoxFL2 have been constructed, which can be used as platform to synthesize circular DNA molecules in vitro. For example, two mini circles (a 430 bp mini circle (mini circle 1) from pLoxFL1) and a 427 bp mini circle (minicircle 2) from pLoxFL2 have been synthesized. The subject invention provides a new technology for in vitro synthesis of circular DNA molecules, which can, for example, be used as medicines for treating diseases.

BRIEF DESCRIPTION OF SEQUENCES

Figure 1A:
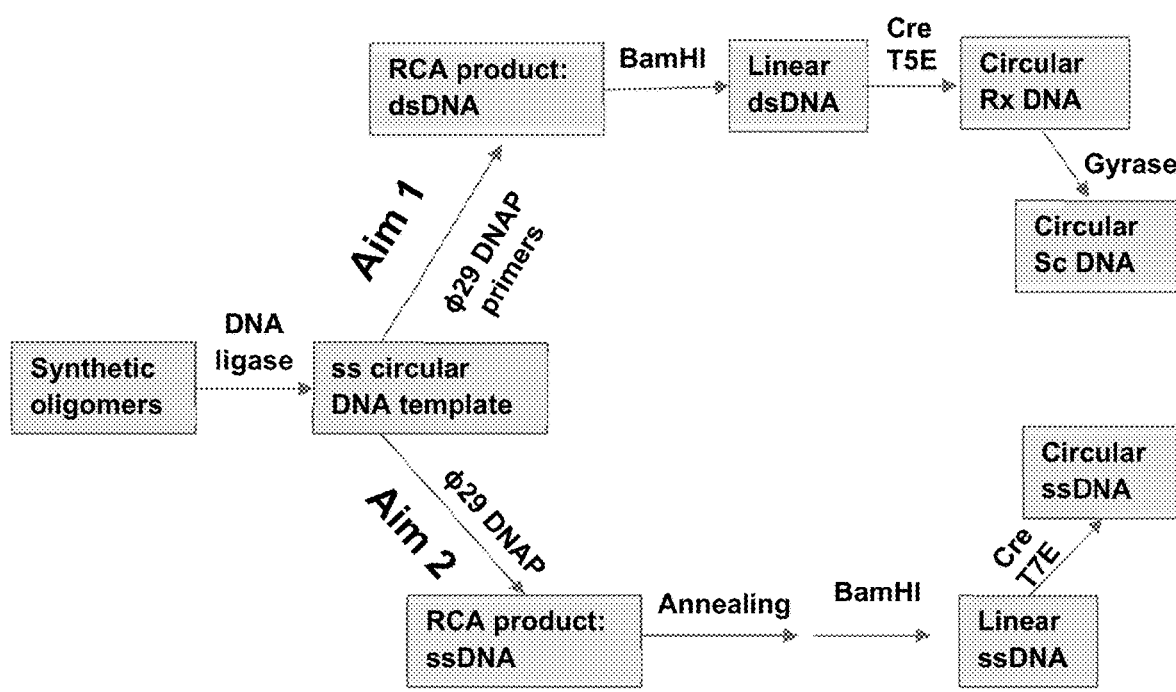
FIGS. 1A-1C show schemes for synthesizing circular DNA molecules. 1A) a scheme for synthesizing circular Sc dsDNA (aim 1) and circular ssDNA (aim 2). 1B) a scheme for synthesizing circular DNA in vitro via rolling circle amplification (RCA) using phi29 DNA polymerase. 1C) a scheme for synthesizing relaxed (Rx) and supercoiled (Sc) circular DNA molecules in vitro by using polymerase chain reaction (PCR). Symbols: ss, single-stranded; ds, double-stranded; Φ29 DNAP, phi29 DNA polymerase; RCA, rolling circle amplification; Rx, relaxed, Sc, supercoiled; Cre, Cre recombinase; T5E, T5 exonuclease; T7E, T7 exonuclease.
Figure 1B:
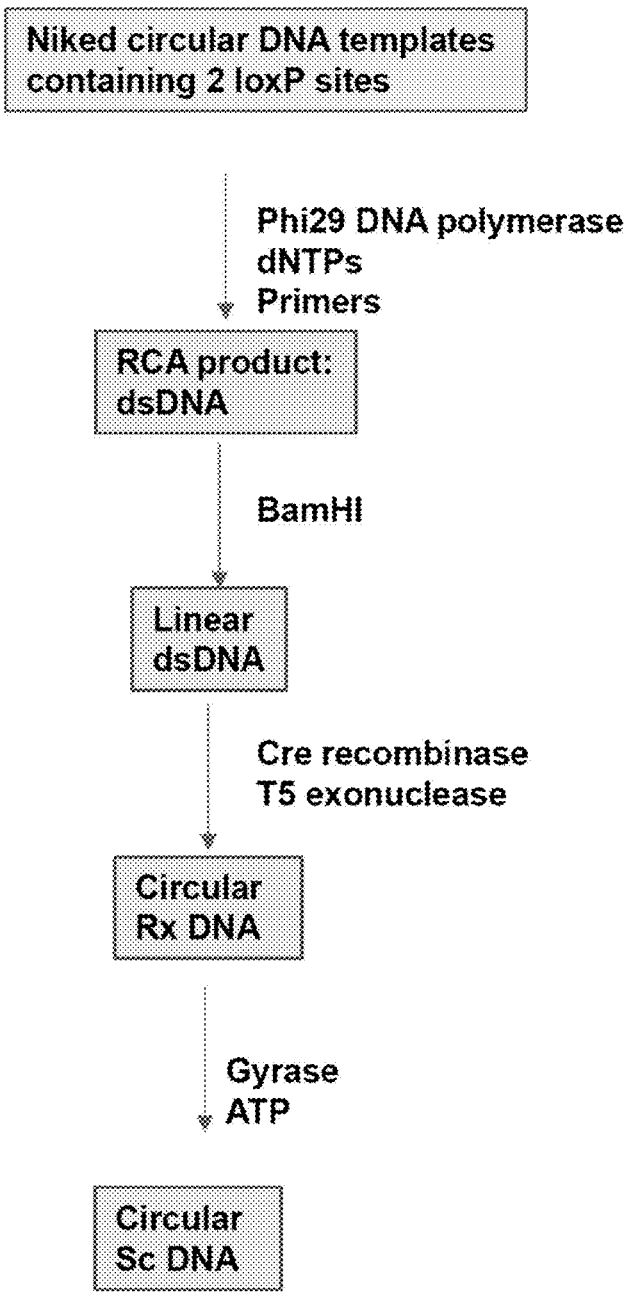

SEQ ID NOs: 1-2 are primer sequences contemplated for use according to the subject invention.

DETAILED DESCRIPTION

The subject invention provides materials, methods, compositions and kits for efficiently synthesizing closed circular single-stranded nucleic acids (e.g., single-stranded DNAs) and double-stranded nucleic acids (e.g., double-stranded DNAs) of various sizes and sequences. The principle of the method for efficiently synthesizing closed circular single-stranded nucleic acids and double-stranded nucleic acids is to ligate two stem-loop or hairpin nucleic acids, e.g., two stem-loop or hairpin DNA molecules, into a circular single-stranded DNA (ssDNA) molecule.

Specifically, circular single-stranded DNA (ssDNA) molecules can be generated in vitro and in E. coli for different applications, such as serving as DNA templates for RCA by phi29 DNA polymerase, drug delivery, diagnostics, genome editing, etc. Advantageously, ssDNA molecules are much more efficient DNA donors for CRISPR/Cas9 mediated genome editing with minimal off target integration.

The subject invention also provides compositions comprising the synthesized closed circular single-stranded nucleic acids and double-stranded nucleic acids according to the subject invention. Further provided are methods of utilizing the synthesized single-stranded nucleic acids and double-stranded nucleic acids for various purposes, e.g., as DNA templates for CRISPR/Cas9 DNA recombination and molecular cloning and expression.

In one embodiment, the subject invention provides synthetic oligonucleotides/oligomers and methods of use thereof to produce single-stranded nucleic acids (e.g., ssDNAs) and double-stranded nucleic acids (e.g., dsDNAs). The synthetic oligonucleotides/oligomers, each having a stem-loop or hairpin structure, can readily be ligated to each other to form, after heat denaturation, enlarged circular ssDNAs containing predetermined nucleotide sequences of the starting oligonucleotides/oligomers. Advantageously, the methods use such synthetic oligonucleotides/oligomers without the need for multiple cycles of synthesis and ligation.

In one embodiment, each of the synthetic oligonucleotides/oligomers is single-stranded and comprises a first portion having the sequence complementary to that of a second portion within the same synthetic oligonucleotide/oligomer, which allows the synthetic oligonucleotide/oligomer to self-anneal, thereby forming a pseudo-circular or hairpin structure. The synthetic oligonucleotide/oligomer may have a blunt end or a sticky end with an overhang composed of a portion of a terminal sequence of the single-stranded synthetic oligomer.

In one embodiment, the subject invention provides a method for synthesizing circular single-stranded nucleic acids (e.g., ssDNA), the method comprising:
    annealing a first synthetic oligomer and a second synthetic oligomer, wherein the first synthetic oligomer and the second synthetic oligomer each has a hairpin structure, wherein the first and second synthetic oligomer comprise identical or different sequences;
    adding a ligase, preferably, DNA ligase, more preferably, T4 DNA ligase; and
    adding an exonuclease or a mixture of exonuclease.

In one embodiment, the first synthetic oligomer comprises a region in the overhang complementary to a region in the overhang of the second synthetic oligomer such that annealing the first and second synthetic oligomers leads to the hybridization of the complementary regions. Then, addition of a ligase (e.g., E. coli DNA ligase, Taq DNA ligase, or T4 DNA ligase) seals the nick between the ends of the first and second synthetic oligomers. Further, addition of an exonuclease, for example, E. coli exonuclease I and/or III, removes any unligated synthetic oligomers.

Figure 16A:
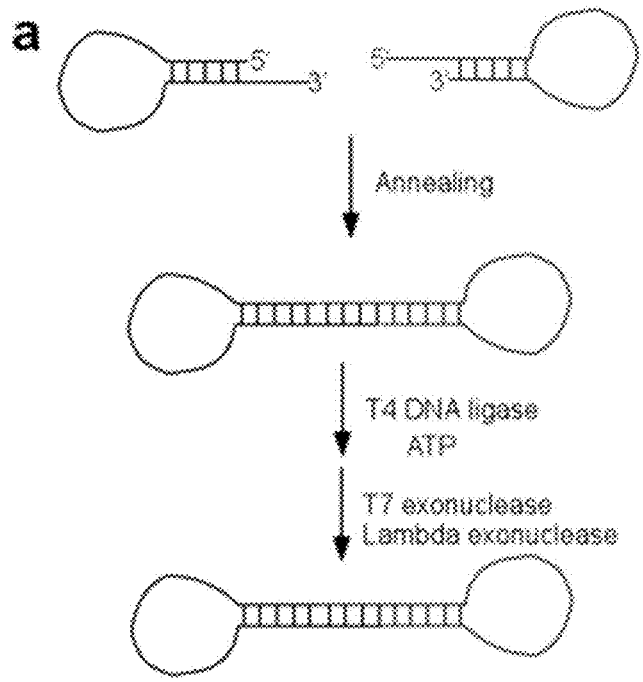
FIGS. 16A-16B, show general design/principle of the methods. 16A) Two stem-loop or hairpin DNA molecules can be ligated into a single-stranded circular DNA molecule. 16B) A stem-loop or hairpin DNA molecule may also form a dimer.
Figure 16B:
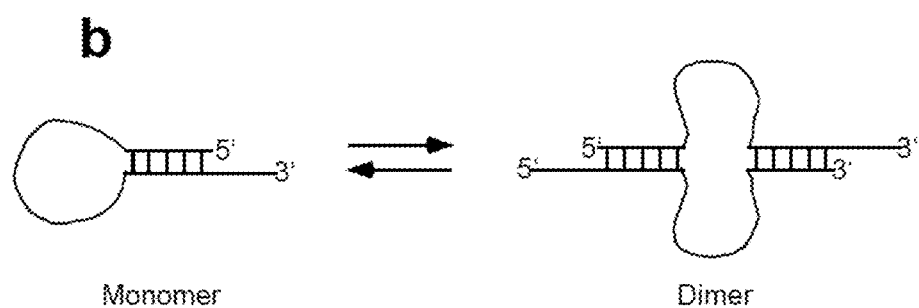

FIGS. 16A-16B show a general design/principle of the method. A single stranded oligomer can form a stem-loop or hairpin structure if the oligomer contains a 5'-terminus or 3'-terminus complementary to another sequence of the same oligomer (FIG. 16A). By design, two such single stranded oligomers can be efficiently ligated by T4 DNA ligase or other ligase after annealing if the termini are complementary to each other. Un-ligated oligomers (single-stranded) may be removed by *E. coli* exonuclease I and/or III (or other enzymes).

In one embodiment, the synthetic oligonucleotide is of any length, for example, at least 8 nucleotides, at least 10 nucleotides, at least 15 nucleotides, at least 20 nucleotides, at least 25 nucleotides, at least 30 nucleotides, at least 35 nucleotides, at least 40 nucleotides, at least 55 nucleotides, at least 50 nucleotides, at least 60 nucleotides, at least 70 nucleotides, at least 80 nucleotides, at least 90 nucleotides, at least 100 nucleotides, at least 125 nucleotides, at least 150 nucleotides, at least 200 nucleotides, at least 250 nucleotides, at least 300 nucleotides, at least 400 nucleotides, at least 500 nucleotides, at least 600 nucleotides, at least 700 nucleotides, at least 800 nucleotides, at least 900 nucleotides, at least 1,000 nucleotides, at least 1500 nucleotides, at least 2000 nucleotides, at least 3000 nucleotides, at least 4000 nucleotides, or at least 5000 nucleotides.

In one embodiment, the synthetic oligonucleotide may comprise, for example, about 8 nucleotides to about 10000 nucleotides, about 10 nucleotides to about 5000 nucleotides, about 10 nucleotides to about 4000 nucleotides, about 20 nucleotides to about 3000 nucleotides, about 30 nucleotides to about 2000 nucleotides, about 40 nucleotides to about 1000 nucleotides, about 50 nucleotides to about 500 nucleotides, about 60 nucleotides to about 400 nucleotides, about 70 nucleotides to about 300 nucleotides, about 80 nucleotides to about 200 nucleotides, or about 50 nucleotides to about 100 nucleotides.

In one embodiment, the synthetic oligomer has a hairpin structure with a loop having, for example, at least 4 nucleotides, at least 10 nucleotides, at least 15 nucleotides, at least 20 nucleotides, at least 25 nucleotides, at least 30 nucleotides, at least 35 nucleotides, at least 40 nucleotides, at least 55 nucleotides, at least 50 nucleotides, at least 60 nucleotides, at least 70 nucleotides, at least 80 nucleotides, at least 90 nucleotides, at least 100 nucleotides, at least 125 nucleotides, at least 150 nucleotides, at least 200 nucleotides, at least 250 nucleotides, at least 300 nucleotides, at least 400 nucleotides, at least 500 nucleotides, at least 600 nucleotides, at least 700 nucleotides, at least 800 nucleotides, at least 900 nucleotides, at least 1000 nucleotides, at least 1500 nucleotides, at least 2000 nucleotides, or at least 3000 nucleotides.

In one embodiment, the loop of the synthetic oligonucleotide comprise, for example, about 4 nucleotides to about 10000 nucleotides, about 4 nucleotides to about 9000 nucleotides, about 4 nucleotides to about 8000 nucleotides, about 4 nucleotides to about 7000 nucleotides, about 4 nucleotides to about 6000 nucleotides, about 4 nucleotides to about 5000 nucleotides, about 10 nucleotides to about 5000 nucleotides, about 10 nucleotides to about 4000 nucleotides, about 20 nucleotides to about 3000 nucleotides, about 30 nucleotides to about 2000 nucleotides, about 40 nucleotides to about 1000 nucleotides, about 50 nucleotides to about 500 nucleotides, about 60 nucleotides to about 400 nucleotides, about 70 nucleotides to about 300 nucleotides, about 80 nucleotides to about 200 nucleotides, or about 50 nucleotides to about 100 nucleotides.

In one embodiment, the synthetic oligomer has a hairpin structure with a stem having, for example, at least 2 base pairs, at least 5 base pairs, at least 10 base pairs, at least 15 base pairs, at least 20 base pairs, at least 30 base pairs, at least 40 base pairs, at least 50 base pairs, at least 100 base pairs, at least 150 base pairs, at least 200 base pairs, or at least 300 base pairs.

In one embodiment, the synthetic oligomer has a hairpin structure with a stem having, for example, 2 base pairs to 500 base pairs, 3 base pairs to 400 base pairs, 4 base pairs to 300 base pairs, 5 base pairs to 200 base pairs, 5 base pairs to 100 base pairs, 6 base pairs to 90 base pairs, 7 base pairs to 80 base pairs, 8 base pairs to 70 base pairs, 9 base pairs to 60 base pairs, 10 base pairs to 50 base pairs, 10 base pairs to 40 base pairs, 10 base pairs to 30 base pairs, or 10 base pairs to base pairs.

In some embodiments, the two stem sequences of the synthetic oligomer are complementary to each other, or exhibit a significant degree of complementarity (e.g., 100% complementary, 99% complementary, 98% complementary, 95% complementary, 90% complementary, 85% complementary, 80% complementary, 75% complementary, 70% complementary, 65% complementary, 60% complementary, etc.).

In some embodiments, the loop sequence is sequence known in the art to form stable loops (e.g., UUCG, GNRA, GGGG, etc.). In some embodiments, a loop is random sequence, or pseudorandom sequence between the two stem sequences.

The oligomers may form a dimer due to the existence of complementary sequences (FIG. 16B). Certain experimental conditions can be used to increase the monomer concentration. First, diluted concentration of oligomers will significantly increase the formation of the monomer. Second, short loops should also favor the formation of monomer. Third, low ionic condition, especially low concentrations of $Mg^{2+}$, favor the monomer formation. Fourth, a partial double-stranded DNA in the loop also favors the monomer due to the stereo clash. Fifth, certain molecular crowding agents, such as PEG20,000 or PVA20,000 should increase the concentration of the monomer.

In some embodiments, the ligase comprises a DNA ligase. In some embodiments, the ligase comprises T4, T. aquaticus, or *E. coli* DNA ligase. In some embodiments, the ligase repairs the nick between the 3' end and the 5' end of the oligonucleotide sequence.

In a specific embodiment, the method of synthesizing circular ssDNAs comprises:
1) annealing the oligomers to form the stem-loop or hairpin structure with certain experimental conditions: low concentrations of oligomer, to low ionic concentration (for example, 10 mM Tris-HCl, pH 8 or 10 mM Tris-HCl and 1 mM NaCl), and in the presence of PEG20,000 or PVA20,000;
2) Adding 1 mM of DTT, 1 mM ATP, and 10 mM MgCl2 or MgAC2 to the solution;
3) Adding T4 DNA ligase to initiate the ligation reaction;
4) adding *E. coli* exonuclease I and/or III to remove the un-ligated oligomers; and
5) adding isopropanol, washing with 70% ethanol, and dialyzing against a buffer, such as 10 mM Tris-HCl in 4° C. to arrive at the final closed circular single-stranded DNA.

In one embodiment, the synthetic oligonucleotides/oligomers can be formed from two or more small oligomer fragments that having a length of, for example, ≤200 nucleotides, ≤190 nucleotides, ≤180 nucleotides, ≤170 nucleotides, ≤160 nucleotides, ≤150 nucleotides, ≤140 nucleotides, ≤130 nucleotides, ≤120 nucleotides, ≤110 nucleotides, ≤100 nucleotides, ≤90 nucleotides, ≤80 nucleotides, ≤70 nucleotides, ≤60 nucleotides, ≤50 nucleotides, ≤40 nucleotides, ≤30 nucleotides, ≤20 nucleotides, or ≤10 nucleotides.

Figure 17A:
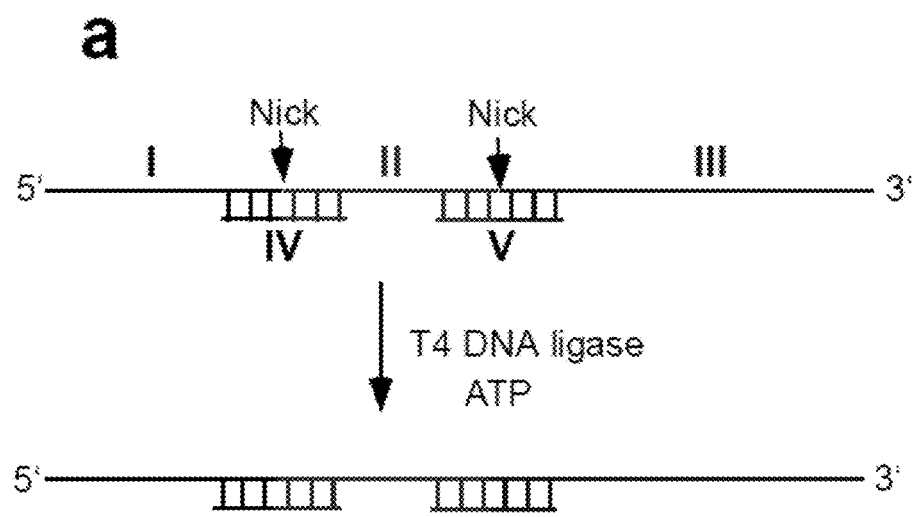
FIGS. 17A-17B show how to make a stem-loop or hairpin structure with a large loop from small synthetic oligomers. 17A) Short synthetic oligomers (oligomers I, II, and III) can be ligated into longer single-stranded guided by splints (oligomers IV and V). 17B) An experimental strategy to construct stem-loop or hairpin DNA molecule with a large loop.
Figure 17B:
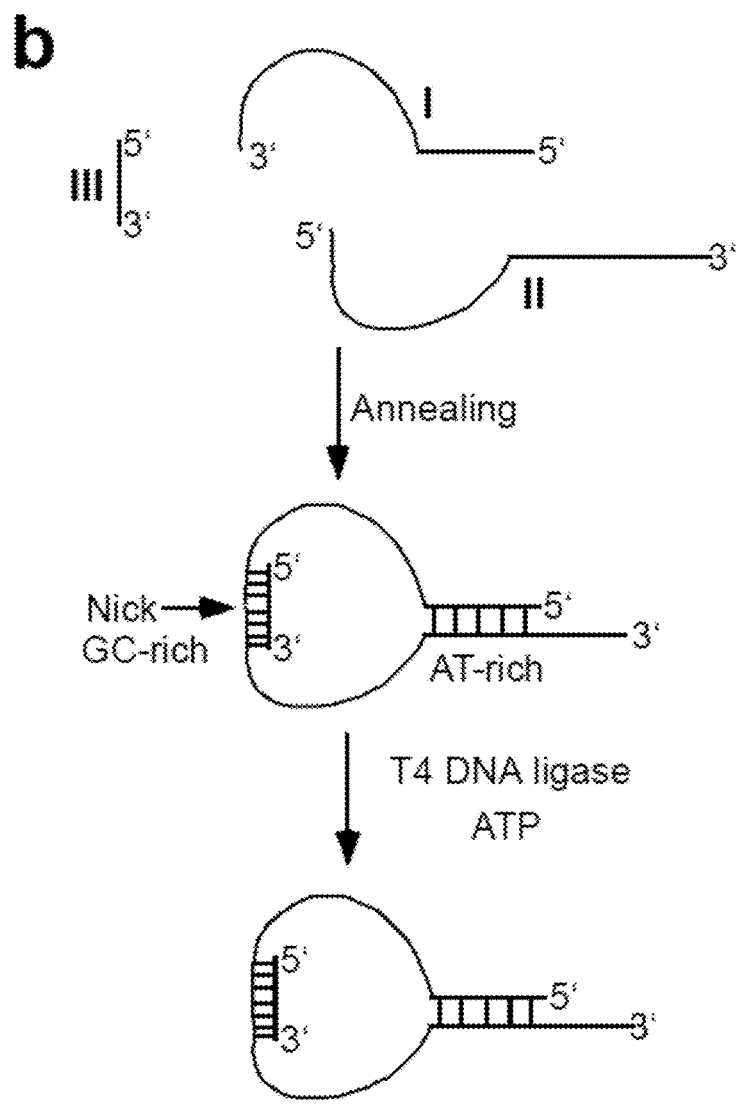

Small oligomer fragments (e.g., less than 150 nucleotides long) can be ligated to longer oligomers, guided by splints, DNA oligonucleotides complementary to the termini of adjacent two small oligomers. For example, FIG. 17A shows that three short oligomers can be ligated to a longer oligomer guided by two splints in the presence of a ligase. FIG. 17B shows that a stem-loop or hairpin structure with a large loop can be constructed through ligating two single-stranded oligomers. These two oligomers can be ligated by T4 DNA ligase assisted by a splint. A stem can be formed between the complementary sequences of these two oligomers with a sticky end (FIG. 17B).

In specific embodiments, the splint is GC-rich (e.g., ≥50% GC, ≥55% GC, ≥60% GC, ≥65% GC, ≥70% GC, ≥75% GC, ≥80% GC, ≥85% GC, ≥90% GC, ≥95% GC, ≥98% GC, or ≥99% GC). The complementary sequences between those two oligomers are AT-rich (e.g., ≥50% AT, ≥55% AT, ≥60% AT, ≥65% AT, ≥70% AT, ≥75% AT, ≥80% AT, ≥85% AT, ≥90% AT, ≥95% AT, ≥98% AT, or ≥99% AT). In this way, the splint anneals with the two oligomers, leading to the formation of a structure comprising a nicked double stranded DNA. Then, the AT-rich double-stranded sequence forms after temperature decreases (FIG. 17B). After T4 DNA ligase ligates the two oligomers, a stem-loop or hairpin structure forms.

In one embodiment, the method for synthesizing an oligomer having a stem-loop or hairpin structure, suitable for the synthesis of the circular ssDNA molecule comprises:
providing one or more small oligomers each having a predetermined sequence;
providing one or more splints, each having a sequence complementary to the termini of two small oligomers so that each splint hybridizes with the termini of two small oligomers, forming a nicked sequence; and
adding a ligase to form the oligomer.

In one embodiment, the subject invention also provides a method for synthesizing a stem-loop or hairpin DNA molecule suitable for the synthesis of the circular ssDNA, the method comprises:
1) providing a first oligomer and a second oligomer, each having a predetermined sequence, wherein the first and second oligomers comprise regions that complementary to each other, wherein said regions of the first and second oligomers are located at or near 5' or 3' end, and wherein said regions of the first and second oligomers are AT-rich (e.g., ≥50% AT, ≥55% AT, ≥60% AT, ≥65% AT, ≥70% AT, ≥75% AT, ≥80% AT, ≥85% AT, ≥90% AT, ≥95% AT, ≥98% AT, or ≥99% AT);
2) providing a splint, wherein the splint comprises a sequence complementary to the termini of the first and second oligomers such that the splint hybridizes with the termini of the first and second oligomers (e.g., 3' terminal sequence of the first oligomer and 5' terminal sequence of the second oligomer), forming a nicked sequence, wherein the splint is GC-rich (e.g., ≥50% GC, ≥55% GC, ≥60% GC, ≥65% GC, ≥70% GC, ≥75% GC, ≥80% GC, ≥85% GC, ≥90% GC, ≥95% GC, ≥98% GC, or ≥99% GC); and
3) adding a ligase to seal the nick and form the stem-loop or hairpin DNA molecule.

In specific embodiments, the first synthetic oligomer having a stem-loop or hairpin structure comprises a DNA replication origin (e.g., a ColE1 replication origin) and a selection marker (e.g., a gene producing β-lactamase, kanamycin resistance gene, or tetA). The second synthetic oligomer having a stem-loop or hairpin structure comprises a gene of interest to be cloned or expressed, a promoter and a transcription terminator. Preferably, the promotor is a T7 promoter or other promoters recognized by T7 RNA Polymerase.

The gene of interest can be from any suitable source. In some embodiments, the target gene-containing nucleic acids are derived from any suitable source, and for purposes related to any field, including but not limited to diagnostics, research, medicine, forensics, epidemiology, pathology, archaeology, etc. In some embodiments, target gene-containing nucleic acids are derived from, for example, eukaryotes, prokaryotes (e.g., infectious bacteria), mammals, humans, non-human primates, canines, felines, bovines, equines, porcines, mice, viruses, etc.

In a specific embodiment, the first synthetic oligomer having a stem-loop or hairpin structure comprises a ColE1 replication origin and an ampicillin resistance gene. The second synthetic oligomer having a stem-loop or hairpin structure comprises a GFP gene under the control of T7 promoter and terminator.

In one embodiment, the subject invention provides a method of converting the single-stranded circular DNA molecules into double-stranded circular DNA molecules. Specifically, small synthetic DNA fragments complementary to the circular single-stranded DNA molecule anneal and are ligated by T4 DNA ligase to yield a gapped DNA molecule. The gap is located in one strand of the stem structure to prevent the formation of short double-stranded DNA fragments in this region. The gap can be filled with an excess of an oligomer complementary to the gap DNA sequence. After DNA ligation, T5 exonuclease is used to remove DNA fragments.

As used herein, the terms "region," "portion," "segment," and "fragment," when used in relation to polynucleotides or oligonucleotides of any kind, including the hairpin oligonucleotides described herein, refer to a continuous sequence of nucleotide residues, which sequence forms a subset of a larger sequence.

In one embodiment, the method of converting the single-stranded circular DNA molecules into double-stranded circular DNA molecules comprises providing a circular ssDNA molecule synthesized according to the subject invention; providing small DNA fragments complementary to the sequence of circular single-stranded DNA molecule; annealing the mixture of the circular ssDNA molecule and small DNA fragments; adding a ligase, e.g., T4 DNA ligase; and adding an exonuclease, e.g., T5 exonuclease.

The single-stranded and double-stranded circular DNA molecules synthesized according to the subject invention have many applications. For example, single-stranded and double-stranded circular DNA molecules can be used as DNA templates for CRISPR/Cas9 DNA recombination and molecular cloning and expression.

In some embodiments, the synthetic oligomer may be modified by addition of one or more reporter labels (or detectable labels). In some embodiments, the label may be attached to either the 5' or 3' end of the synthetic oligomer. The label may also be attached to the backbone of the synthetic oligomer. The skilled person will be aware of techniques for attaching labels to nucleic acid strands. The detectable label may be attached directly or indirectly to the nucleic acids. If the label is indirectly attached to the nucleic acids, it may be by any mechanism known to one of skill in the art, such as using biotin and streptavidin.

In certain embodiments, the synthetic oligomer may comprise a reporter label, such as a fluorescent dye, or nanoparticle. Exemplary labels include, but are not limited to, an organic donor fluorophore or an organic acceptor fluorophore, a luminescent lanthanide, a fluorescent or luminescent nanoparticle, an affinity tag such as biotin, or a polypeptide.

In some embodiments, the synthetic oligomer may comprise a fluorescent label, for example, fluorescein, TAMRA®, rhodamine, Texas Red®, Alexa Fluor™ (e.g., AlexaFluor™ 488, AlexaFluor™ 532, AlexaFluor™ 546, AlexaFluor™ 594, AlexaFluor™ 633 and AlexaFluor™ 647), cyanine dye (e.g., Cy7®, Cy7.5®, Cy5®, Cy5.5® and Cy3®), Tye dye (e.g., TYE™ 563, TYE™ 665, TYE™ 705), atto dye (e.g., ATTO™ 594 and ATTO™ 633), Hexachlorofluorescein, FAM® (6-carboxyfluroescein), BODIPY® FL, OliGreen®, 40,6-diamidino-2-phenylindol (DAPI), Hoechst® 33,258, malachite green (MG), and FITC. In some embodiments, the fluorophore is selected from the group consisting of fluorophores that emit a blue, green, near red or far red fluorescence.

In one embodiment, the reporter label is a fluorescent dye and quencher pair. The quenchers can be, for example, Dabcyl, DDQ-I, Eclipse®, Iowa Black FQ®, BHQ®-1, QSY®-7, BHQ®-2, DDQ-II, Iowa Black RQ®, QSY®-21, or BHQ®-3.

In a specific embodiment, the subject invention provides a method for synthesizing a ss DNA circle having about 180 nt.

In a specific embodiment, the subject invention provides a method for synthesizing a ss DNA circle having about 270 nt.

In a specific embodiment, the subject invention provides a method for synthesizing a ss DNA circle having about 600 nt and a ss DNA circle having about 1000 nt.

In a specific embodiment, the subject invention provides a method for synthesizing a ss DNA circle having about 4000 nt with ColE1 replication origin, an Amp selection marker, and a gfp gene under T7 promoter and terminator control.

In specific embodiments, the subject invention provides a method for synthesizing relaxed and supercoiled ds DNA circles having about 180, 270, 600, and 1000 bp, respectively.

In a specific embodiment, the subject invention provides a method for synthesizing fluorescently labeled relaxed and supercoiled ds DNA circles.

In a specific embodiment, the subject invention provides a method for synthesizing a ds DNA with hairpin ends.

In one embodiment, the subject invention provides a cell (e.g., eukaryotes or prokaryotes), transformed with a circular ssDNA molecule synthesized according to the subject invention. In a specific embodiment, the cell is an $E.$ $coli$ cell.

In one embodiment, the subject invention provides a circular ssDNA molecule synthesized by the method of the subject invention.

In one embodiment, the circular ssDNA molecule comprises a DNA replication origin, a selection marker, a gene of interest, a promoter and a transcription terminator. In a specific embodiment, the circular ssDNA molecule comprises a ColE1 replication origin, an ampicillin resistance gene, a gene of interest, a T7 promoter and a T7 terminator.

In a specific embodiment, the circular ssDNA has a dumbbell shape with two loops connected with a double-stranded region. In specific embodiments, the DNA replication origin, and selection marker are located in one loop region of the circular ssDNA molecule while the gene of interest, the promoter and the transcription terminator are located in another loop region of the circular ssDNA molecule.

In some embodiments, the double-stranded region of the circular ssDNA molecule is complementary to each other, or exhibit a significant degree of complementarity (e.g., 100% complementary, 99% complementary, 98% complementary, 95% complementary, 90% complementary, 85% complementary, 80% complementary, 75% complementary, 70% complementary, 65% complementary, 60% complementary, 55% complementary, 50% complementary, etc.).

In some embodiments, the double-stranded region of the circular ssDNA molecule is AT-rich (e.g., ≥20% AT, ≥30% AT, ≥40% AT, ≥50% AT, ≥55% AT, ≥60% AT, ≥65% AT, ≥70% AT, ≥75% AT, ≥80% AT, ≥85% AT, ≥90% AT, ≥95% AT, ≥98% AT, or ≥99% AT).

In some embodiments, the circular ssDNA molecule may comprise additional promoters, suppressers, enhancers, and terminators.

In one embodiment, the circular ssDNA molecule comprises, for example, at least 15 nucleotides, at least 20 nucleotides, at least 25 nucleotides, at least 30 nucleotides, at least 35 nucleotides, at least 40 nucleotides, at least 55 nucleotides, at least 50 nucleotides, at least 60 nucleotides, at least 70 nucleotides, at least 80 nucleotides, at least 90 nucleotides, at least 100 nucleotides, at least 125 nucleotides, at least 150 nucleotides, at least 200 nucleotides, at least 250 nucleotides, at least 300 nucleotides, at least 400 nucleotides, at least 500 nucleotides, at least 600 nucleotides, at least 700 nucleotides, at least 800 nucleotides, at least 900 nucleotides, at least 1000 nucleotides, at least 1500 nucleotides, at least 2000 nucleotides, at least 3000 nucleotides, at least 4000 nucleotides, or at least 5000 nucleotides.

In one embodiment, the circular ssDNA molecule comprises, for example, about 15 nucleotides to about 10000 nucleotides, about 20 nucleotides to about 9000 nucleotides, about 30 nucleotides to about 8000 nucleotides, about 40 nucleotides to about 7000 nucleotides, about 50 nucleotides to about 6000 nucleotides, about 60 nucleotides to about 5000 nucleotides, about 70 nucleotides to about 4000 nucleotides, about 80 nucleotides to about 3000 nucleotides, about 90 nucleotides to about 2000 nucleotides, about 100 nucleotides to about 1000 nucleotides, or about 100 nucleotides to about 500 nucleotides.

In one embodiment, the circular dsDNA may be in a relaxed or supercoiled state and can switch between a relaxed state and a supercoiled state.

In one embodiment, the subject invention provides compositions comprising small oligomers suitable for synthesizing the oligomers having a stem-loop or hairpin structure as described herein.

In one embodiment, the subject invention provides compositions comprising synthetic oligomers having a stem-loop or hairpin structure synthesized as described herein.

In one embodiment, the subject invention provides compositions comprising a circular ssDNA molecule synthesized as described herein.

The subject invention provides an in vitro enzymatic system to produce circular DNA molecules (e.g., relaxed (Rx) and supercoiled (Sc) circular double-stranded DNA molecules and circular ssDNA molecules) in such a scale that can support therapeutic applications such as gene therapy and DNA vaccines. Also provided are methods to produce circular DNA molecules in vitro enzymatically.

Based on a combination of the high fidelity and processivity of phi29 DNA polymerase for rolling circle amplification (RCA) of DNA, the highly efficient site-specific recombination of, for example, Cre DNA recombinase to generate circular DNA molecules, and selective digestion of unwanted DNA molecules by, for example, T5 and T7 exonucleases, large quantities of circular DNA molecules can be produced for various biomedical applications (FIG. 1A).

In one embodiment, the subject invention provides in vitro enzymatic methods to synthesize Rx and Sc circular dsDNA molecules. In another embodiment, the subject invention provides in vitro enzymatic methods to synthesize closed single-stranded or double-stranded circular DNA molecules.

There are many advantages to synthesize closed circular DNA molecules in an in vitro enzymatic system. These advantages include: 1) the final circular DNA products/molecules do not contain genomic DNA, RNA, endotoxin, or antibiotic contamination; 2) the in vitro synthesized circular DNA molecules do not carry unwanted sequences, such as a bacterial plasmid replication origin or an antibiotic resistance gene, except a 34 bp loxP sequence; 3) because exonucleases such as T5, T7, and/or lambda exonuclease are used to degrade unwanted DNA molecules, the purification of circular DNA molecules is simplified and inexpensive; 4) because proteins and enzymes can be purified inexpensively, the cost to produce circular DNA molecules in the in vitro enzymatic systems is low; 4) both in vitro enzymatic systems are scalable and can produce circular DNA molecules from µg to grams; and 5) because phi29 polymerase can use modified nucleotides for the RCA reactions, circular DNA molecules with modified nucleotides can be produced for different applications.

In certain embodiments, the in vitro enzymatic system comprises a combination of enzymes selected from DNA ligases (e.g., E. coli DNA ligase, Taq DNA ligase, or T4 DNA ligase), exonucleases, endonucleases, DNA polymerases, DNA recombinases (e.g., serine family recombinases and tyrosine family recombinases), DNA topoisomerases and restriction enzymes. In some embodiments, the in vitro enzymatic system may further comprise a DNA plasmid comprising recognition sites of exonucleases, endonuclease, and restriction enzymes, wherein the DNA plasmid is suitable for molecular cloning, for example, for incorporating target DNA sequences.

In specific embodiments, the in vitro enzymatic system comprises a combination of enzymes selected from T4 DNA ligase, T7 exonuclease, lambda exonuclease, phi29 DNA polymerase, Taq or Phusion DNA polymerase, BamHI, Cre DNA recombinase, T5 exonuclease, DNA gyrase, DNA topoisomerase I, EcoRI, HindIII, Nt.BbvCI, SspI, SphI, XbaI, KpnI, XhoI, PstI, and AatII.

In specific embodiments, the in vitro enzymatic system comprises a combination of enzymes selected from T4 DNA ligase, T7 exonuclease, phi29 DNA polymerase, Taq or Phusion DNA polymerase, BamHI, Cre DNA recombinase, T5 exonuclease, DNA gyrase, and DNA topoisomerase I.

In some embodiments, the site-specific recombinases are selected from serine family recombinases (such as Salmonella Hin invertases and transposon Tn3 and γδ resolvases), and tyrosine family recombinases (such as bacteriophage λintegrase, phage P1 Cre, E. Coli XerC and XerD, and yeast FLP).

In one embodiment, the in vitro enzymatic method for synthesizing a closed single-stranded circular DNA molecule comprises:
  providing one or more oligomers, which may be synthetic or PCR products;
  obtaining ss circular DNA templates from the one or more oligomers in the presence of a DNA ligase;
  performing RCA in the presence of a DNA polymerase, preferably, phi29 DNA polymerase, to form ss DNA molecules;
  annealing the ss DNA molecules to produce a long linear single-stranded DNA molecule, e.g., in the presence of a DNA ligase (e.g., E. coli DNA ligase, Taq DNA ligase, or T4 DNA ligase); and
  adding a recombinase, e.g., Cre recombinase, to convert the linear single-stranded DNA molecules to the closed single-stranded circular DNA molecule.

In some embodiments, the in vitro enzymatic method to synthesize a closed/circular single-stranded circular DNA molecule further comprises the use of an exonuclease, e.g., T5 or T7 exonuclease, to degrade unligated linear DNA molecules.

In one embodiment, the ss circular DNA or ds circular DNA templates are nicked circular DNA templates containing 2 loxP sites.

In one embodiment, the RCA is performed in the presence of, for example, dNTPs and primers.

In a specific embodiment, BamHI, a restriction endonuclease, is used to recognize and cleave the DNA sequences, e.g., the RCA product, at a target site to produce a linear ds or ss DNA.

In certain embodiments, the one or more oligomers and/or the circular ss DNA and circular ds DNA comprise a gene of interest to be transformed and expressed in cells for, for example, molecular cloning.

In one embodiment, the in vitro enzymatic method for synthesizing a circular Rx and/or Sc dsDNA molecule comprises:
  providing one or more oligomers, which may be synthetic or PCR products;
  obtaining ss circular DNA templates from the one or more oligomers in the presence of a DNA ligase;
  performing RCA or PCR in the presence of a DNA polymerase, preferably, phi29 DNA polymerase and at least two primers, to form ds DNA molecules;
  annealing the ds DNA molecules to produce a linear ds DNA molecule, e.g., in the presence of a DNA ligase (e.g., E. coli DNA ligase, Taq DNA ligase, or T4 DNA ligase);
  adding a recombinase, e.g., Cre recombinase, to convert the linear ds DNA molecule to the circular Rx ds DNA molecule; and
  optionally, adding a DNA gyrase to convert the Rx ds DNA molecule to a Sc ds DNA molecule.

In some embodiments, the in vitro enzymatic method for synthesizing a circular Rx and/or Sc dsDNA molecule further comprises the use of an exonuclease, e.g., 15 or T7 exonuclease, to degrade unligated linear DNA molecules.

In one embodiment, the subject invention provides a method for synthesizing single-stranded circular DNA molecules from synthetic oligomers, the method comprising:
  1) performing ligation reactions to produce long linear single-stranded DNA molecules using 5-phosporlated oligomers, e.g., in the presence of splints and a DNA ligase (e.g., E. coli DNA ligase, Taq DNA ligase, or T4 DNA ligase);
  2) ligating two double-stranded oligomers (or hairpins) carrying loxP sites to the long linear single-stranded DNA molecules by a DNA ligase;
  3) adding a recombinase, e.g., Cre recombinase, to convert the linear single-stranded DNA molecules to single-stranded circular DNA molecules; and 4) adding an exonuclease, e.g., T5 exonuclease, to degrade unligated linear DNA molecules.

In one embodiment, the subject invention provides a method for synthesizing double-stranded circular DNA molecules from synthetic oligomers or linear DNAs from other sources (e.g., PCR or RCA products), the method comprising:
1) providing synthetic oligomers or linear DNAs, e.g., 5'-phorsphated oligomers, wherein the synthetic oligomers or linear DNAs are annealed to double-stranded DNA molecules, and wherein the linear DNA molecules can be produced by PCR or RCA;
2) performing ligation reactions to produce a long linear double-stranded DNA molecule, e.g., in the presence of a DNA ligase, such as T4 DNA ligase;
3) performing a ligation reaction to ligate two double-stranded oligomers carrying loxP sites to the linear double-stranded DNA molecule by a DNA ligase, e.g., E. coli DNA ligase, Taq DNA ligase, or T4 DNA ligase, wherein the double-stranded oligomers may be linear or hairpins carrying loxP sites;
4) adding a recombinase, e.g., Cre recombinase, to convert the linear double-stranded DNA molecule formed in step 3) to a relaxed circular double-stranded DNA molecule;
5) adding an exonuclease, e.g., T5 exonuclease, to degrade unligated linear DNA molecules; and
6) optionally, adding a DNA gyrase to convert the relaxed double-stranded DNA molecule to a supercoiled double-stranded DNA molecule.

In one embodiment, the double-stranded circular DNA molecules can be synthesized using PCR products. In specific embodiments, the method for synthesizing a double-stranded circular DNA molecule comprises the step of performing PCR reactions using two primers each carrying a loxP site, wherein each primer comprises the 34 bp loxP site that is AT-rich.

In a specific embodiment, the primer may comprise loxP mutants. In a preferred embodiment, the two primers are different from each other, wherein one primer contains a loxP site and another primer carries a nicking endonuclease recognition site. In a further embodiment, PCR products can be digested by a nicking enzyme.

In specific embodiments, the method for synthesizing a double-stranded circular DNA molecule further comprises:
annealing the oligomers/primers each carrying a loxP site;
ligating the annealed oligomers/primers to the PCR product, i.e., the linear double-stranded DNA molecule;
adding a recombinase, e.g., Cre recombinase, to convert the linear double-stranded DNA molecule comprising loxP sites to a relaxed circular double-stranded DNA molecule;
adding an exonuclease, e.g., T5 exonuclease, to degrade unligated linear DNA molecules; and
adding a DNA gyrase to convert the relaxed double-stranded DNA molecule to a supercoiled double-stranded DNA molecule.

In one embodiment, the subject invention provides a method for synthesizing a circular ss DNA molecule, the method comprising obtaining/providing a linear ss DNA molecule containing two sequence-specific recombination sites; adding a recombinase, e.g., Cre recombinase; and adding an exonuclease, e.g., T7 exonuclease or lambda exonuclease, wherein the linear ss DNA molecule being a synthetic DNA oligomer, a PCR product, or a single-stranded DNA molecule from RCA by a DNA polymerase, e.g., phi29 DNA polymerase.

In a specific embodiment, each of the two sequence-specific recombination sites is selected from loxP sites and flippase recognition target (FRT) sites.

In one embodiment, the subject invention provides a method for synthesizing a circular ds DNA molecule, the method comprising:
obtaining a linear double-stranded DNA molecule carrying two loxP sites on the same direction, wherein the linear double-stranded DNA molecule can be a product of RCA by phi29 DNA polymerase, a product of PCR, or a synthetic DNA oligomer;
adding a recombinase to convert the linear double-stranded DNA molecule carrying two loxP sites to a relaxed circular double-stranded DNA molecule;
adding an exonuclease; and
optionally, adding a DNA gyrase to convert the relaxed double-stranded DNA molecule to a supercoiled double-stranded DNA molecule.

In certain embodiments, the linear synthetic linear DNA oligomers can be produced from annealing one or more oligomers to double-stranded DNA molecules; and performing ligation reactions to ligate the double-stranded DNA molecules to form a long linear double-stranded DNA molecule and ligate two double-stranded oligomers carrying loxP sites to the long linear double-stranded DNA molecule.

In one embodiment, the subject invention provides a method for synthesizing a circular double-stranded DNA molecule of a target sequence using in vitro enzymatic system of the subject invention, the method comprising:
providing a nicked circular DNA template comprising two sequence-specific recombination sites flanking the target sequence, wherein the two sequence-specific recombination sites are selected from loxP sites, FRT sites and a combination thereof, and wherein the nicked circular DNA template is a single-stranded DNA molecule comprising digestion sites of Nt.BbvC1 and/or BamHI;
performing rolling circle amplification (RCA) to produce a double-stranded DNA product comprising the sequence-specific recombination sites flanking the target sequence, wherein the RCA is performed in the presence of a DNA polymerase (e.g., phi29 DNA polymerase), dNTPs and primers (e.g., SEQ ID NOs: 1 and 2);
adding an endonuclease (e.g., BamHI) to the double-stranded DNA product to produce a linear double-stranded DNA fragment comprising the sequence-specific recombination sites flanking the target sequence;
converting the linear double-stranded DNA fragment to a relaxed circular double-stranded DNA molecule of the target sequence, wherein converting the linear double-stranded DNA fragments to the relaxed circular double-stranded DNA molecule comprises a recombination reaction in the presence of a recombinase (e.g., Cre recombinase) and a digestion reaction in the presence of an exonuclease (e.g., T5E); and
optionally, converting the relaxed circular double-stranded DNA molecule to a supercoiled double-stranded DNA molecule, wherein converting the relaxed circular double-stranded DNA molecule to the supercoiled double-stranded DNA molecule comprising adding a DNA topoisomerase (e.g., DNA gyrase and DNA topoisomerase I).

In one embodiment, the subject invention provides a method for synthesizing circular DNA via RCA using phi29 DNA polymerase, the method comprising providing nicked circular DNA templates containing 2 loxP sites, preferably, the nicked circular DNA templates further comprising digestion sites of, for example, Nt.BbvCI and/or BamHI, and preferably, the nicked circular DNA templates are circular ss DNA molecules; performing RCA to produce circular dsDNA in the presence of, for example, DNA polymerase (e.g., phi29 DNA polymerase), dNTPs and primers; adding an endonuclease such as BamHI to cleave the dsDNA sequences, e.g., the RCA products, at a target site to produce a linear dsDNA; adding a recombinase (e.g., Cre recombinase) to convert the linear dsDNA to a circular Rx DNA; adding an exonuclease, e.g., T5E, to digest to degrade unligated linear dsDNA; and adding a DNA topoisomerase, e.g., DNA gyrase, to convert the circular Rx dsDNA to a circular sc dsDNA.

In one embodiment, the subject invention provides a method for synthesizing a circular double-stranded DNA molecule of a target sequence using in vitro enzymatic system of the subject invention, the method comprising:
  providing a DNA template comprising two sequence-specific recombination sites flanking the target sequence, the two sequence-specific recombination sites being selected from loxP sites, FRT sites and a combination thereof;
  performing PCR to produce a linear double-stranded DNA fragment comprising the sequence-specific recombination sites flanking the target sequence, the PCR being performed in the presence of a DNA polymerase, dNTPs and primers, preferably, selected from sequences comprising SEQ ID NO: 1 or 2;
  converting the linear double-stranded DNA fragment to a relaxed circular double-stranded DNA molecule of the target sequence, wherein converting the linear double-stranded DNA fragments to the relaxed circular double-stranded DNA molecule comprises a recombination reaction in the presence of a recombinase and a digestion reaction in the presence of an exonuclease; and
  optionally, converting the relaxed circular double-stranded DNA molecule to a supercoiled double-stranded DNA molecule, converting the relaxed circular double-stranded DNA molecule to the supercoiled double-stranded DNA molecule comprising adding a DNA topoisomerase selected from DNA gyrase or DNA topoisomerase I.

In one embodiment, the subject invention provides a method for synthesizing circular DNA via PCR, the method comprising providing DNA templates containing 2 loxP sites, preferably, the DNA templates further comprising digestion sites of, for example, Nt.BbvCI and BamHI; performing PCR to produce linear dsDNA in the presence of, for example, DNA polymerase (e.g., Taq DNA polymerase), dNTPs and primers; adding a recombinase (e.g., Cre recombinase) to convert the linear dsDNA to a circular Rx DNA; adding an exonuclease, e.g., T5E, to digest to degrade unligated linear dsDNA; and adding a DNA topoisomerase, e.g., DNA gyrase, to convert the circular Rx dsDNA to a circular sc dsDNA.

In certain embodiments, the final circular ds DNA molecules have, for example, at least 100 bp, at least 150 bp, at least 200 bp, at least 250 bp, at least 300 bp, at least 350 bp, at least 400 bp, at least 450 bp, at least 500 bp, at least 500 bp, at least 550 bp, at least 600 bp, at least 650 bp, at least 700 bp, at least 750 bp, at least 800 bp, at least 850 bp, at least 900 bp, at least 950 bp, at least 1000 bp, at least 1100 bp, at least 1200 bp, at least 1300 bp, at least 1400 bp, at least 1500 bp, at least 1600 bp, at least 1700 bp, at least 1800 bp, at least 1900 bp, at least 2000 bp, at least 2100 bp, at least 2200 bp, at least 2300 bp, at least 2400 bp, at least 2500 bp, at least 2600 bp, at least 2700 bp, at least 2800 bp, at least 2900 bp, or at least 3000 bp.

In certain embodiments, the final circular ds DNA molecules have, for example, about 100 bp to about 5000 bp, about 200 bp to about 4000 bp, about 300 bp to about 3000 bp, about 400 bp to about 3000 bp, about 400 bp to about 2000 bp, about 300 bp to about 2000 bp, about 100 bp to about 2000 bp, about 200 bp to about 3000 bp, about 100 bp to about 1500 bp, or about 100 bp to about 1000 bp.

In specific embodiments, the synthetic oligomer, RCA products, PCR products, and/or the final circular DNA molecules comprise a gene of interest or a target sequence of interest. In a preferred embodiment, the only expression elements in the final circular DNA molecule are elements to express the gene of interest or the target sequence of interest in cells, e.g., human cells and there are no bacterial DNA elements in the final circular DNA molecule. Thus, the final circular DNA molecules are suitable for use as a medicine for various applications.

In some embodiments, the gene of interest is cloned into the circular DNA template.

In one embodiment, the step of converting the rx circular DNA molecules to sc circular DNA molecules may comprise the use of DNA topoisomerase I, e.g., Variola DNA topoisomerase I, in the presence of ethidium bromide (EB); and removing EB by, for example, using phenol extraction.

Advantageously, the methods of the subject invention using RCA or PCR can synthesize circular DNA molecules comprising genes of interest at a large scale due to the amplification in RCA and PCR.

In one embodiment, the subject invention provides a kit for synthesizing oligomers having a stem-loop or hairpin structure, wherein the kit comprises a suitable container, one or more small oligomers having predetermined sequences or one or more composition comprising the small oligomers, and instructions for use in performing the synthesis of the oligomers having a stem-loop or hairpin structure.

In one embodiment, the subject invention provides a kit for synthesizing circular ssDNA molecules of the subject invention, wherein the kit comprises a suitable container, one or more synthetic oligomers having a stem-loop or hairpin structure or one or more composition comprising the synthetic oligomers, and instructions for use in performing the synthesis of the circular ssDNA molecules.

In one embodiment, the subject invention provides a kit for synthesizing double-stranded circular DNA molecules from circular ssDNA molecules of the subject invention, wherein the kit comprises a suitable container, one or more small DNA oligomers or one or more composition comprising the small DNA oligomers, circular ssDNA molecules or compositions comprising the circular ssDNA molecules, and instructions for use in performing the synthesis of the double-stranded circular DNA molecules.

In one embodiment, the kits may optionally further comprise one or more reagents, one or more labels, one or more suitable splints and enzymes, and one or more buffers. As it would be understood by those skilled in the art, additional detection or labeling methodologies may be used in the kits provided.

In one embodiment, the subject invention further provides a kit comprising a pair of DNA primers, phi29 DNA polymerase, dNTPs, a 10× buffer for phi29 DNA polymerase, a recombinase, e.g., Cre recombinase, a DNA topoisomerase (e.g., DNA gyrase and DNA topoisomerase I), 5× gyrase buffer, T5 exonuclease, T7 exonuclease, and/or lambda exonuclease, and/or optionally each primer carrying one loxP site.

In some embodiments, the kit comprises a pair of DNA primers, Taq DNA polymerase (or a thermal stable DNA polymerase), dNTPs, a 10× buffer for Taq DNA polymerase (or a thermal stable DNA polymerase), a recombinase, e.g., Cre recombinase, a topoisomerase (e.g., DNA gyrase and DNA topoisomerase I), 5× gyrase buffer, T5 exonuclease, T7 exonuclease, and/or lambda exonuclease, and/or optionally each primer carrying one loxP site.

In one embodiment, the kit comprises a DNA template comprising two sequence-specific recombination sites flanking the target sequence, DNA primers, a DNA polymerase, dNTPs, a recombinase, DNA Topoisomerase, buffers, T5 exonuclease, and an endonuclease.

This new technology provides multiple new research opportunities. First, the in vitro enzymatic system to produce Sc ds circular DNA molecules allows the design and production of novel DNA vaccines and DNA molecules for gene therapy. For example, a novel COVID-19 DNA vaccine, which only carries all necessary DNA elements for expression of S protein (or another virus protein) in human cells and does not contain any bacterial DNA sequences except a 34 bp loxP site, can be developed. Additionally, modified nucleotides can be incorporated to make the DNA vaccine more stable. Second, the new in vitro enzymatic system to produce ss circular DNA molecules provides better and inexpensive ss circular DNA as DNA donors for CRISPR/cas9 mediated genome editing for research and gene therapy. Third, PCR-based methods to produce circular DNA molecules may be developed based on the technology developed here. It will be convenient and versatile to use the PCR-based method to produce circular DNA molecules for different biomedical applications.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included.

The term "about" or "approximately" means within an acceptable error range for the particular value as determined by one of ordinary in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

As used herein, the terms "circular ss DNA," "ss circular DNA," "circular single-stranded DNA," "single-stranded circular DNA" and alike are interchangeable. The terms "circular ds DNA," "ds circular DNA," "circular double-stranded DNA," "double-stranded circular DNA" and alike are interchangeable. Similarly, the terms "rx circular ss DNA," "rx ss circular DNA," "circular rx ss DNA," "rx circular single-stranded DNA," "rx single-stranded circular DNA" and alike are interchangeable. The terms "sc circular ss DNA," "sc ss circular DNA," "circular sc ss DNA," "sc circular single-stranded DNA," "sc single-stranded circular DNA" and alike are interchangeable.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

EXAMPLES

Example 1—Generation of Rx and Sc Circular DNA Molecules by Cre Recombinase

Figure 2A:
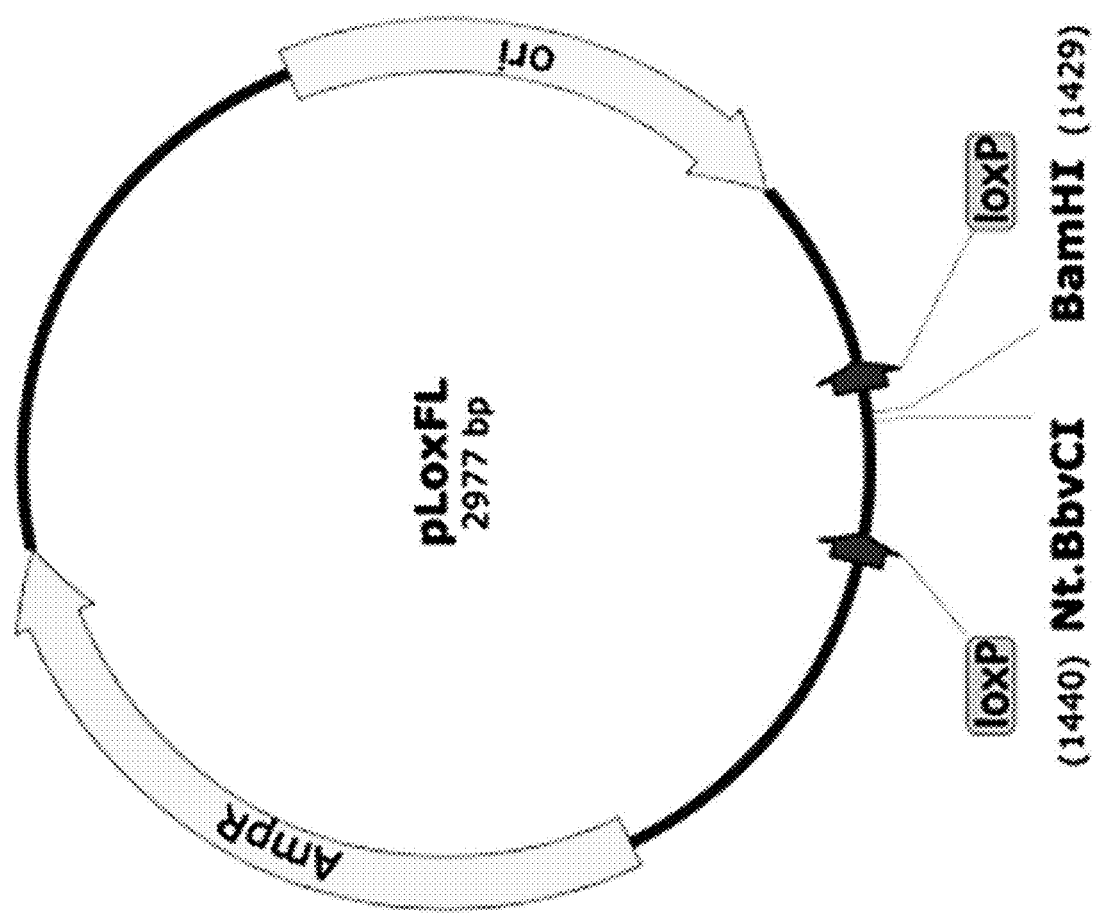
FIGS. 2A-2F show RCA of pLoxFL by phi29 DNA polymerase. 2A) plasmid pLoxFL. 2B) Sc plasmid pLoxFL was purified from *E. coli* strain Top10 carrying pLoxFL (lane 1). Lanes 2-5 represent Sc pLox2+, lambda DNA HindIII digest, the linear (Ln) fragment of pLox2+ digested by BamHI, and nicked (Nk) pLox2+ digested by Nt.BbvCI, respectively. 2C) RCA of pLoxFL by phi29 DNA polymerase. 1% agarose gel (1×TAE) of different DNA samples stained with ethidium bromide. Lane 1: lambda DNA HindIII digest; lane 2: Sc pLoxFL; lane 3: Nk pLoxFL; lane 4: RCA products of Nk pLoxFL by phi29 DNA polymerase; lane 5: BamHI digestion of the RCA product. 2D-2F) An experimental procedure to synthesize plasmid pLoxFL_a using the in vitro method. Symbols: Sc, supercoiled; Rx, relaxed.
Figure 2C:
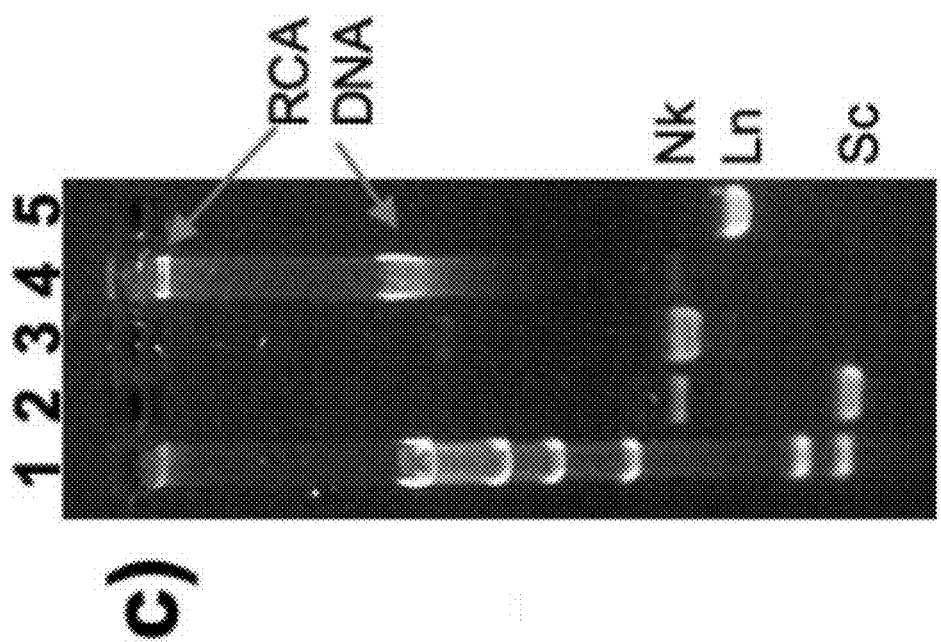
Figure 2B:
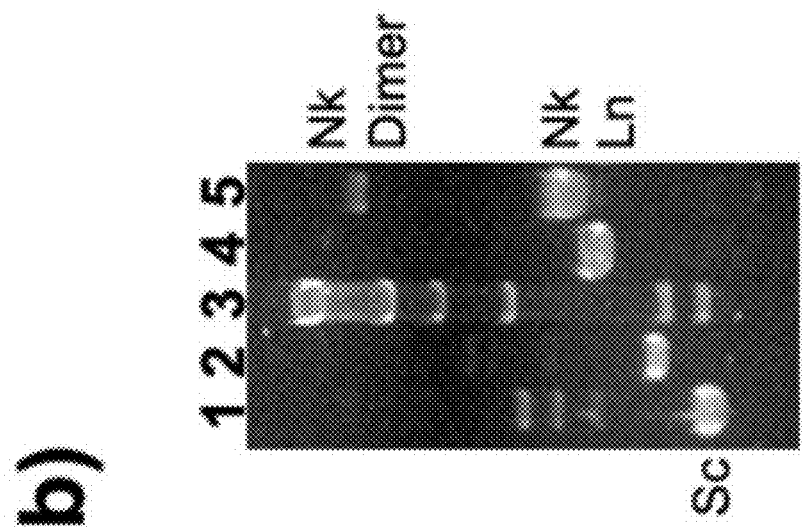
Figure 2D:
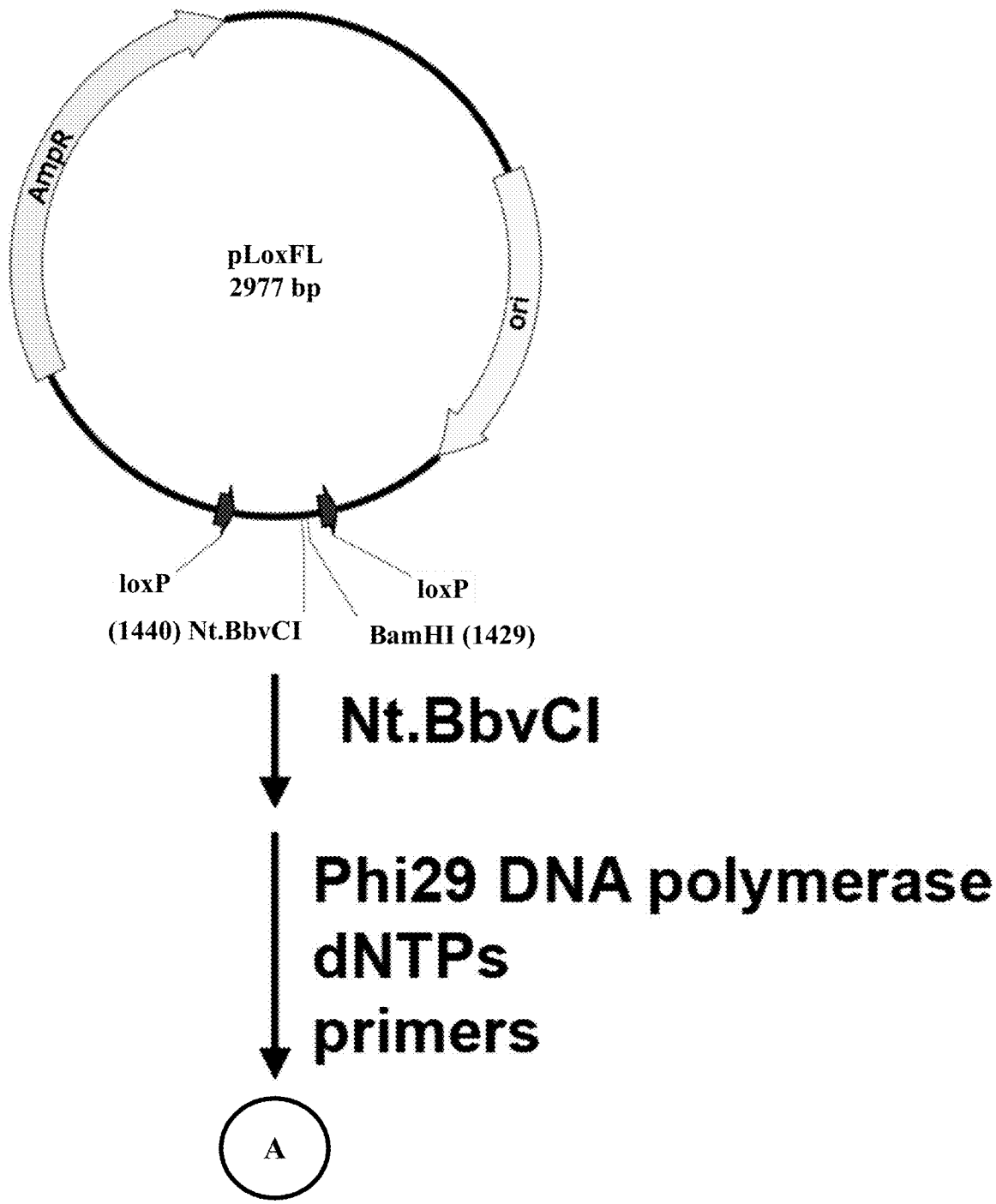
Figure 2E:
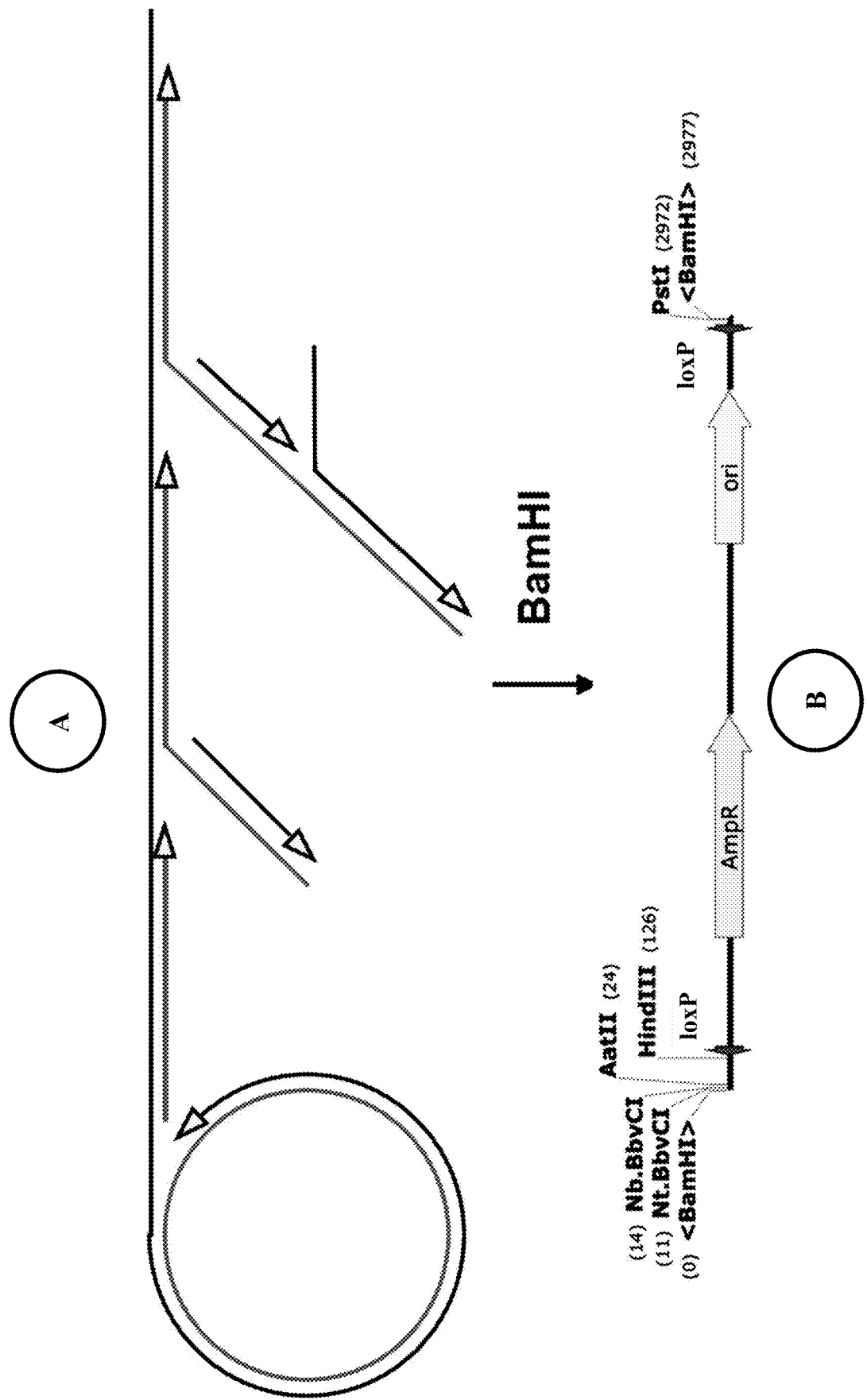
Figure 2F:
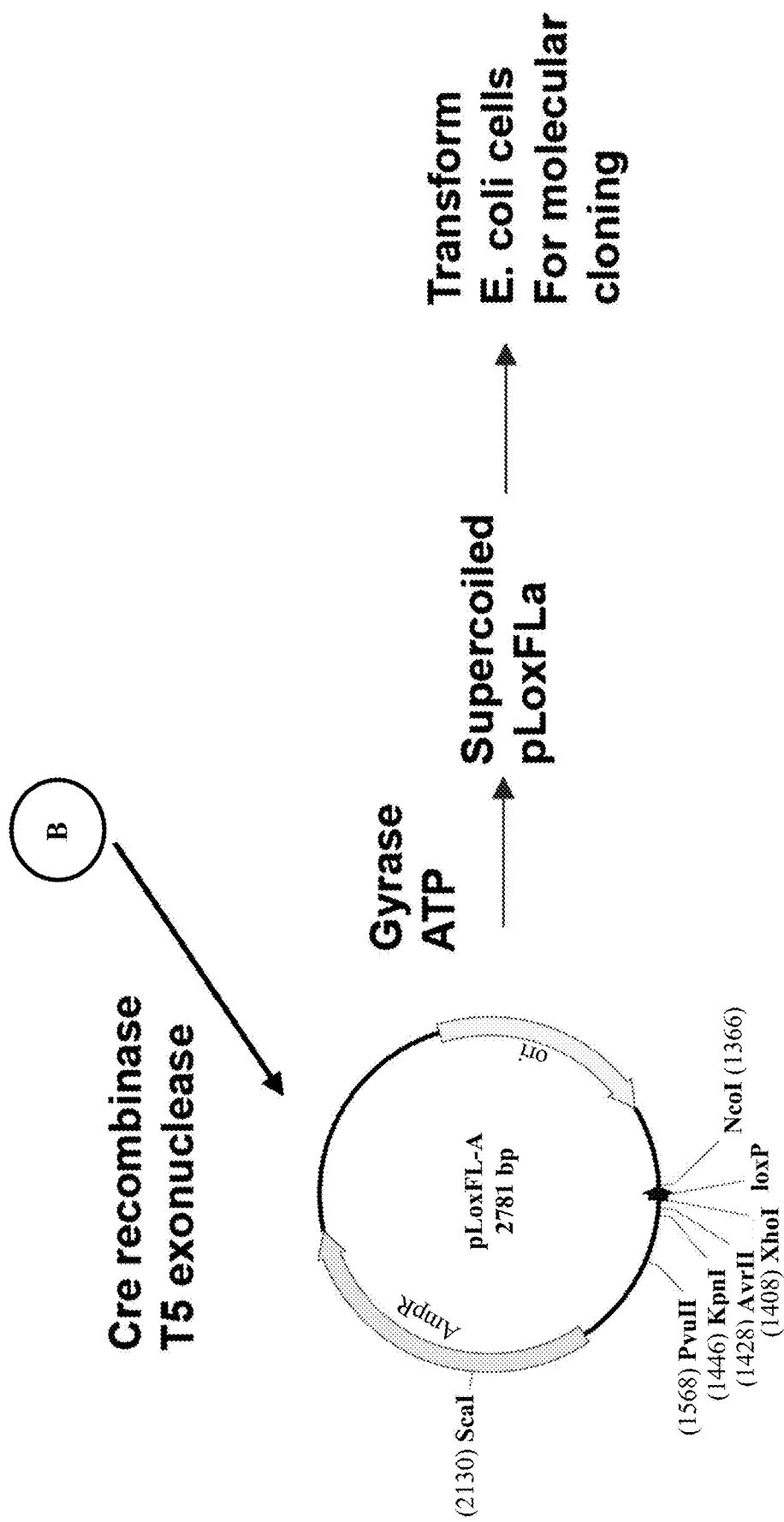

Plasmid pLoxFL was constructed by inserting a 29 bp synthetic oligomer carrying BamHI and Nt.BbvCI sites into the PstI and AatII sites of pLOX2+. In additional to two loxP sites in the same direction, pLoxFL also contains a single BamHI and Nt.BbvCI site (FIGS. 2A and 2D-2F). Digestion of pLoxFL with BamHI and Nt.BbvCI yields a linear and a nicked (Nk) pLoxFL, respectively (FIG. 2B).

Rolling circle amplification (RCA) of pLoxFL by phi29 DNA polymerase. 30 ng of Nk pLoxFL was amplified in 50 μL of 1×phi29 DNA polymerase buffer using 10 units of phi29 DNA polymerase (NEB, M0269S), 0.5 mM of dNTPs, and 2 μM of 2 primers (FL1038: 5'-GGTGTCGGATC-CATGCTGCA-3' (SEQ ID NO: 1); FL1041: 5'-AAATAGGCGTATCACGAGGC-3' (SEQ ID NO: 2)) at 30° C. overnight (~15 hours) to generate ~10 μg of high molecular weight of dsDNA (FIG. 2C, lane 4). Digestion of the high molecular weight DNA molecules with BamHI produced a linear 2.9 kb DNA fragment (pLoxFL BamHI digest; FIG. 2C, lane 5).

To generate Rx and Sc circular DNA molecules by Cre recombinase, Cre recombinase was expressed and purified. Using the purified Cre recombinase, the linear DNA fragment carrying two loxP sites (pLoxFL BamHI digest, lane 2 of FIG. 3) was converted into Rx circular DNA molecules (lanes 3, 4, 7, and 8 of FIG. 3). The recombination efficiency was ~74%.

Two methods were used to generate Sc DNA molecules. In method one, 25 μM of ethidium bromide (EB) was added to the recombination mixture. After T5 exonuclease digestion and phenol extraction, Sc DNA molecules were obtained (compare lanes 3-6 of FIG. 3). Nevertheless, the results showed that EB greatly inhibited the recombination efficiency and T5 exonuclease.

Figure 3:
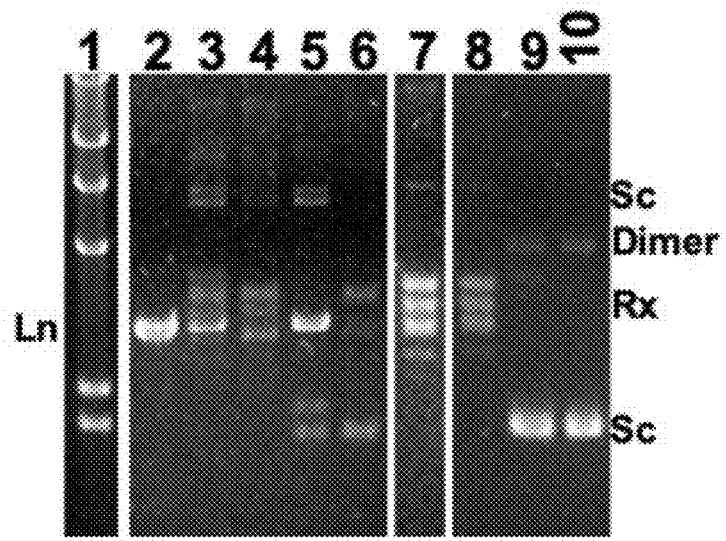
FIG. 3 shows relaxed (Rx) and Sc circular DNA molecules produced by recombination using Cre DNA recombinase. Recombination reactions were performed in 20 μl, of 1× recombination buffer with 250 ng of pLoxFL BamHI digest and 73 nM of Cre recombinase at 37° C. for 30 min. Lane 1. 1 DNA HindIII digest; lane 2, RCA product BamHI digest; lanes 3-6 and 9-10, recombination products by Cre recombinase; lanes 3 and 5, without T5 exonuclease; lanes 4 and 6, T5 exonuclease was added; lanes 5-6, EB was added; lanes 7-8, Purified Rx DNA; Lanes 9-10, Sc DNA by *E. coli* gyrase; lane 10, T5 exonuclease was added.

In method two, Rx circular DNA molecules were purified after recombination reaction and T5 exonuclease digestion (lanes 7 and 8 of FIG. 3). *E. coli* DNA gyrase efficiently converted Rx circular DNA molecules into Sc circular DNA molecules (compare lanes 9 and 10 to lanes 7 and 8 of FIG. 3). T5 exonuclease completely removed a small amount Nk DNA (compare lanes 9 and 10 of FIG. 3). The final product also contains a small amount of Sc circular DNA dimers (lanes 9 and 10 of FIG. 3).

Figure 4:
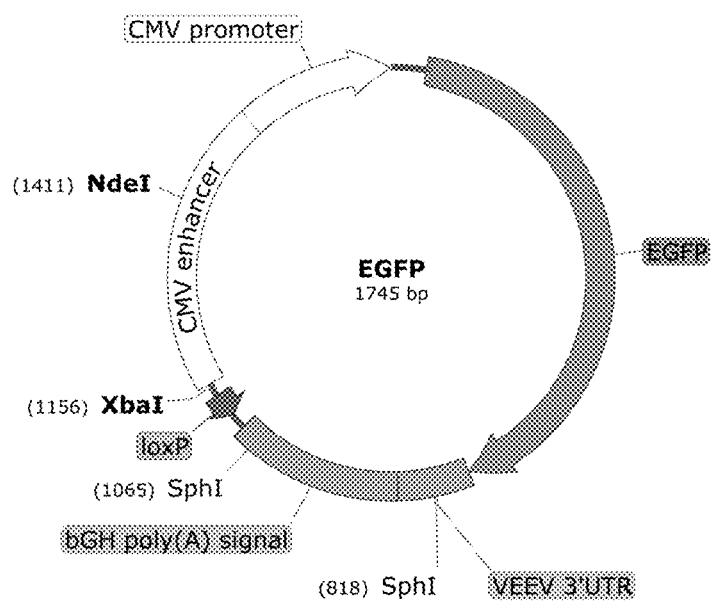
FIG. 4 shows a map of circular EGFP.

Example 2—a Scalable In Vitro Enzymatic System to Synthesize Relaxed and Supercoiled Double-Stranded Circular DNA Molecules To develop a scalable in vitro enzymatic system and produce large quantities of Sc circular DNA molecules, such as EGFP (FIG. 4), three milestones can be achieved: milestone 1, to produce 100 µg; milestone 2, 5 mg; and milestone 3, 50 mg of Sc EGFP.

First, a ss circular DNA template is constructed using synthetic DNA oligomers through ligation by T4 DNA ligase with the help of DNA splints for RCA. T7 exonuclease and/or lambda exonuclease is used to remove unligated oligomers and DNA splints. Rolling circle DNA amplification is performed with two primers and phi29 DNA polymerase to produce large amounts of high molecular weight dsDNA molecules. Linear dsDNA molecules carrying two loxP sites in the same direction are produced by digesting the RCA products using BamHI. Cre DNA recombinase is used to convert the linear DNA molecules to Rx circular DNA molecules. After T5 exonuclease removes unwanted DNA molecules, Rx DNA molecules are produced. *E. coli* DNA gyrase is used to convert Rx DNA molecules to Sc DNA molecules.

Figure 5:
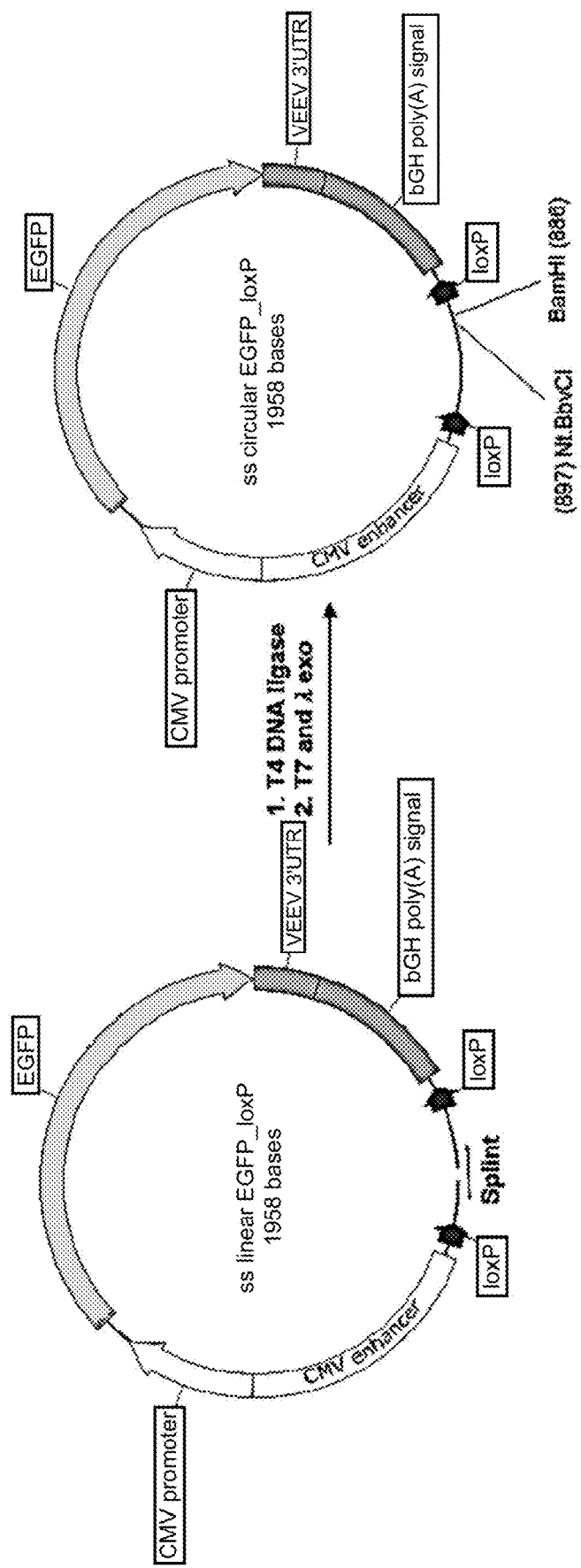
FIG. 5 shows that single-stranded circular DNA template EGFP_loxP is produced by a ligation reaction using T4 DNA ligase with the help of splint oligomers. T7 and lambda exonuclease (T7 and λexo) are used to remove unligated ss linear DNA and splints.
Figure 6:
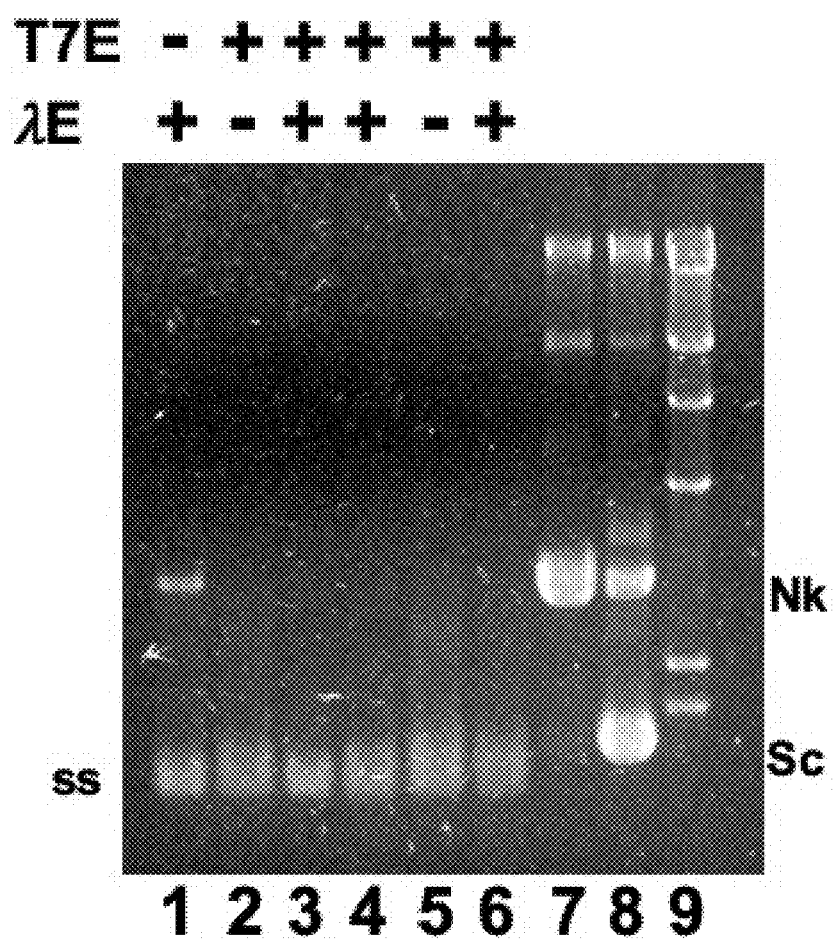
FIG. 6 shows that T7 (T7E) and lambda exonuclease (XE) efficiently degrade ss linear DNA and do not digest ss circular DNA. 0.5 μg of Nk pAB1 and 50 nM of T7 and/or lambda exonuclease were used. DNA samples were analyzed by 1% agarose gel. Lanes 1 and 4 used lambda exonuclease buffer (NEB). Lanes 2, 4, 5 and 6 used NEB buffer 4. Lanes 1~4 were incubated at 37° C. and lanes 5 and 6 were incubated at 25° C. Lane 7 and 8 are Nt BbvCI nicked pAB1 and Sc pAB1, respectively. Lane 9, λ DNA HindIII digest.

To synthesize sufficient amounts of ssDNA template EGFP_loxP (FIG. 5) for RCA reactions, 5'-end phosphorylated synthetic oligomers are ligated with the help of splints (short bridging DNA oligonucleotides complementary to the 5'-end of one oligomer and 3'-end of another oligomer) by T4 DNA ligase. After the ligation reaction, T7 and lambda exonuclease are used to digest unligated oligomers and the splints to yield ss circular DNA templates (FIG. 5) because these two exonucleases can efficiently digest ss linear DNA oligomers and, however, do not degrade ss circular DNA molecules (FIG. 6). The ss circular DNA template is purified and concentrated by isopropanol precipitation and dialyzed against 10 mM Tris-HCl buffer (pH 8).

To produce ss circular DNA template eGFP_loxP, ~20 synthetic oligomers with an average length of ~100 nt are needed. Another 20 splint oligomers are also needed for the ligation reactions. Alternatively, to reduce the cost, classical cloning and biochemical techniques can be used. Circular EGFP_lox_FTR can be constructed using the method shown in FIG. 7.

Figure 7:
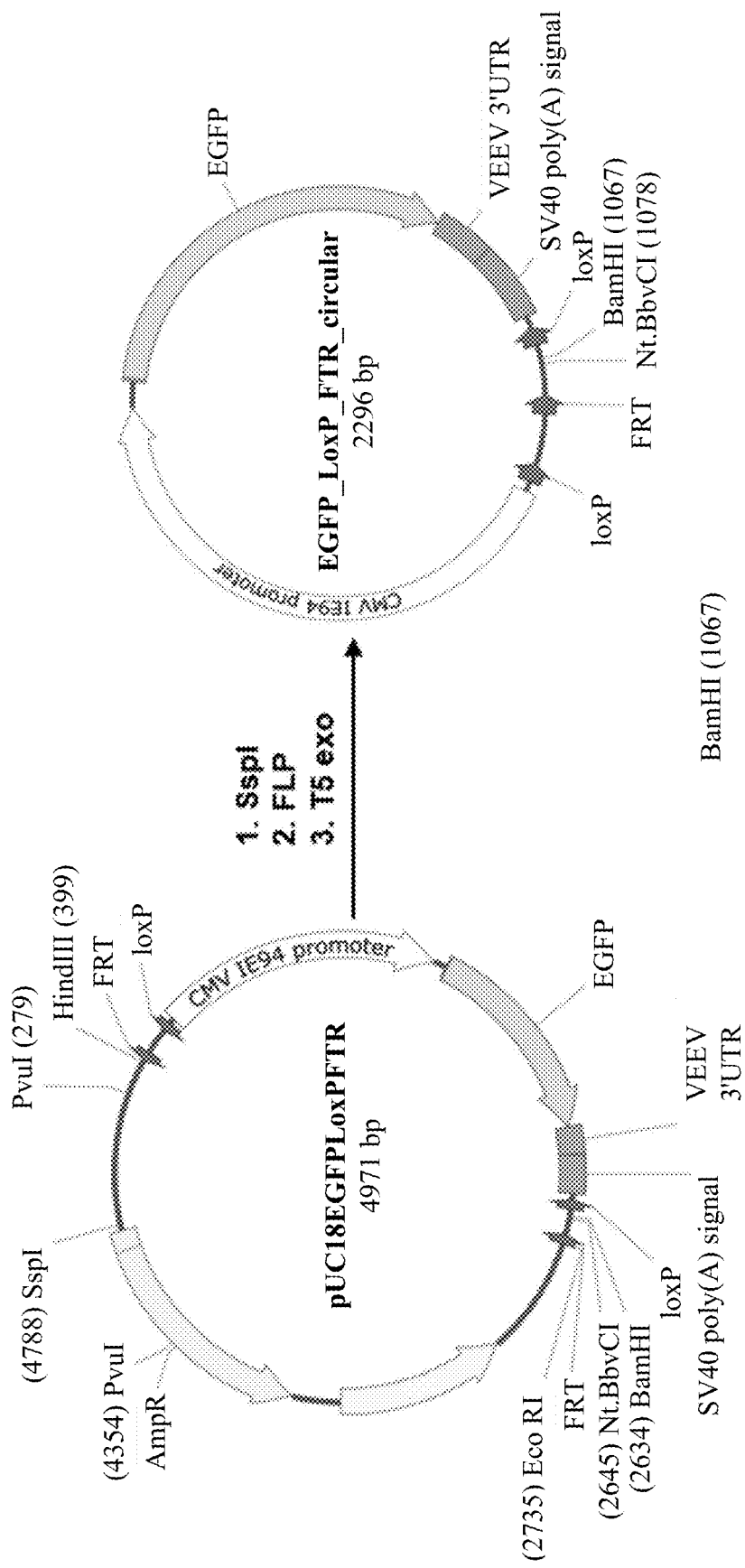
FIG. 7 shows plasmid pUC18_EGFP_Lox_FTR used to generate circular EGFP_loxP_FTR DNA template for RCA reactions.

First, a 2 kb DNA fragment carrying all DNA elements including a pair of loxP sites and FRT sites in the same direction is cloned between EcoRI and HindIII sites of pUC18 to yield plasmid pUC18_EGFP_lox_FTR. Nicking endonuclease Nt.BbvCI site is included. Plasmid pUC18_EGFP_lox_FTR can be purified from a transformed *E. coli* strain and linearized by restriction enzyme SspI. FLP recombinase is expressed and purified and used to convert linear DNA fragment to circular EGFP_loxP_FTR (FIG. 7).

After T5 exonuclease removes unwanted DNA molecules, circular EGFP_loxP is produced and used for RCA reactions after nicked by Nt. BbvCI. Alternatively, EGFP_loxPFTR can be produced by in vivo FLP-FRT recombination.

Figure 8:
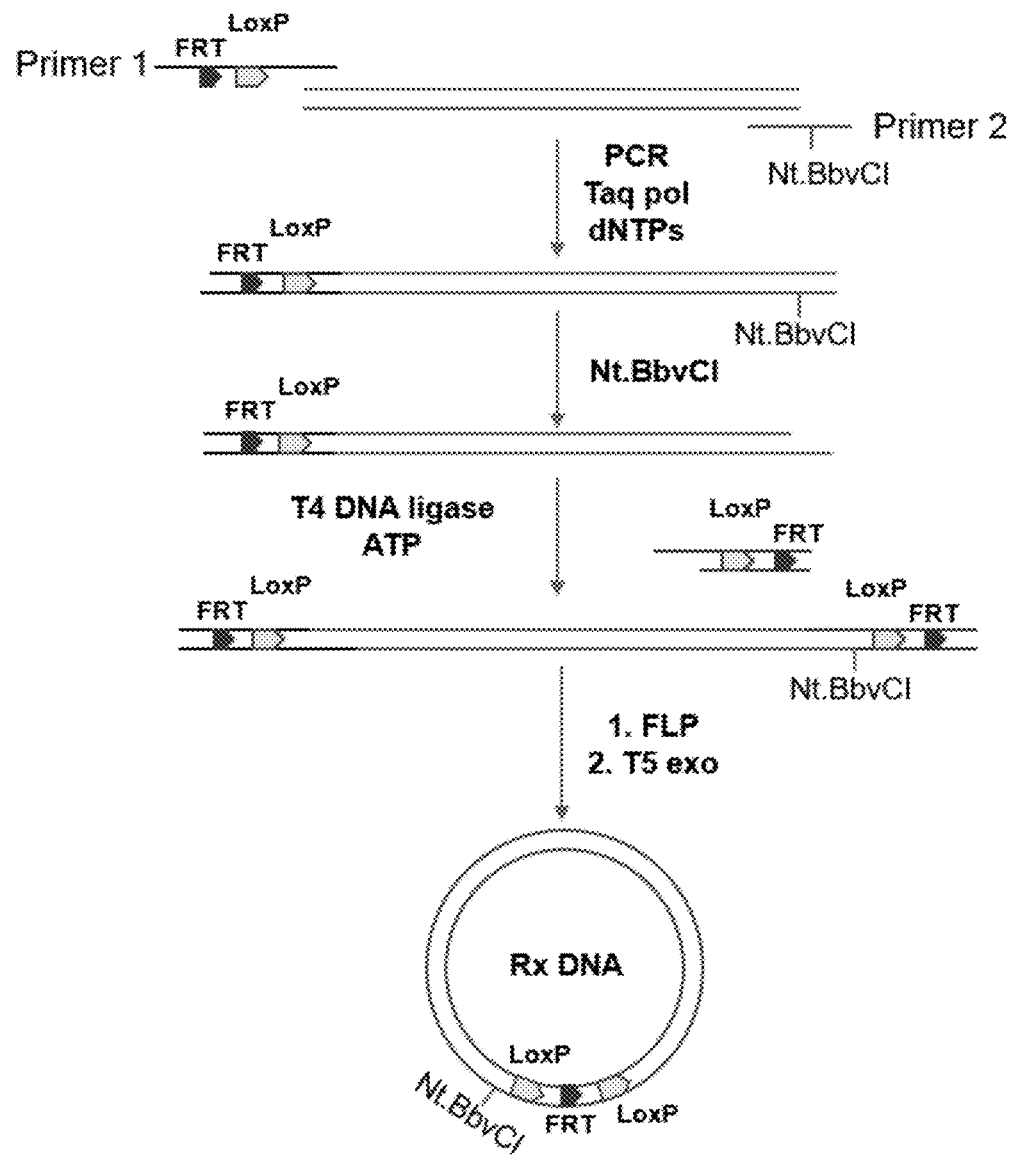
FIG. 8 shows the synthesis of a template for RCA reaction by phi29 DNA polymerase.
Figure 9:
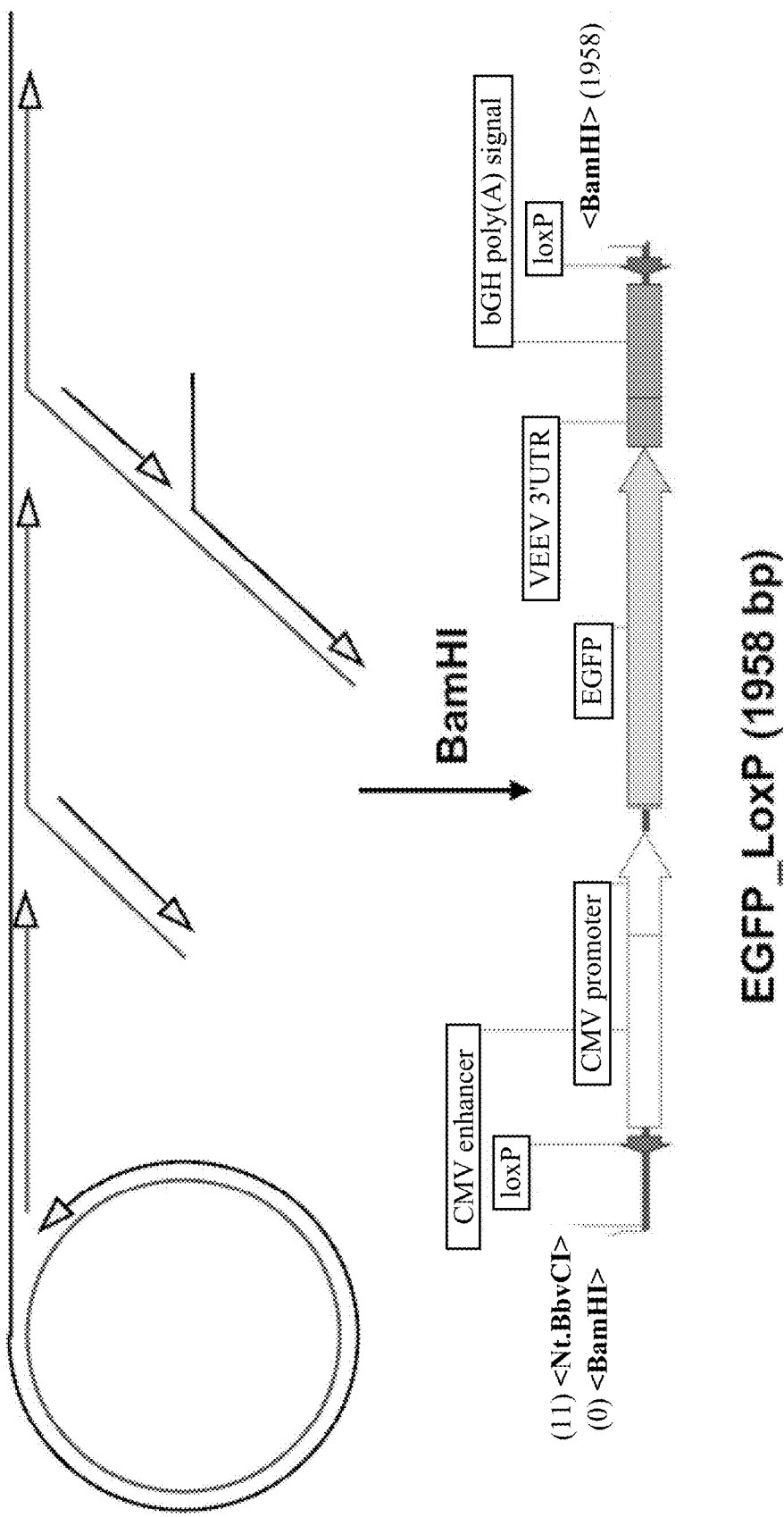
FIG. 9 shows rolling circle amplification of EGFP_loxP by phi29 DNA polymerase. Linear DNA is produced by BamHI digestion.

To produce a large amount of DNA molecules using rolling circle amplification by phi29 DNA polymerase (FIG. 9), the high molecular weight DNA molecules are digested by BamHI to yield linear DNA fragments, such as 2.2 kb EGFP_LoxP (FIG. 9). FIG. 8 shows the synthesis of a template for RCA reaction by phi29 DNA polymerase.

The phi29 DNA polymerase can be expressed and purified. The phi29 DNA polymerase gene has been cloned to plasmid pET28a(+). A His-tag and a TEV proteinase site are linked to the N-terminal of phi29 DNA polymerase. The His-tagged phi29 DNA polymerase can be purified using a Ni-NTA column in the presence of high salt concentration to remove host DNA. T5 exonuclease can also be used to remove host DNA. A SP-Sepharose FF column can be employed to purify phi29 DNA polymerase. If needed, phi29 DNA polymerase can be further purified by using FPLC. His-tag can be removed by TEV protease. To linearize the RCA products, restriction enzymes, such as BamHI, EcoRI, and HindIII are used.

Figure 10A:
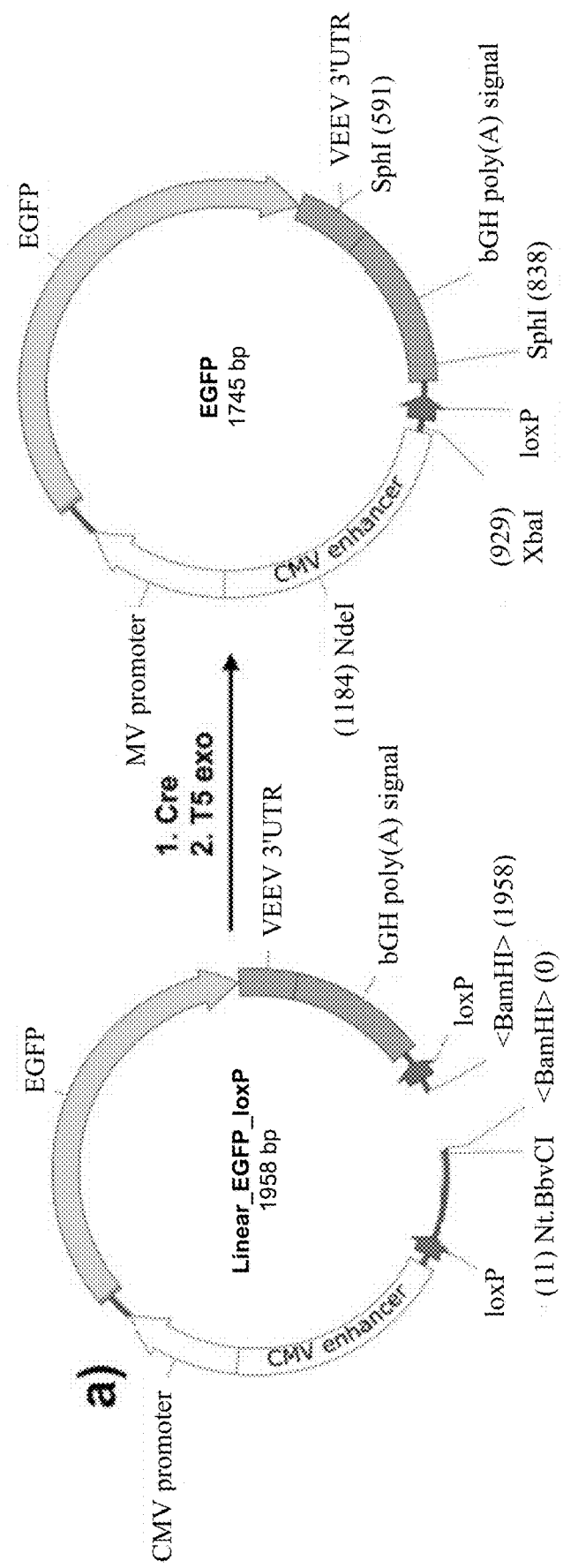
FIGS. 10A-10B show the production of Rx and Sc EGFP DNA molecules. 10A) Linear DNA fragments carrying two loxP sites (the RCA products) are converted to circular DNA molecules (EGFP) by Cre recombinase (Cre). T5 exonuclease can remove unreacted linear DNA molecules. 10B) Negatively supercoiled DNA Relaxed can be generated by *E. coli* DNA gyrase (method 1) or variola DNA topoisomerase I in the presence of ethidium bromide (method 2). For method 2, phenol extraction can remove ethidium bromide from the reaction mixtures.
Figure 10B:
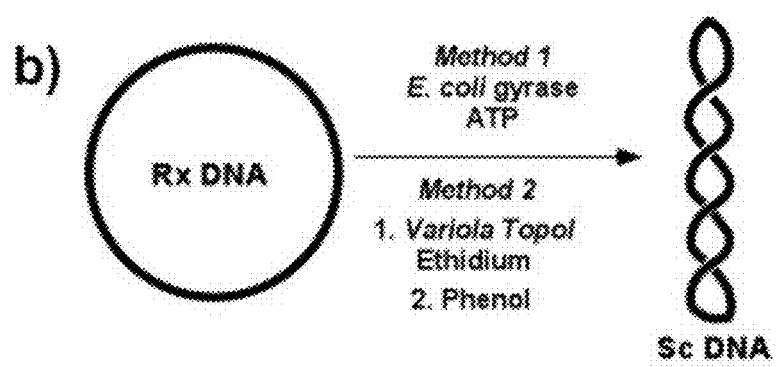

FIGS. 10A-10B show the strategy to produce Rx and Sc EGFP DNA molecules. Linearized RCA products are circularized and converted to Rx DNA EGFP by Cre recombinase. Because the recombination efficiency by Cre recombinase is high (FIG. 3), the majority of the linearized RCA products are expected to be converted to Rx circular DNA molecules. T5 exonuclease is used to digest unreacted linear DNA molecules. *E. coli* DNA gyrase is used to convert the Rx DNA molecules to Sc DNA molecules in the presence of ATP (FIG. 10B, Method 1). DNA sequencing is used to confirm the identity of Sc EGFP. Human Hela cells and A431 cells are transfected using Sc EGFP and EGFP expression can be detected by using a fluorescence microscope.

Moreover, Sc DNA can be generated using a eukaryotic DNA topoisomerase I, such as variola DNA topoisomerase I, in the presence of ethidium bromide (FIG. 10B, Method 2). Rx DNA can be temporarily (+) supercoiled by DNA intercalator ethidium bromide. Variola DNA topoisomerase I can relax the temporarily (+) Sc DNA. After phenol extraction to remove ethidium bromide, (−) Sc DNA is produced. The expression and purification of variola DNA to topoisomerase I or vaccinia DNA topoisomerase I (a closely related topoisomerase) in *E. coli* are straightforward. Variola DNA topoisomerase I (314 aa residues and ~36.6 kDa) is very active and robust. Further, a chromatographic method, such as DEAE chromatography, may be developed to concentrate and purify the recombination products.

Figure 11:
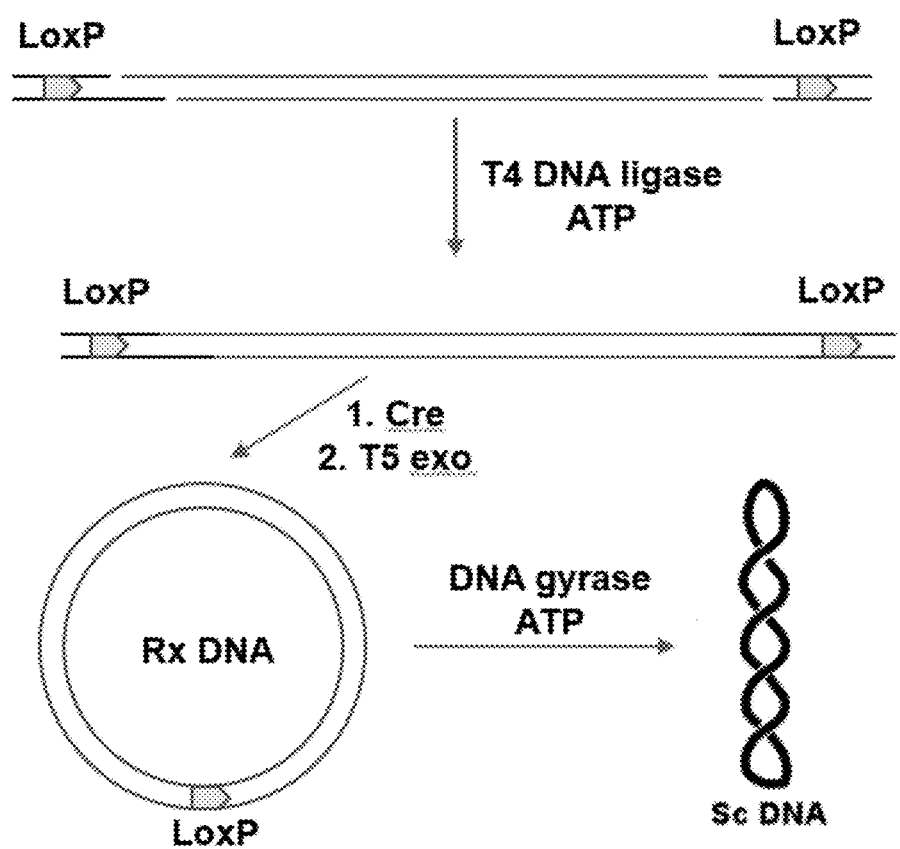
FIG. 11 shows the synthesis of double-stranded circular DNA from synthetic oligomers or linear DNA from other sources (PCR or RCA products).

FIG. 11 shows the synthesis of double-stranded circular DNA from synthetic oligomers or linear DNA from other sources (PCR or RCA products). The synthesis comprises the following steps:

Step 1. 5'-phorsphated oligomers are annealed to double-stranded DNA molecules. The linear DNA molecules can be produced by PCR or RCA;

Step 2. Ligation reactions are performed to produce the long linear double-stranded DNA molecules. T4 DNA ligase may be used;

Step 3. Two double-stranded oligomers carrying a loxP sites are ligated to the linear double-stranded DNA molecules by T4 DNA ligase. Hairpins carrying loxP sites can be used;

Step 4. Cre recombinase converts the linear double-stranded DNA molecules to relaxed circular DNA molecules;

Step 5. T5 exonuclease is added to degrade unligated linear DNA molecules; and

Step 6. DNA gyrase converts relaxed double-stranded DNA molecules to supercoiled double-stranded DNA molecules.

Figure 12A:
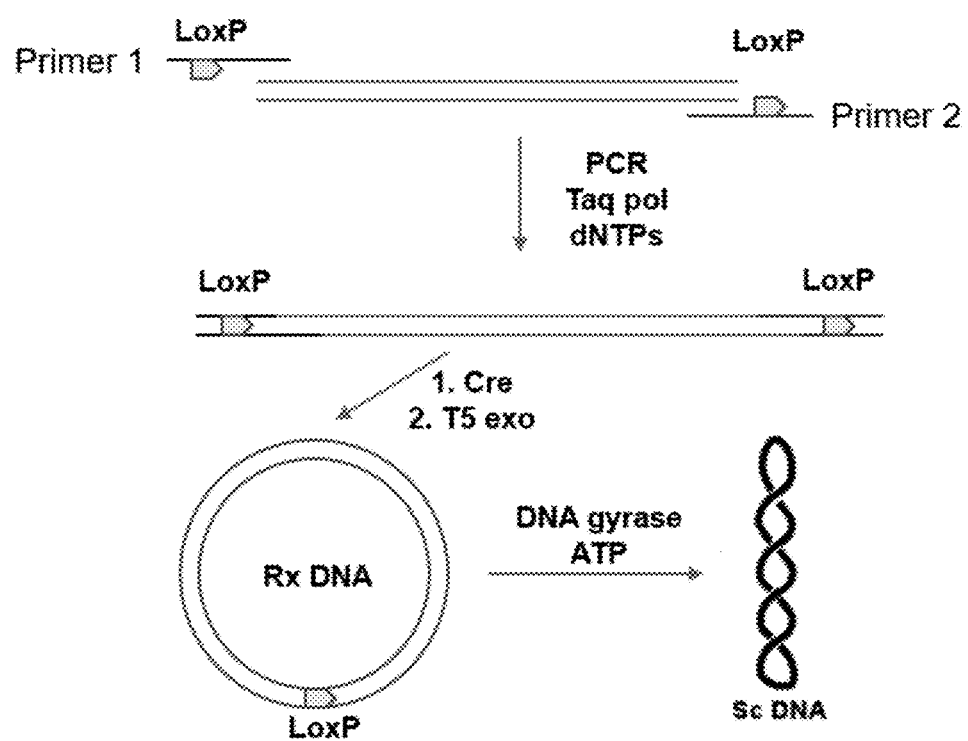
FIGS. 12A-12B show the synthesis of double-stranded circular DNA using PCR products. 12A) PCR reactions using two primers each carrying a loxP site are performed. 12B) two primers are used, in which one primer contains a loxP site and another primer carries a nicking endonuclease recognition site.
Figure 12B:
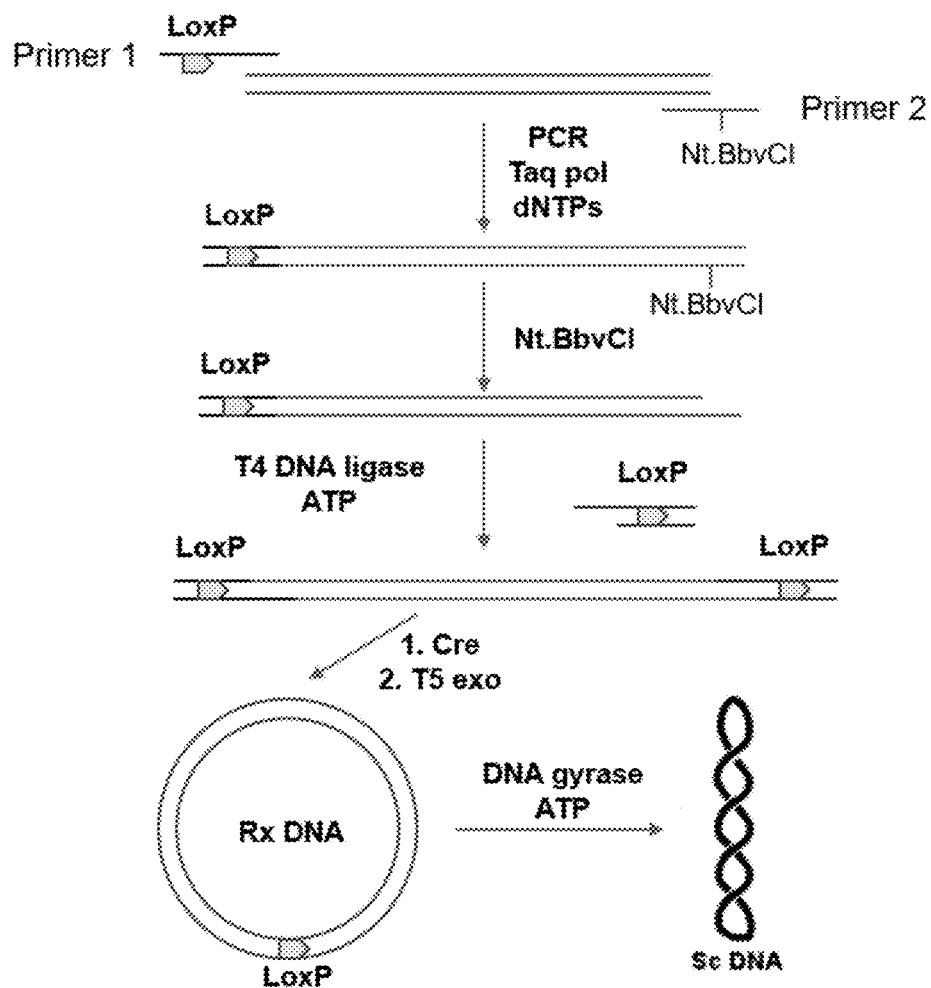

FIGS. 12A-12B show the synthesis of double-stranded circular DNA using PCR products, which comprises the following steps:

Step 1. PCR reactions using two primers each carrying a loxP site are performed. Because the 34 bp loxP site is AT-rich, proper primers can be designed. Alternatively, loxP mutants may be used for different primers. Further, two primers may be used, in which one primer contains a loxP site and another primer carries a nicking endonuclease recognition site. PCR products are digested by nicking enzyme. An oligomer carrying a loxP site is annealed and ligated to the PCR product;

Step 2. Cre recombinase converts the linear double-stranded DNA molecules to relaxed circular DNA molecules;

Step 3. T5 exonuclease is added to degrade unligated linear DNA molecules; and

Step 4. DNA gyrase converts relaxed double-stranded DNA molecules to supercoiled double-stranded DNA molecules.

Figure 13:
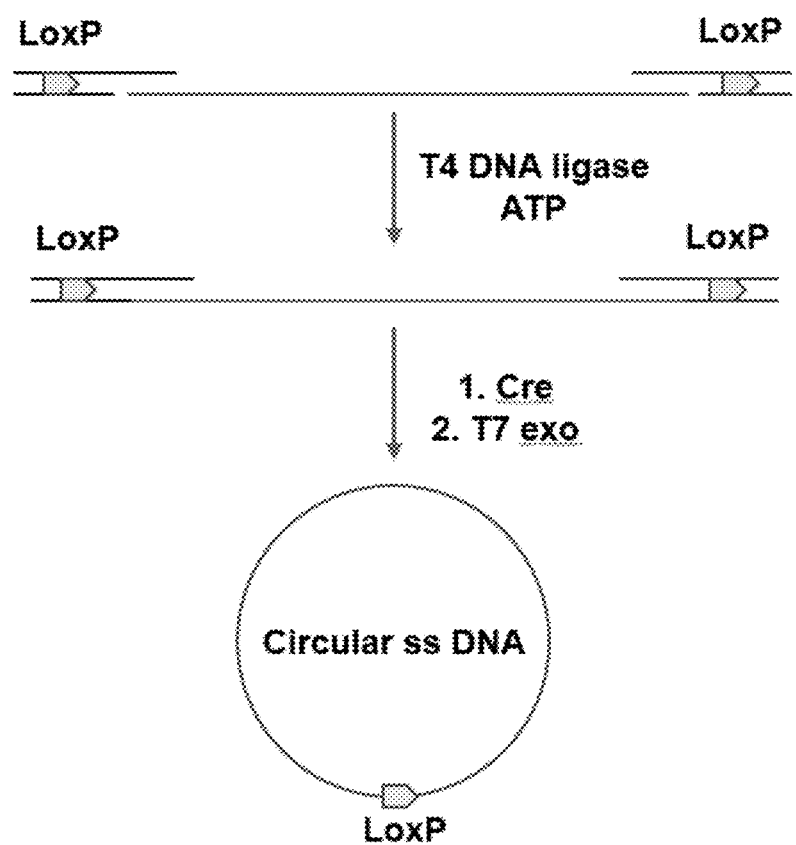
FIG. 13 shows the synthesis of single-stranded circular DNA from synthetic oligomers.

Example 3—a Scalable In Vitro Enzymatic System to Synthesize Circular ssDNA Molecules Single-stranded circular DNA templates are synthesized as noted above. For example, single-stranded circular DNA can be synthesized from synthetic oligomers (FIG. 13) by the following steps:

Step 1. Ligation reactions are performed to produce the long linear single-stranded DNA molecules using 5-phosporlated oligomers with the help of splints. T4 DNA ligase may be used. The linear DNA molecules can be produced by PCR or RCA;

Step 2. Two double-stranded oligomers (or hairpins) carrying a loxP sites are ligated to the linear double-stranded DNA molecules by T4 DNA ligase;

Step 3. Cre recombinase converts the linear single-stranded DNA molecules to single-stranded circular DNA molecules; and Step 4. T5 exonuclease is added to degrade unligated linear DNA molecules.

In the presence of one DNA primer, a large amount of ssDNA molecules is produced by RCA using phi29 DNA polymerase and the ss DNA template. Two synthetic oligomers will be annealed to the newly synthesized ss DNA molecules. One synthetic oligomer contains a DNA sequence complementary to a restriction enzyme recognition site, such as BamHI site. The second synthetic oligomer carries a DNA sequence complementary to the two loxP sites. Linear single-stranded DNA molecules carrying two loxP sites in the same direction are produced by digesting the RCA products using BamHI. Cre DNA recombinase is used to convert the linear DNA molecules to ss circular DNA molecules. After T7 exonuclease and/or lambda exonuclease digest unwanted DNA molecules, ss circular DNA molecules are generated.

Figure 14:
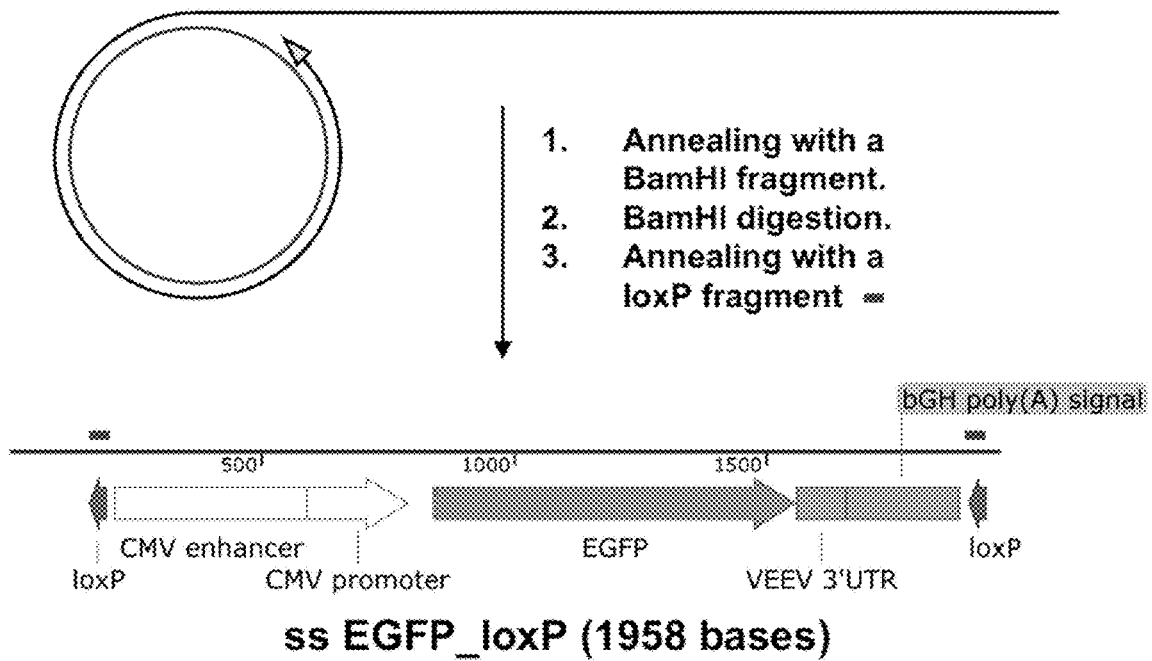
FIG. 14 shows RCA by phi29 DNA polymerase in the presence of one primer to produce high molecular weight ss DNA molecules. With the help of one oligomer to form a BamHI site, BamHI can convert the high molecular weight RCA products to 2262 nt. Linear ss DNA. Another oligomer complementary to the loxP sequence can be annealed. Two loxP sites are formed.

RCA reactions by phi29 DNA polymerase are used in the presence of only one primer to produce a large amount of ss DNA molecules (FIG. 14). After the RCA reactions, an oligomer containing a DNA sequence complementary to the unique BamHI site, anneals to the ss RCA products. BamHI is used to linearize the RCA products (FIG. 14) and produce a 1,958 nt. linear SS DNA molecule (ss EGFP_loxP). nicer another oligomer complementary to the loxP sequences is annealed to the EGFP_loxP sequences, two loxP sites are formed.

Figure 15:
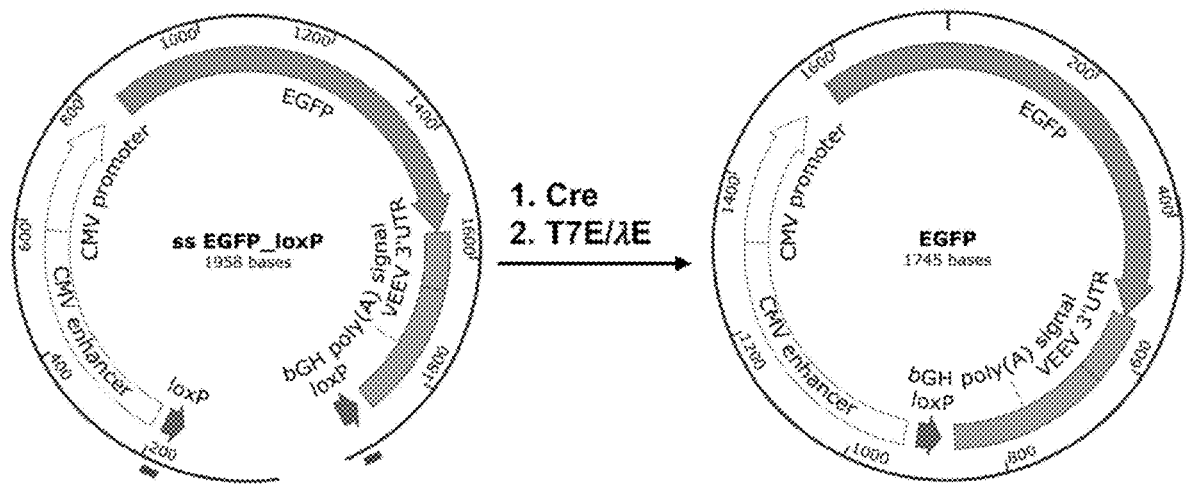
FIG. 15 shows recombination reactions to generate ss circular DNA molecules, e.g., ssEGFP.

To generate ss circular DNA molecules through recombination by Cre recombinase (FIG. 15), after the recombination reaction, T7 and lambda exonuclease are used to remove unwanted linear DNA molecules. The ss circular DNA molecules are concentrated using isopropanol precipitation and dialyze against 10 mM Tris-HCl buffer. The final products are sequenced to confirm the identity of ss EGFP.

Example 4—Synthesizing Circular ssDNA Molecules

To synthesize the circular ssDNA molecule, the two oligomers are annealed (FIG. 16A) to form the stem-loop or hairpin structure with certain experimental conditions: low concentrations of oligomer, low ionic concentration (for example, 10 mM Tris-HCl, pH 8 or 10 mM Tris-HCl and 1 mM NaCl), and optionally, in the presence of PEG20,000 or PVA20,000. Then, 1 mM of DTT, 1 mM ATP, and 10 mM MgCl2 or MgAC2 are added to the solution. Next, T4 DNA ligase is added to initiate the ligation reaction. Further, the un-ligated oligomers can be removed by adding $E.\ coli$ exonuclease I and/or III. The final closed circular single-stranded DNA can be precipitated by adding isopropanol, washed by 70% ethanol, and dialyzed against a buffer, such as 10 mM Tris-HCl in 4° C.

Figure 18A:
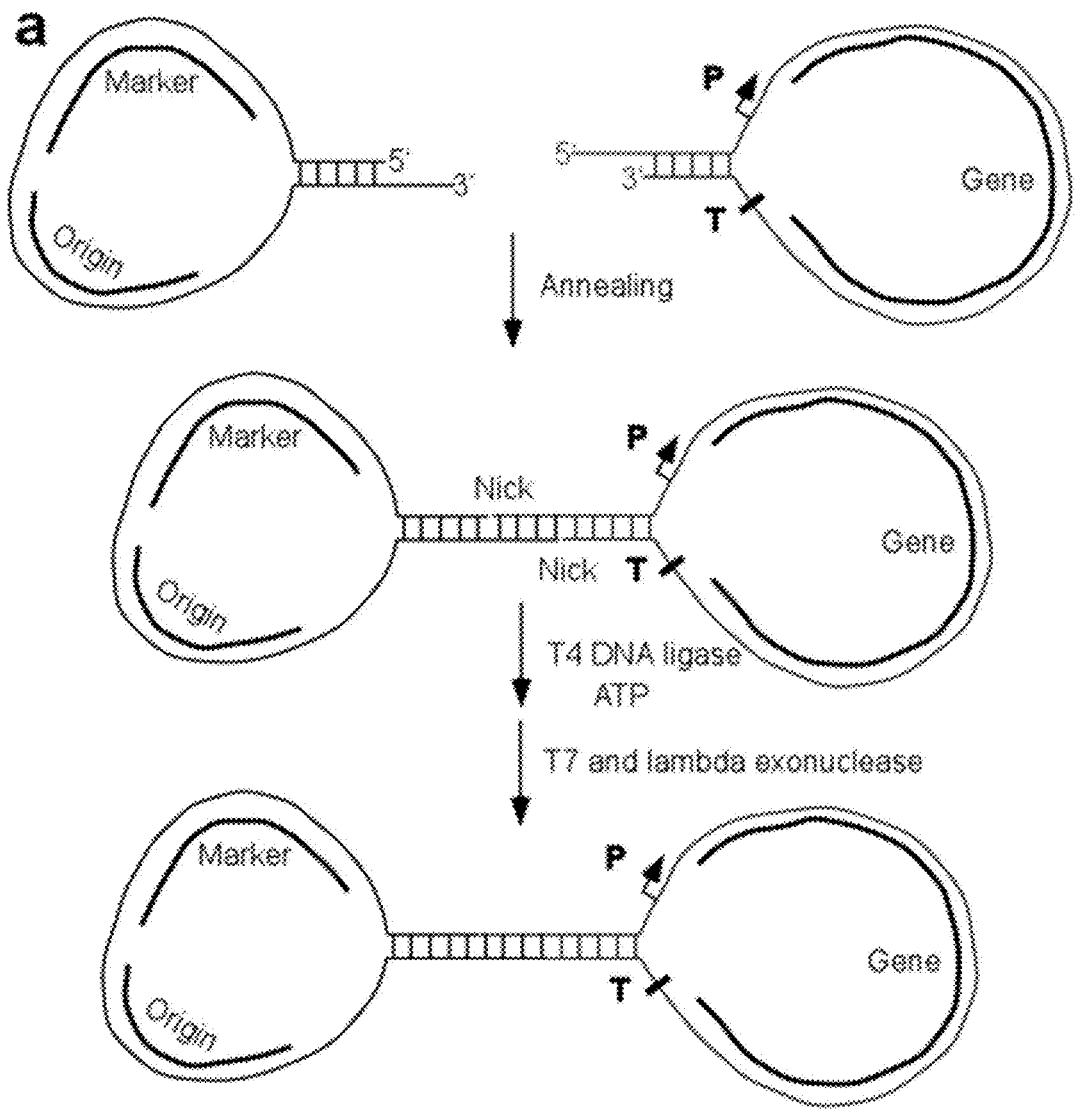
FIGS. 18A-18B show experimental strategies to construct single-stranded circular DNA molecules. 18A) An experimental strategy to construct single-stranded circular DNA molecules for cloning and expressing proteins. Symbols: Origin, DNA replication origin; Marker, selection marker; P, promoter; and T, transcription terminator. 18B) An experimental strategy to construct a single-stranded DNA molecule to express GFP in BL21(DE3). Symbols: ColE1, ColE1 DNA replication origin; Amp, ampicillin resistance gene; T7P, T7 promoter; and T7T, T7 transcription terminator.

FIG. 18A shows an example. Only in vitro ligation reactions are needed. A design is to prepare a stem-loop or hairpin structure containing a DNA replication origin and a selection marker and another stem-loop or hairpin structure carrying the genes, which will be cloned or/and expressed, and a promoter and transcription terminator. After annealing and ligation, a closed single-stranded circular DNA molecule is constructed and can be used to transform an organism, such as $E.\ coli$ cells.

Alternatively, various DNA fragments/elements can be ligated into to a stem-loop or hairpin structure and then ligate with a short stem-loop or hairpin structure to make a closed single-stranded circular DNA molecule.

Figure 18B:
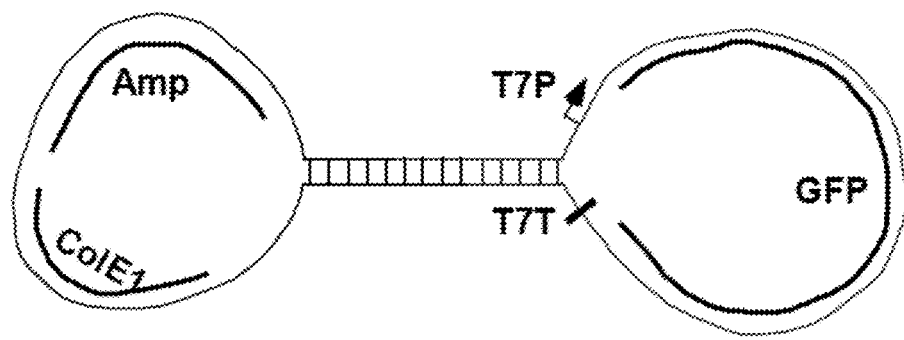

FIG. 18B shows the construction of a closed single-stranded circular DNA molecule harboring a ColE1 replication origin (from plasmid pBR322), an ampicillin resistance gene (from plasmid nB12127) and a GFP gene under the control of T7 promoter and terminator $E.\ coli$ strain DH5α and BL21(DE3) can be transformed by this DNA molecule. Green fluorescence protein is overexpressed after adding IPTG or Isopropyl β-D-1-thiogalactopyranoside to BL21(DE3) carrying this DNA molecule.

Figure 19:
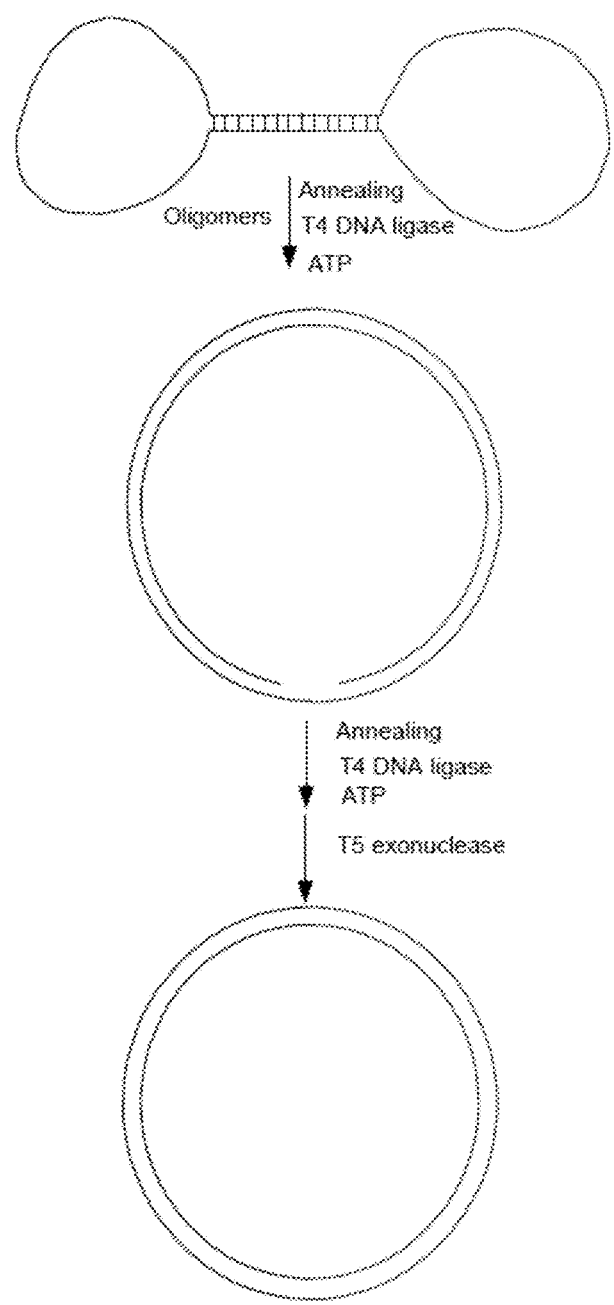
FIG. 19 shows an experimental strategy to construct double-stranded circular DNA molecule from a single-stranded circular DNA molecule.

Double-stranded circular DNA molecules can further be constructed from single-stranded circular DNA molecules (FIG. 19).

All synthesis can scale up to the milligram range. Agarose gel or PAGE gel should not be used to purify the DNA products. Crowding agents, such as PEG 20,000 or PVA 20,000, may be used.

Example 5—Synthesizing Additional Circular DNA Molecules

Figure 20:
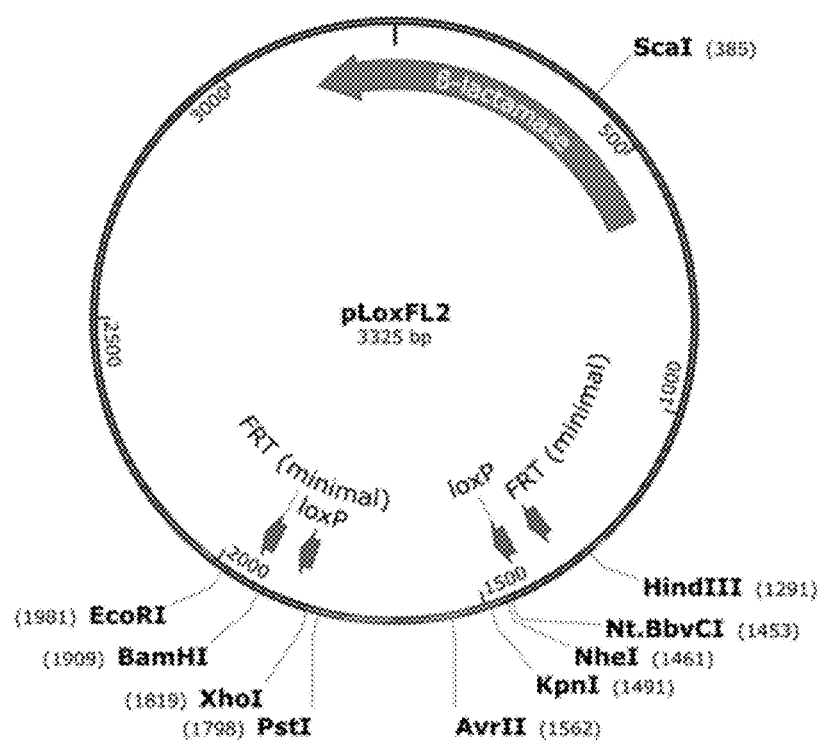
FIG. 20 shows a plasmid pLoxFL2 constructed for synthesizing circular DNA molecules by RCA or PCR. A 690 bp synthetic DNA fragment was cloned to the EcoRI and HindIII sites of pUC18. A pair of loxP sites and a pair of FRT minimal sites are included in the synthetic DNA fragment. Restriction sites XhoI, PstI, AvrII, KpnI, NheI, and Nt.BbvCI were placed in the 427 bp fragments between the two loxP sites. A BamHI site is also included in pLoxFL2.

A new plasmid pLoxFL2 (FIG. 20) was constructed for producing circular DNA molecules by RCA or polymerase chaining reaction (PCR). A 690 bp synthetic DNA fragment was cloned to the EcoRI and HindIII sites of pUC18. A pair of loxP sites and a pairs of FRT minimal sites are included in the synthetic DNA fragment. Restriction sites XhoI, PstI, AvrII, KpnI, NheI, and Nt.BbvCI were placed in the 427 bp fragments between the two loxP sites. A BamHI site is also included in pLoxFL2.

Figure 21A:
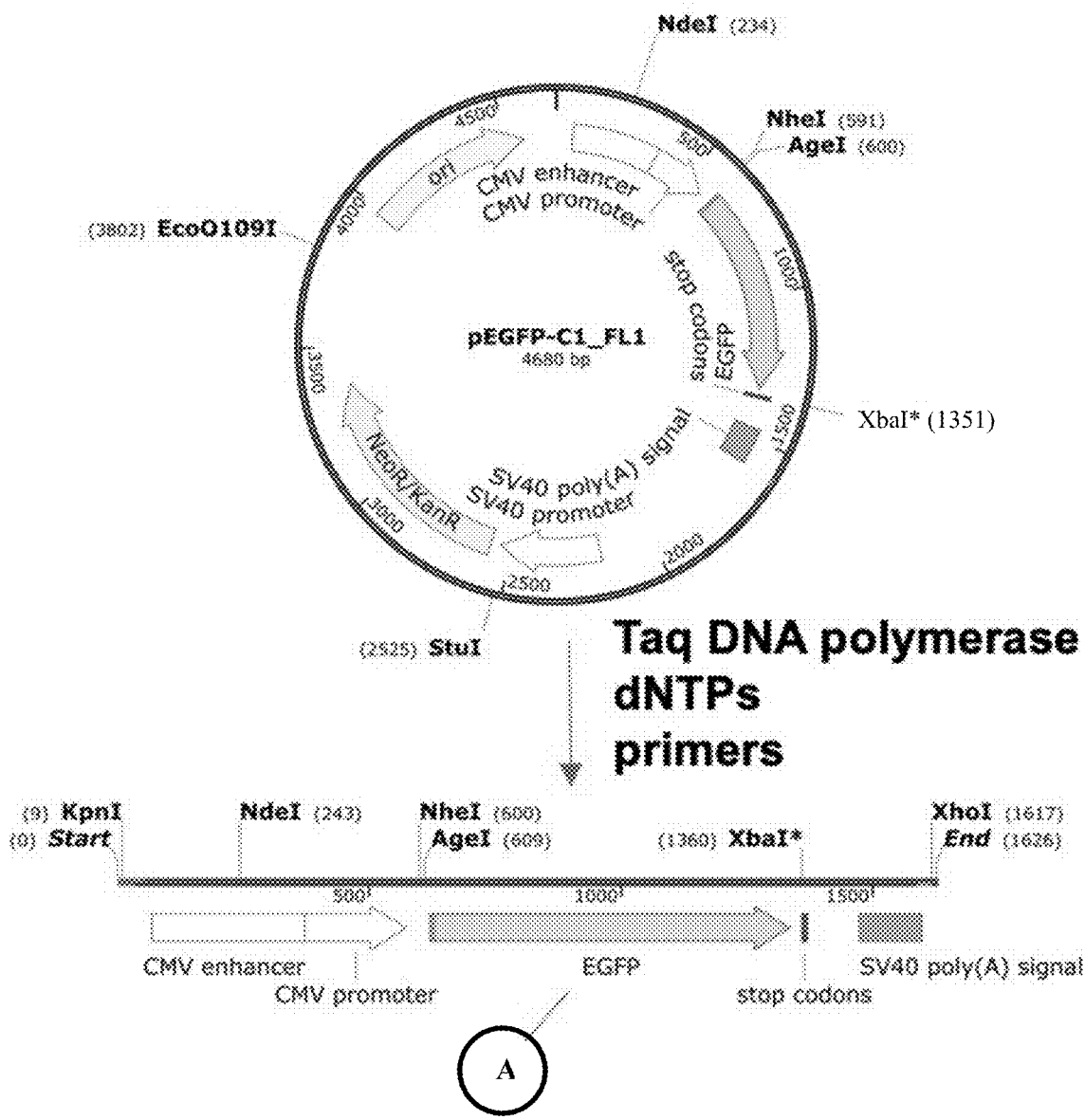
FIGS. 21A-21C show molecular cloning to construct DNA template pLoxFL3. Plasmid pEGFP-C1_FL1 was constructed from plasmid pEGFP-C1.
Figure 21B:
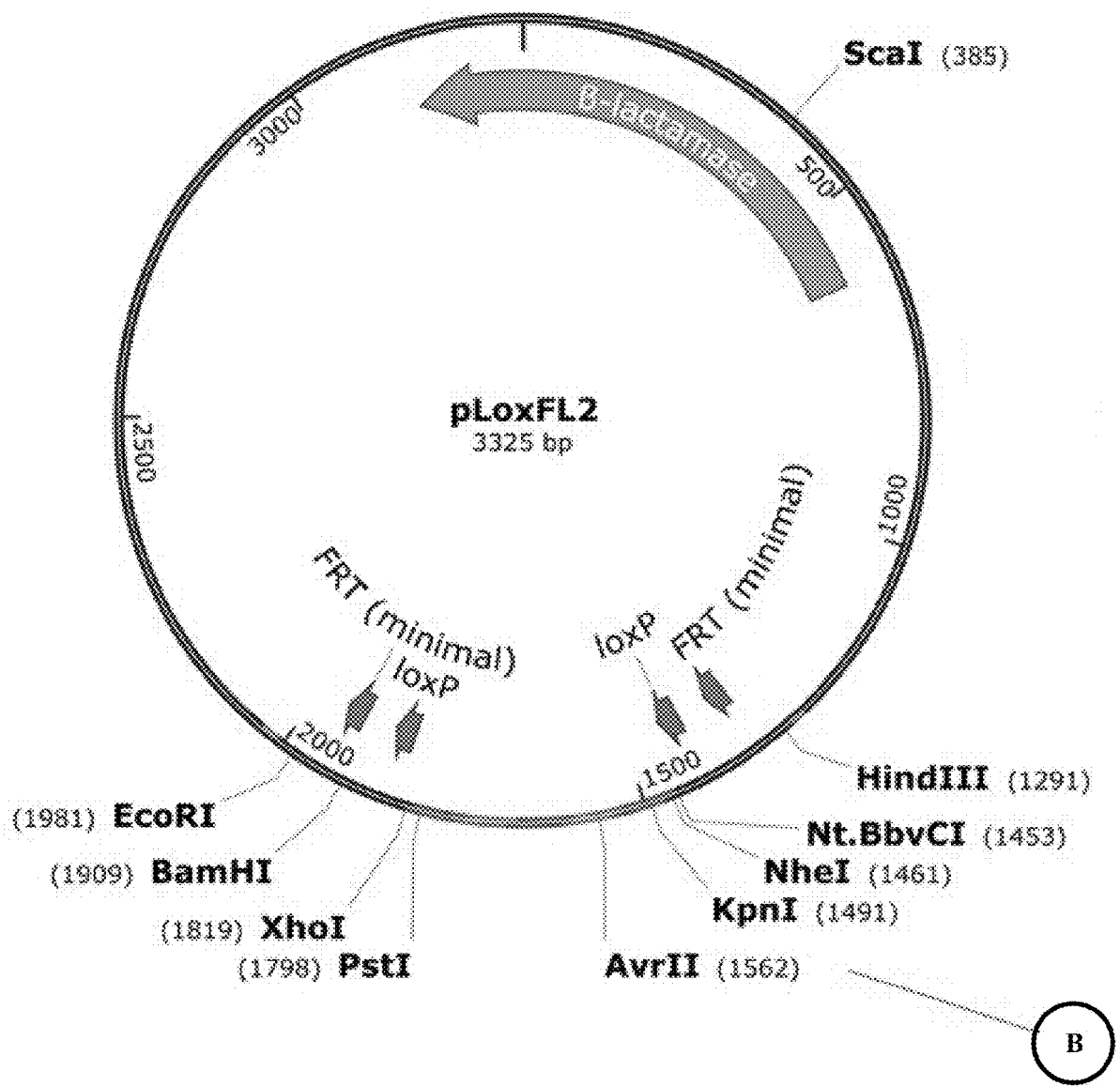
Figure 21C:
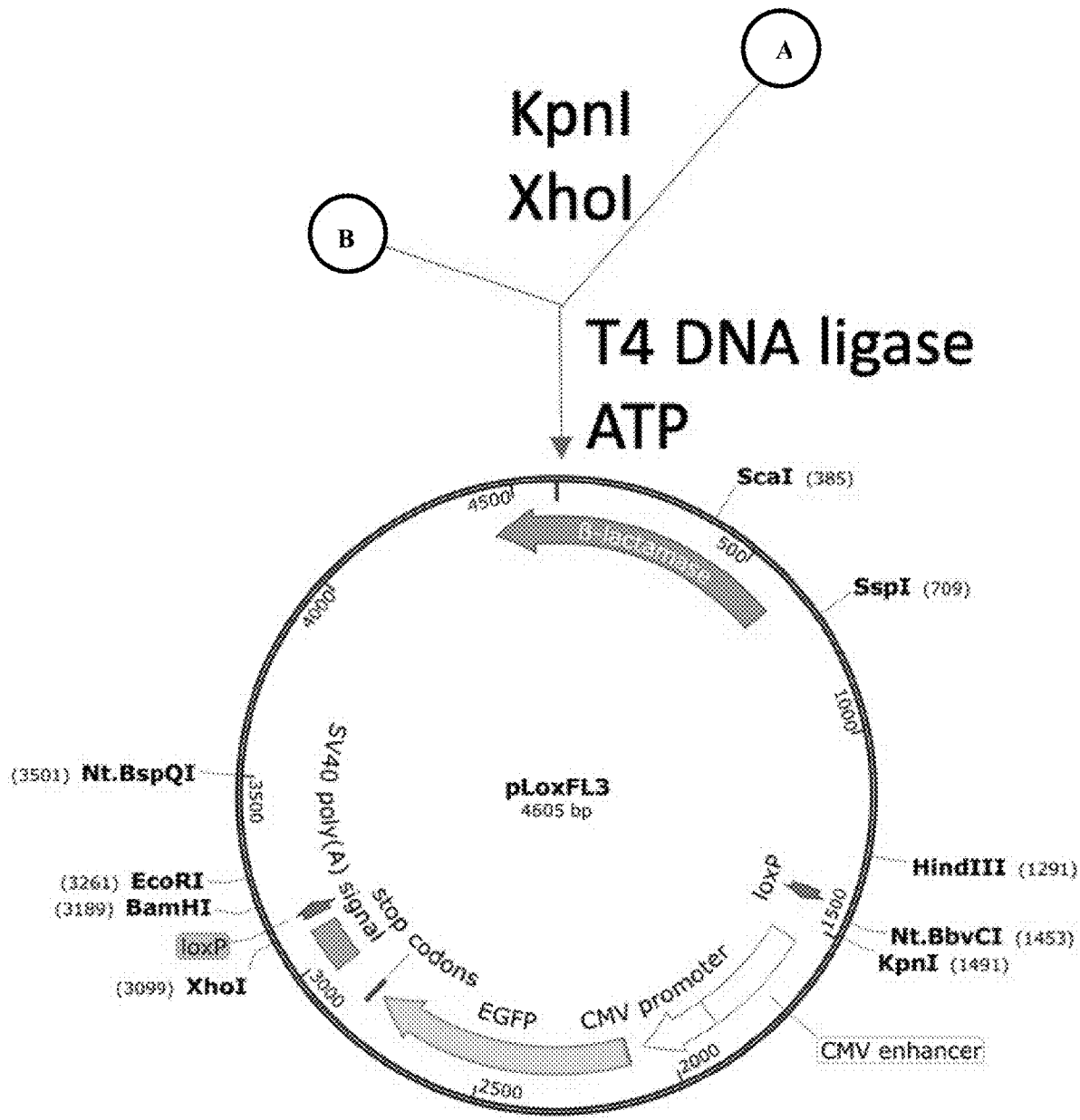

FIGS. 21A-21C show the construction of plasmid pLoxFL3. Plasmid pEGFP-C1_FL1 was constructed from plasmid pEGFP-C1, which was purchased from Gene Universal, Inc. A linear DNA molecule was produced from Plasmid pEGFP-C1_FL1 by RCA or PCR in the presence of Taq DNA polymerase, dNTPs, and primers. Restriction sites XhoI, KpnI, NheI, AgeI and XbaI were included in the linear DNA fragment. The linear DNA fragment was cloned to the KpnI and XhoI sites of pLoxFL2 to arrive at the plasmid pLoxFL3.

Figure 22A:
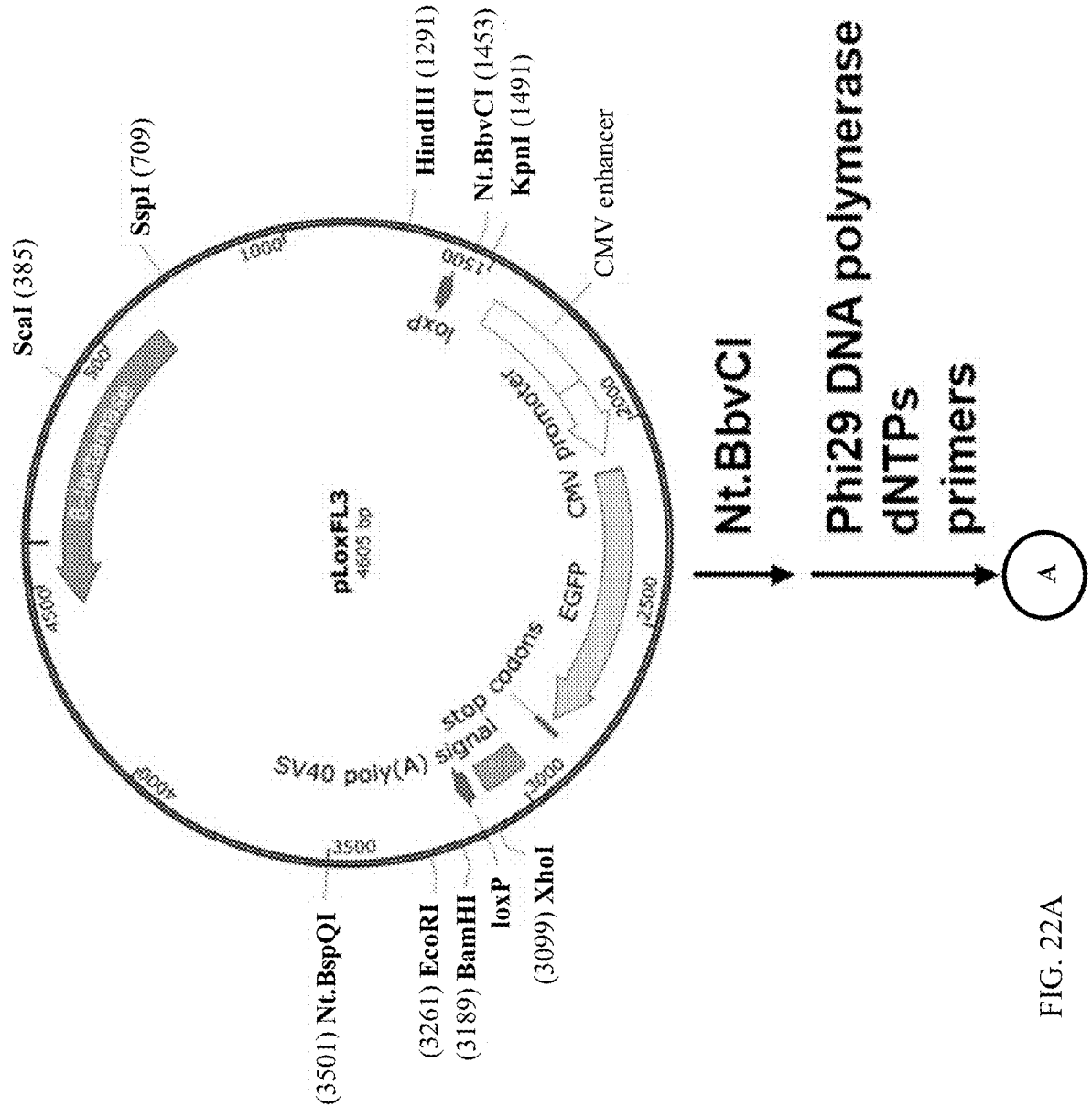
FIGS. 22A-22C show the synthesis of plasmid pLoxFL3 using RCA followed by recombination in vitro. The expression elements in this circular DNA molecule are only elements to express EGFP in human cells and there are no bacterial DNA elements.
Figure 22B:
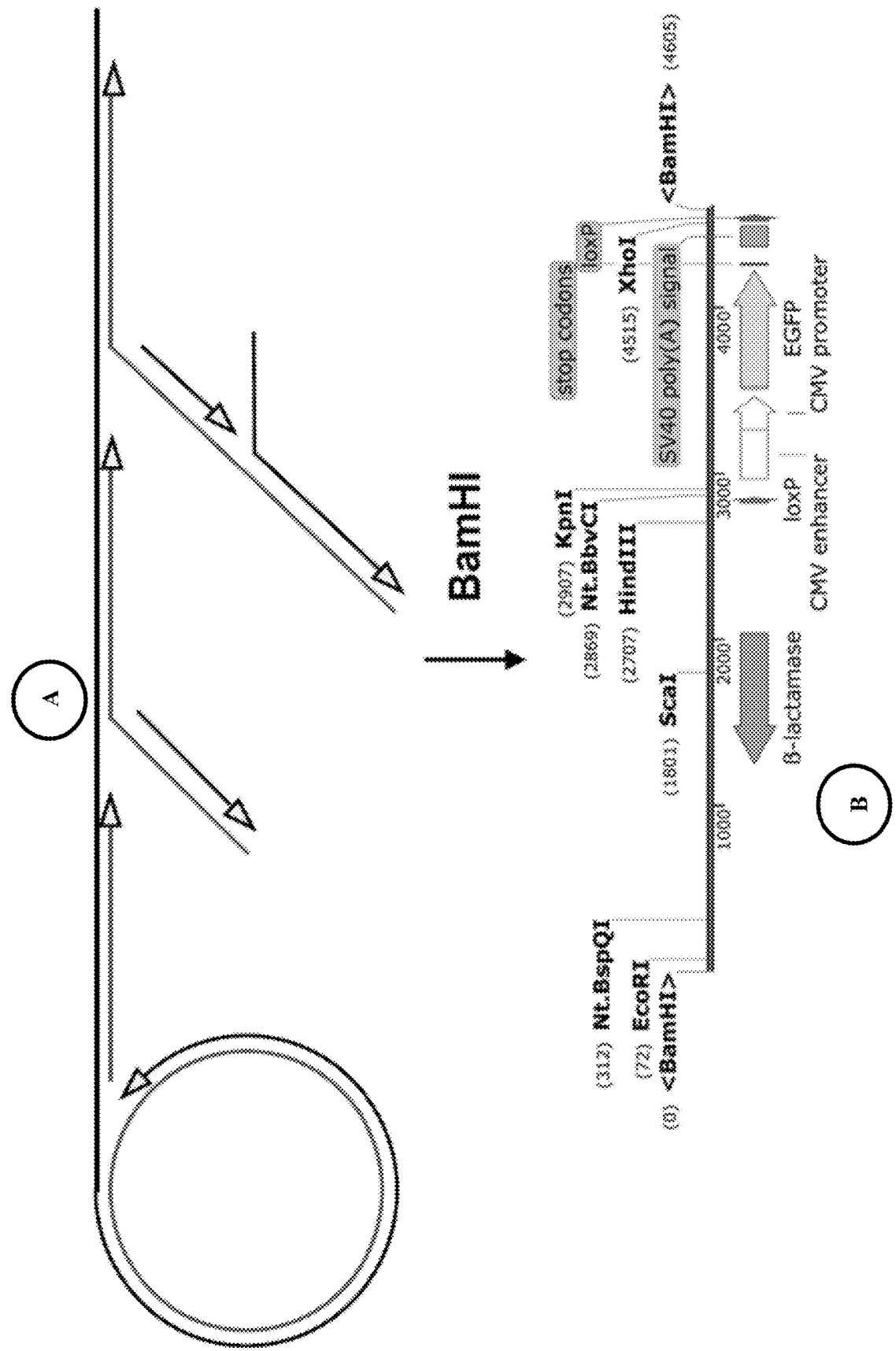
Figure 22C:
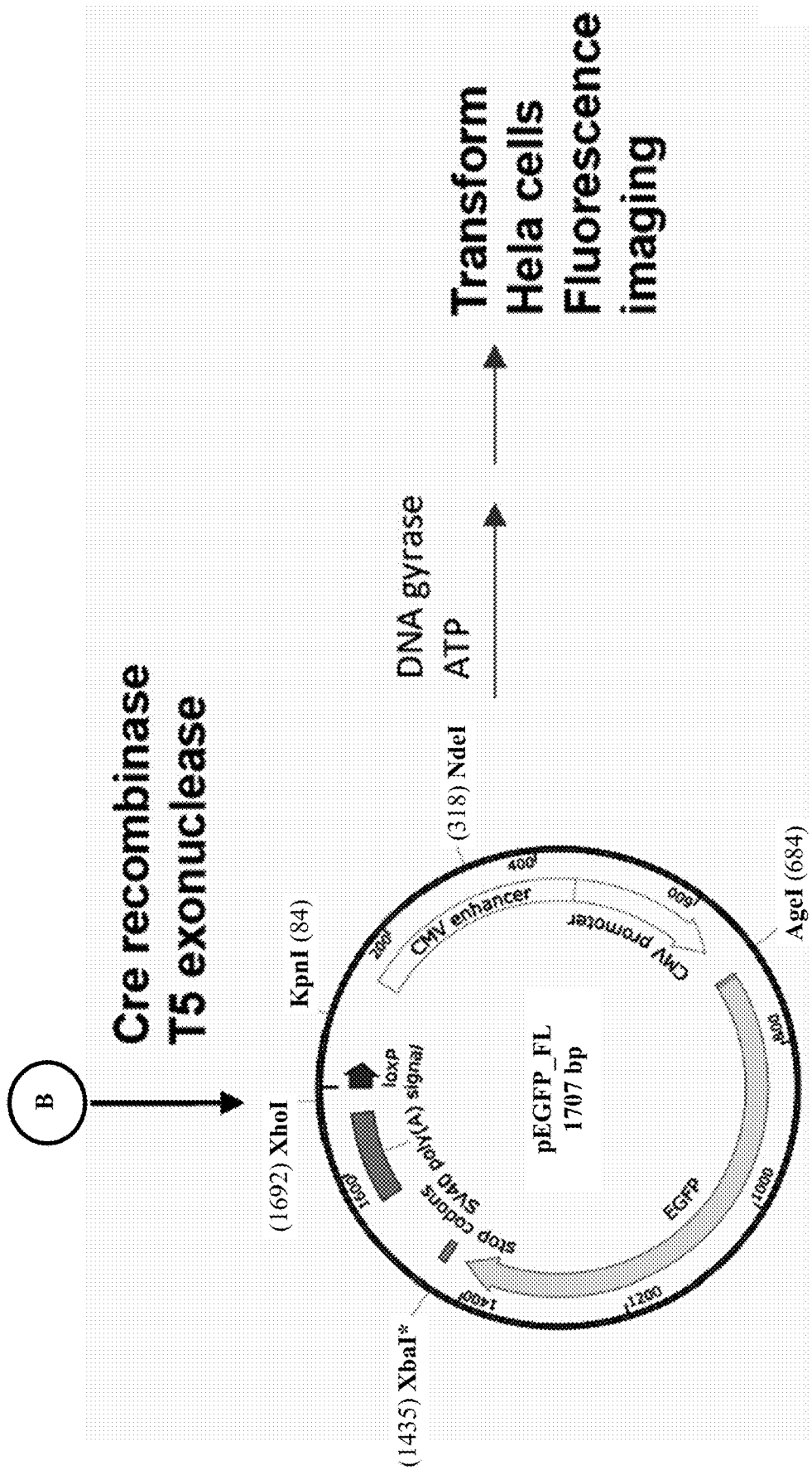

The synthesized plasmid pLoxFL3 can be used to produce a circular DNA molecule pEGFP_FL via RCA followed by recombination in vitro (FIGS. 22A-22C). The only expression elements in the circular DNA molecule pEGFP_FL are elements to express EGFP in human cells and there are no bacterial DNA elements.

Figure 1C:
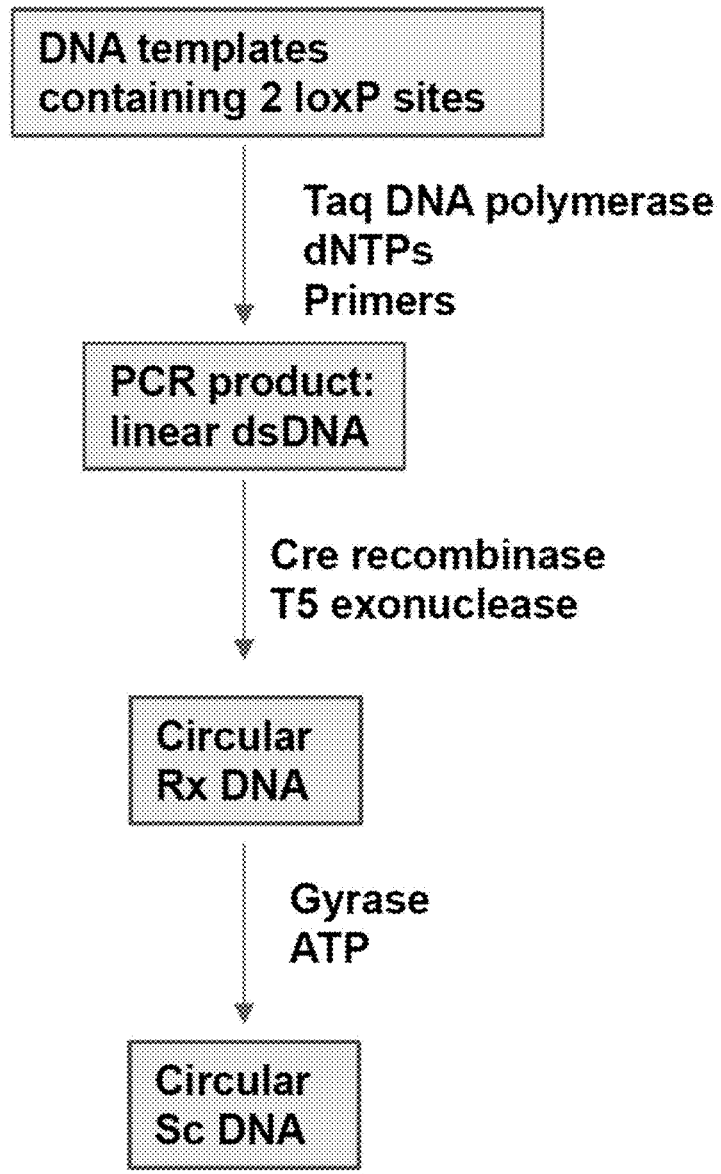

Example 6—Synthesizing Additional Circular DNA Molecules by Using Polymerase Chain Reaction FIG. 1C shows a scheme for synthesizing relaxed (Rx) and supercoiled (Sc) circular DNA molecules in vitro by using PCR. DNA templates containing 2 loxP sites were used for PCR in the presence of Taq DNA polymerase, dNTPs and primers to produce PCR products, linear ds DNA molecules. Cre recombinase converted the linear ds DNA molecules to relaxed circular DNA molecules and T5 exonuclease was added to degrade unligated linear DNA molecules. DNA gyrase was added to convert circular relaxed ds DNA molecules to circular supercoiled ds DNA molecules.

Figure 23A:
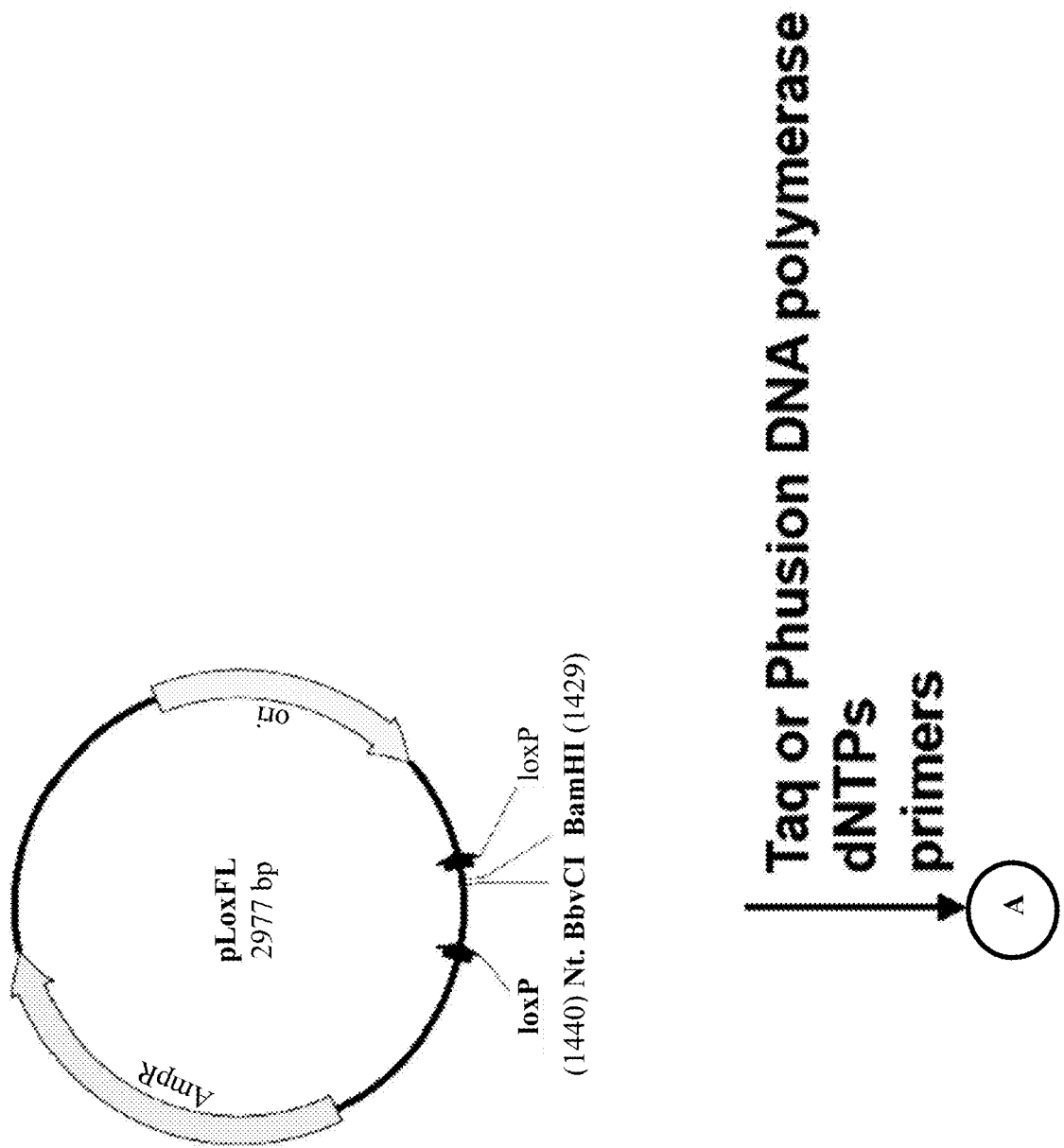
FIGS. 23A-23C show the synthesis of relaxed (Rx) and supercoiled (Sc) DNA molecules in vitro by PCR. The final products can be used to transform E. coli cells for molecular cloning.
Figure 23B:
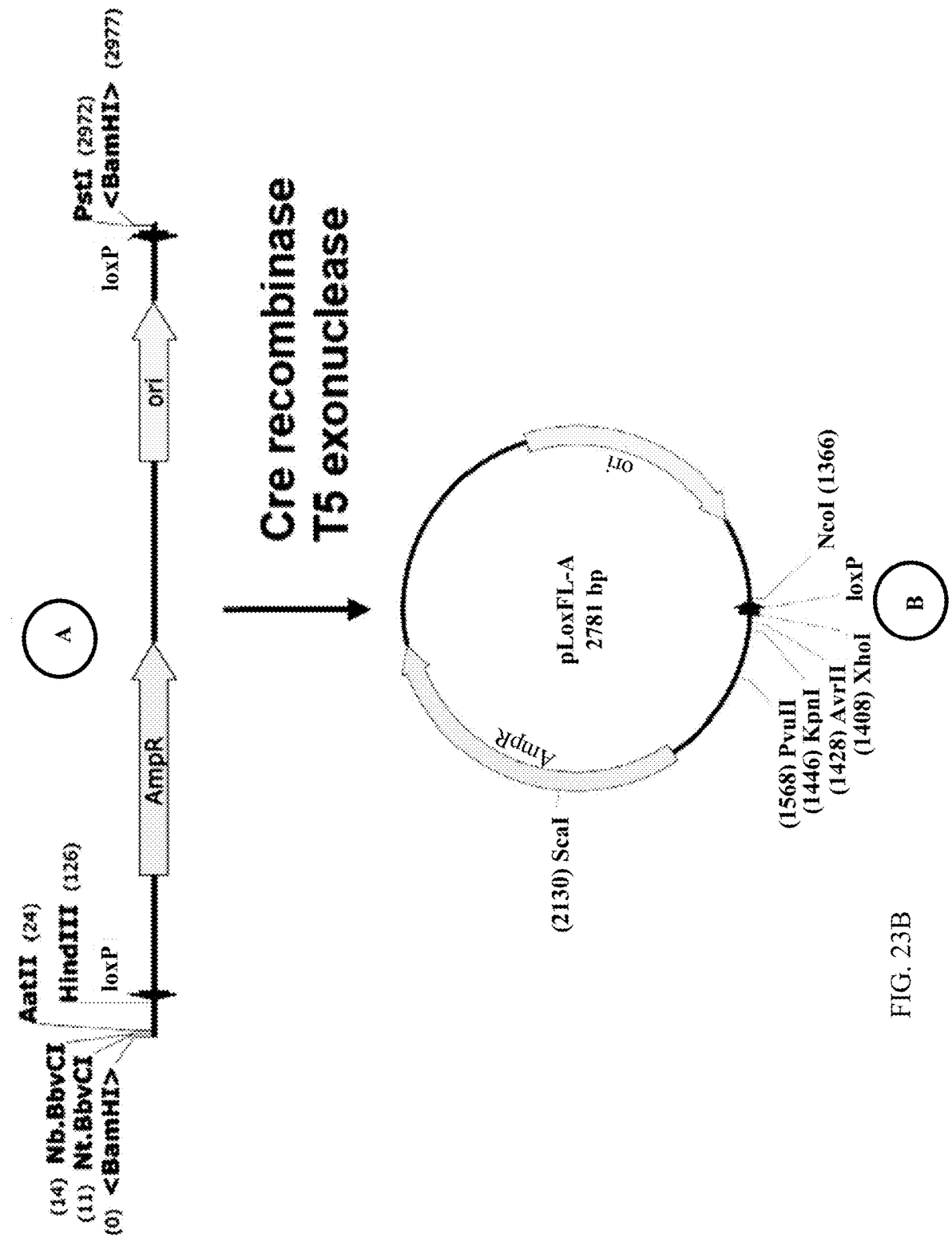
Figure 23C:
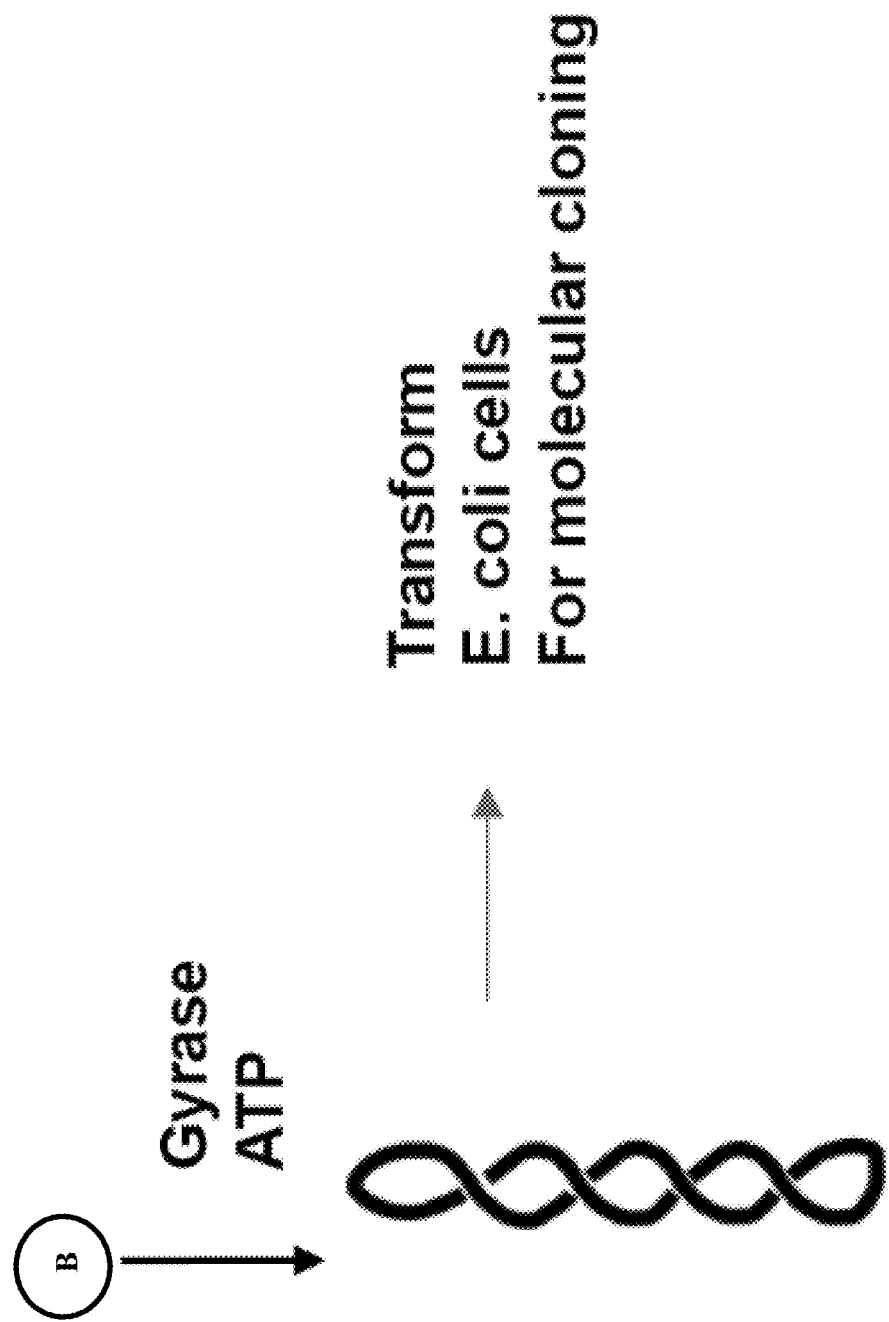

FIGS. 23A-23C show an experimental strategy to synthesize relaxed (Rx) and supercoiled (Sc) DNA molecules in vitro by PCR. PCR of pLoxFL was performed in the presence of Taq or Phusion DNA polymerase, dNTPs and primers to generate linear dsDNA molecules. To generate Rx and Sc circular DNA molecules, Cre recombinase was used to convert the linear DNA fragment carrying two loxP sites to Rx circular DNA molecules. DNA gyrase was used to convert the Rx circular DNA to Sc circular DNA molecules. The final products can be used to transform *E. coli* cells for molecular cloning.

Figure 24:
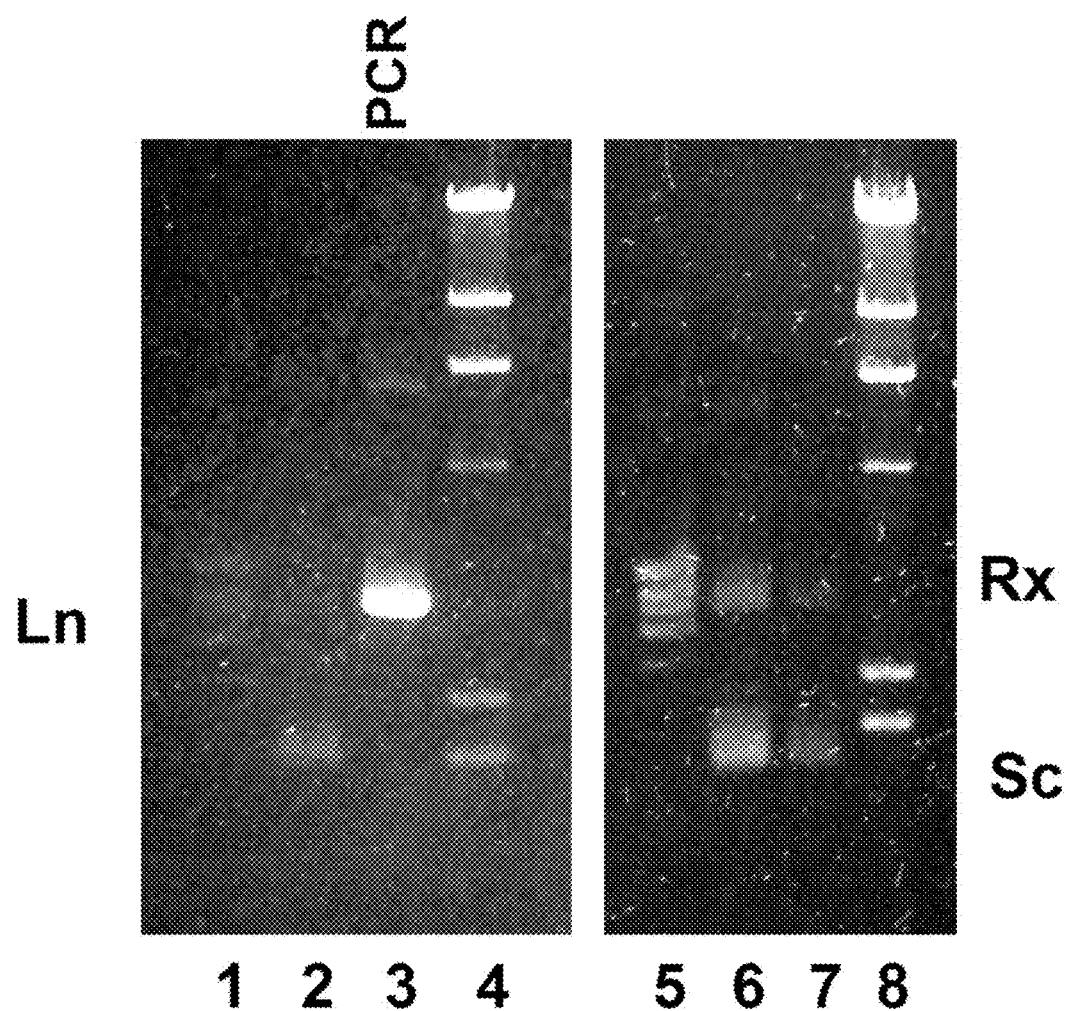
FIG. 24 shows the production of Rx and Sc circular DNA molecules by recombination using Cre DNA recombinase and PCR products. Agarose gel results show the synthesized plasmid pLoxFL-A according to FIGS. 23A-23C. Linear DNA fragments were synthesized by using plasmid pLoxFL as the DNA template, and FL1038 and FL1041 as primers by PCR using Phusion High-Fidelity DNA Polymerase. Lanes 1 and 5: recombination products, relaxed DNA; Lanes 2, 6, and 7: supercoiled DNA; Lane 3: PCR products using pLoxFL as the DNA template; and Lanes 4 and 8: lambda DNA HindIII digest.

FIG. 24 shows the agarose gels of synthesized plasmid pLoxFL-A according to strategy of FIGS. 23A-23C. Linear DNA fragments were synthesized by using plasmid pLoxFL as the DNA template, and FL1038 (5'-GGTGTCGGATC-CATGCTGCA-3' (SEQ ID NO: 1)) and FL1041 (5'-AAATAGGCGTATCACGAGGC-3' (SEQ ID NO: 2)) as primers by PCR using Phusion High-Fidelity DNA Polymerase. Lanes 1 and 5 show recombination products, relaxed DNA; Lanes 2, 6, and 7 show supercoiled DNA; Lane 3 are PCR products using pLoxFL as the DNA template; and Lanes 4 and 8 are lambda DNA HindIII digest.

Figure 25A:
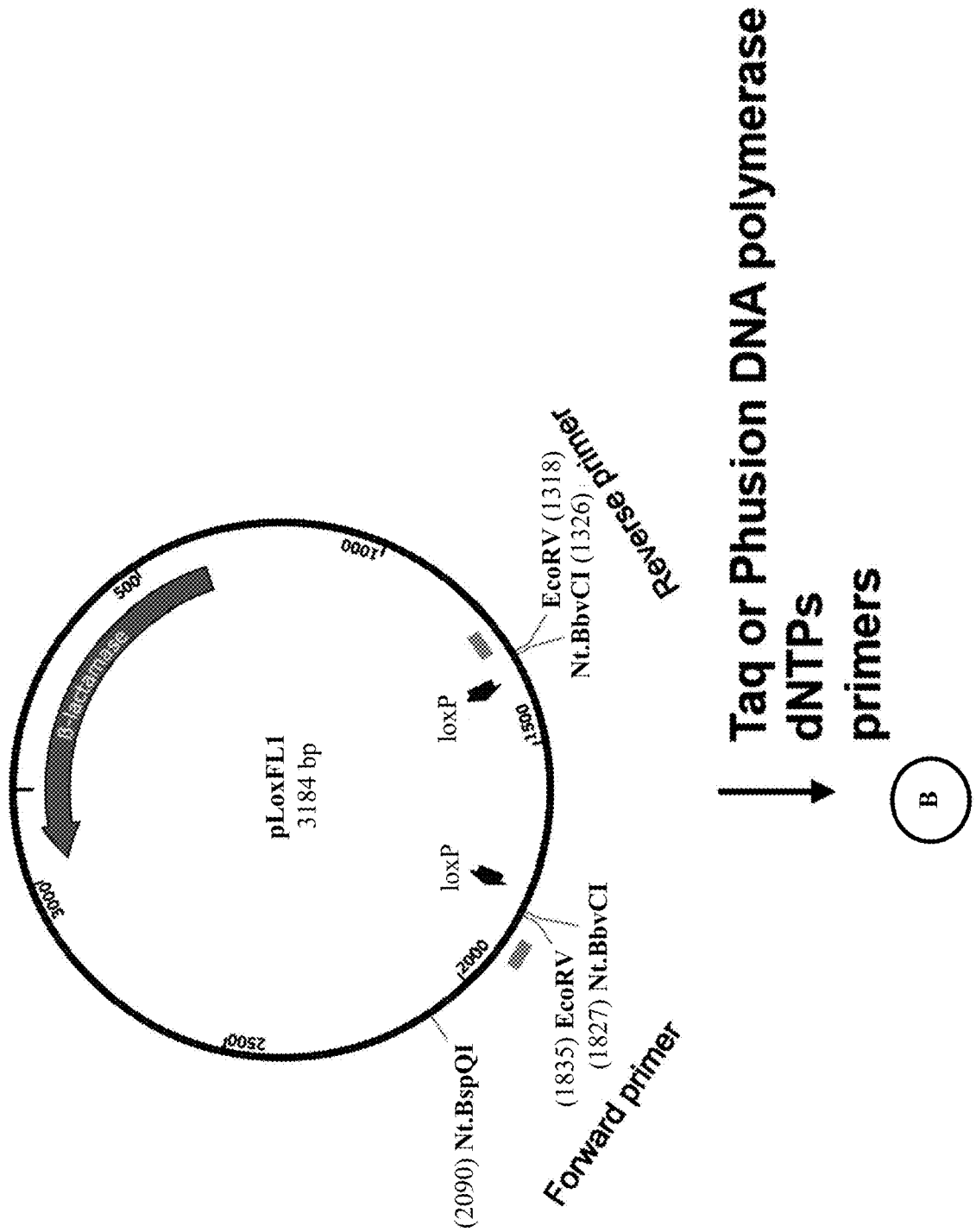
FIGS. 25A-25C show PCR-based DNA synthesis by Taq or Phusion DNA polymerase. A plasmid pLoxFL1 has been constructed for synthesizing circular DNA molecules by PCR. A 549 bp synthetic DNA fragment was cloned to the EcoRI and HindIII sites of pUC18. A pair of loxP sites are included in the synthetic DNA fragment. Restriction sites XhoI, PstI, KpnI, and NheI were placed in the 430 bp fragments between the two loxP sites. Two Nt.BbvCI and EcoRV sites are included. The final product is a relaxed (Rx) and supercoiled 430 bp mini circle 1.
Figure 25B:
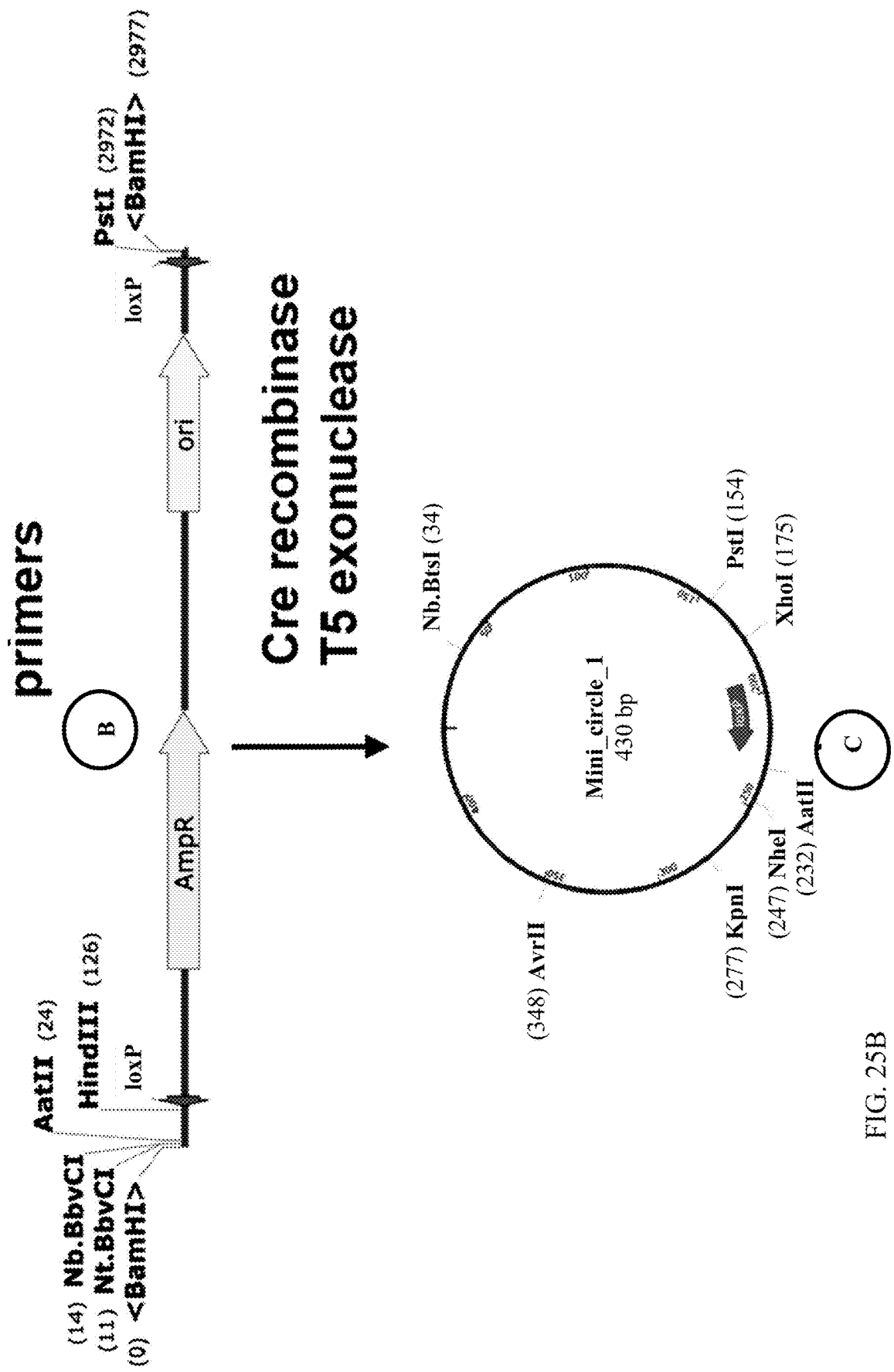
Figure 25C:
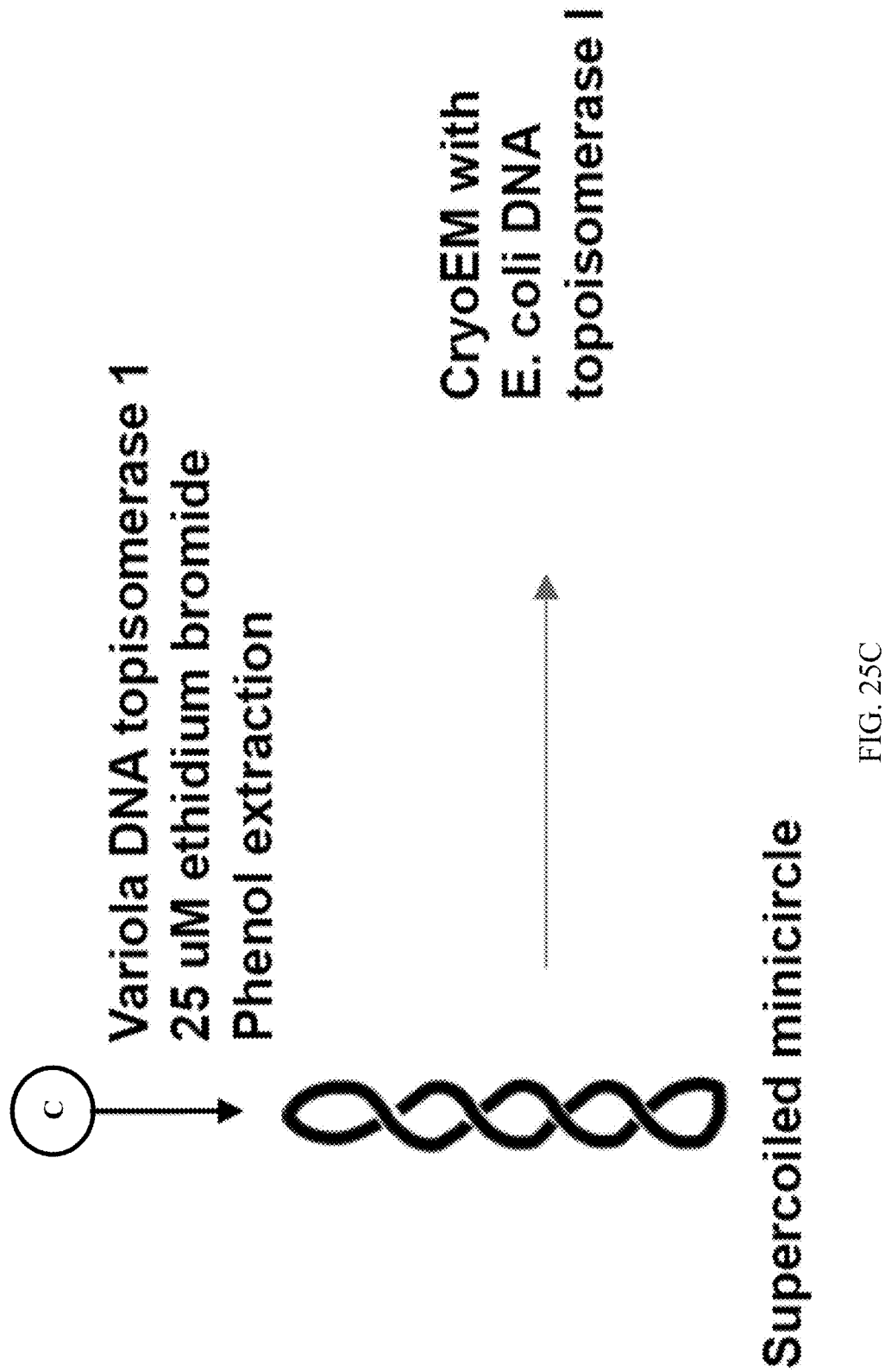

A new plasmid pLoxFL1 has been constructed for constructing circular DNA molecules by PCR (FIGS. 25A-25C). A 549 bp synthetic DNA fragment was cloned to the EcoRI and HindIII sites of pUC18. A pair of loxP sites are included in the synthetic DNA fragment. Restriction sites XhoI, PstI, KpnI, and NheI were placed in the 430 bp fragments between the two loxP sites. Two Nt.BbvCI and EcoRV sites are included.

PCR of pLoxFL1 was performed in the presence of Taq or Phusion DNA polymerase, dNTPs and primers to generate linear dsDNA molecules. To generate Rx Sc circular DNA molecules, Cre recombinase was used to convert the linear DNA fragment carrying two loxP sites to Rx circular DNA molecules. DNA topoisomerase I was used to convert the Rx circular DNA to Sc circular DNA molecules in the presence of 25 µM EB. After phenol extraction to remove EB, Sc circular DNA can be produced (FIGS. 25A-25C).

Figure 26:
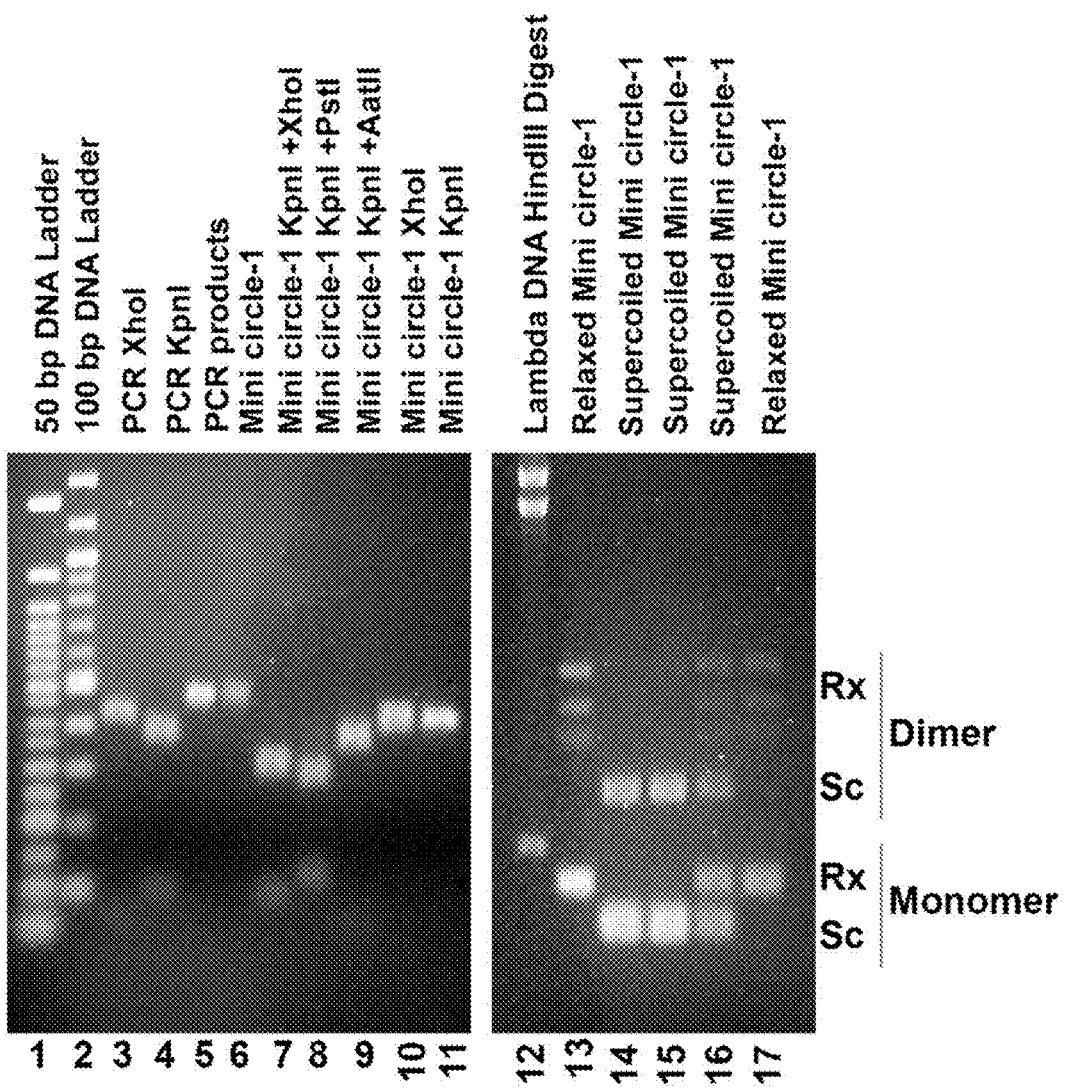
FIG. 26 shows the generation of Rx and Sc mini circle 1 DNA molecules by recombination using Cre DNA recombinase and by using PCR products. The left panel is the 1% agarose gel results to verify the identity of the 430 bp mini circle 1 by restriction enzyme mapping. DNA sequencing was confirmed the identity of the mini circle 1. The right panel (2% agarose gel) was supercoiling the mini circle 1 using Variola DNA topoisomerase I in the presence of 25 µM of ethidium bromide (EB). Lanes 13 and 17 are relaxed (Rx) mini circle 1. Lanes 14-16 contained 100, 50, and 25 nM of Variola DNA topoisomerase I. After phenol extraction, supercoiled (Sc) DNA was produced. Monomer and dimer are shown.

FIG. 26 shows the agarose gel results to verify the synthesized relaxed (Rx) and supercoiled 430 bp mini circle 1. The left panel is the 1% agarose gel results to verify the identity of the 430 bp mini circle 1 by restriction enzyme mapping. DNA sequencing was confirmed the identity of the mini circle 1. The right panel (2% agarose gel) was supercoiling the mini circle 1 using Variola DNA topoisomerase I in the presence of 25 µM of ethidium bromide (EB). Lanes 13 and 17 are relaxed (Rx) mini circle 1. Lanes 14-16 contained 100, 50, and 25 nM of Variola DNA topoisomerase I. After phenol extraction, supercoiled (Sc) DNA was produced. Monomer and dimer are also shown.

Figure 27:
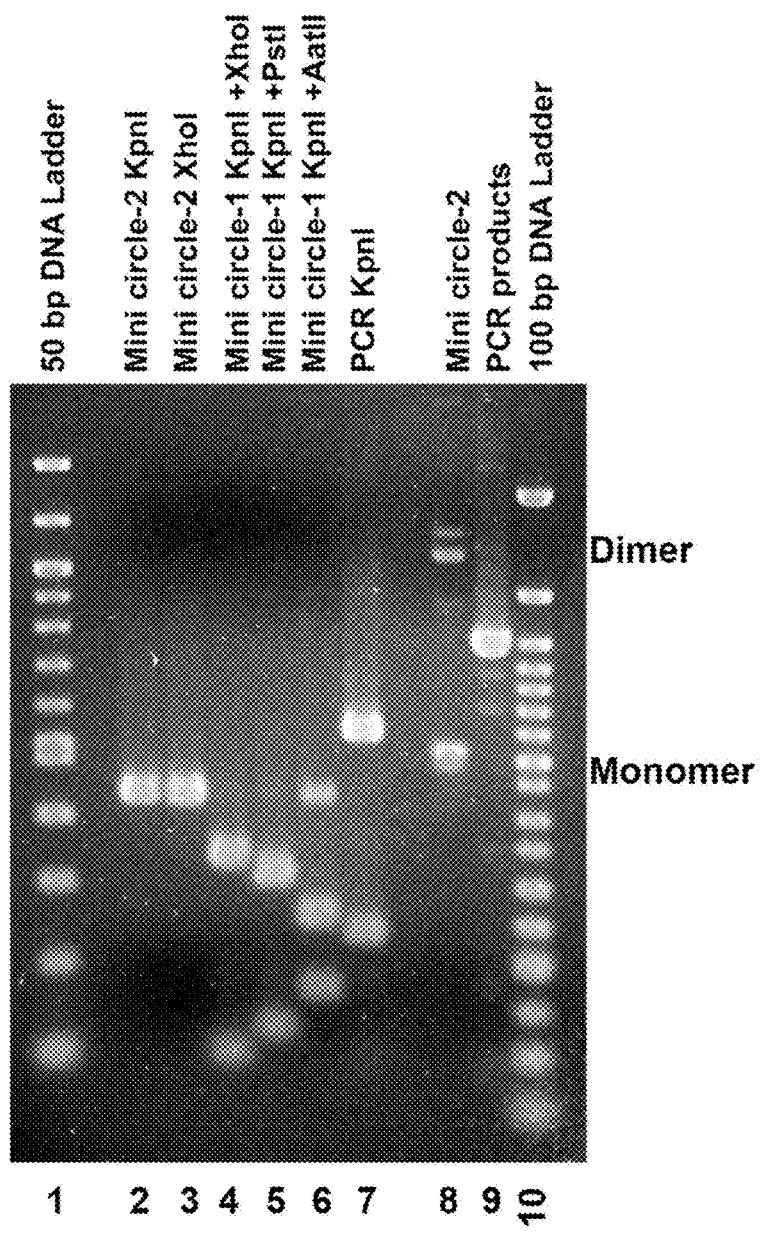
FIG. 27 shows the generation of Rx mini circle 2 DNA molecules by recombination using Cre DNA recombinase. Rx mini circle 2 (427 bp) was generated by using the PCR products (lane 9) using pLoxFL2 as the DNA template. The identity of the mini circle 2 was confirmed by using the restriction enzyme mapping.

FIG. 27 shows the generation of Rx mini circle 2 DNA molecules by recombination of PCR products using Cre DNA recombinase. Rx mini circle 2 was generated by using the PCR products (lane 9) and pLoxFL2 as the DNA template. The identity of the mini circle 2 was confirmed by using the restriction enzyme mapping.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

What is claimed is:

1. A method for synthesizing circular double-stranded DNA molecules, the method consisting of:
   providing a DNA template comprising two sequence-specific recombination sites;
   performing PCR to produce linear double-stranded DNA fragments comprising the two sequence-specific recombination sites;
   converting the linear double-stranded DNA fragments to relaxed circular double-stranded DNA molecules via a recombination reaction in the presence of a recombinase;
   removing unreacted linear double-stranded DNA fragments by adding an exonuclease; and
   optionally, converting the relaxed circular double-stranded DNA molecules to supercoiled double-stranded DNA molecules.

2. The method of claim 1, wherein the two sequence-specific recombination sites are selected from loxP sites, flippase recognition target (FRT) sites and a combination thereof.

3. The method of claim 1, wherein the PCR is performed in the presence of a DNA polymerase, dNTPs and primers selected from sequences comprising SEQ ID NO: 1 or 2.

4. The method of claim 1, wherein the recombinase is Cre recombinase.

5. The method of claim 1, wherein the exonuclease is T5 exonuclease.

6. The method of claim 1, wherein converting the relaxed circular double-stranded DNA molecules to supercoiled double-stranded DNA molecules comprises adding a DNA topoisomerase selected from DNA gyrase or DNA topoisomerase I.

7. The method of claim 1, wherein the DNA template is a circular DNA template.

* * * * *

SEQUENCE LISTING

```
Sequence total quantity: 2
SEQ ID NO: 1            moltype = DNA  length = 20
FEATURE                 Location/Qualifiers
source                  1..20
                        mol_type = other DNA
                        organism = synthetic construct
SEQUENCE: 1
ggtgtcggat ccatgctgca                                              20
```

```
SEQ ID NO: 2           moltype = DNA  length = 20
FEATURE                Location/Qualifiers
source                 1..20
                       mol_type = other DNA
                       organism = synthetic construct
SEQUENCE: 2
aaataggcgt atcacgaggc                                                   20
```